US011760776B2

(12) United States Patent
Levin et al.

(10) Patent No.: US 11,760,776 B2
(45) Date of Patent: Sep. 19, 2023

(54) METHODS FOR MODULATING PROTEIN EXPRESSION IN MICROORGANISMS

(71) Applicant: ORTERON (T.O) LTD., Kfar Saba (IL)

(72) Inventors: Tamar Levin, Kfar Saba (IL); Orit Ish-Yemini, Netanya (IL)

(73) Assignee: ORTERON (T.O) LTD., Kfar Saba (IL)

( * ) Notice: Subject to any disclaimer, the term of this patent is extended or adjusted under 35 U.S.C. 154(b) by 1045 days.

(21) Appl. No.: 16/400,183

(22) Filed: May 1, 2019

(65) Prior Publication Data

US 2019/0256553 A1     Aug. 22, 2019

Related U.S. Application Data

(63) Continuation-in-part of application No. PCT/IL2017/051192, filed on Nov. 1, 2017.
(Continued)

(51) Int. Cl.
*C07K 1/14* (2006.01)
*B01J 19/08* (2006.01)
(Continued)

(52) U.S. Cl.
CPC ............ *C07K 1/14* (2013.01); *B01J 19/08* (2013.01); *C12M 1/42* (2013.01); *C12M 35/02* (2013.01); *C12N 13/00* (2013.01); *C40B 40/02* (2013.01)

(58) Field of Classification Search
CPC . C07K 1/14; B01J 19/08; C12M 1/42; C12M 35/02; C12N 13/00; C40B 40/02
(Continued)

(56) References Cited

U.S. PATENT DOCUMENTS 8,725,248 B2   5/2014   Gutsol et al.
8,896,211 B2   11/2014  Ish-Yamini Tomer et al.
(Continued)

FOREIGN PATENT DOCUMENTS

KR         101773846 B1    9/2017

OTHER PUBLICATIONS

PCT Preliminary Report on Patentability for International Application No. PCT/IL2017/051192 dated Oct. 30, 2019.
(Continued)

*Primary Examiner* — Michael L Hobbs
*Assistant Examiner* — Lenora A Abel
(74) *Attorney, Agent, or Firm* — The Roy Gross Law Firm, LLC; Roy Gross

(57) ABSTRACT

The present invention discloses means, use and non-GM method for modulating proteins in microorganisms. This method comprising steps of providing a system comprising a plasma discharge source, the plasma; the plasma discharge electric field is in the range of about 200 to about 500 v/m; and a plasma modifying mechanism comprising (1) at least one magnetic material, and at least one piezoelectric material, and (2) at least one optical crystal material, the plasma modifying mechanism providing modified plasma output having frequencies in the range of about 3 KHz to about 30 KHz; and discharging the plasma towards the microorganisms in a pulsed profile; thereby modulating proteins from the target microorganisms. The invention also discloses means, use and non-GM method for de novo generating of proteins in microorganisms from within the proteome of the microorganisms. The method comprises steps of providing a system as defined above, and discharging the plasma towards microorganisms in a pulsed profile, thereby activating proteins from the target microorganisms to de novo
(Continued)

generating of proteins in microorganisms from within the proteome of the microorganisms.

3 Claims, 37 Drawing Sheets

Related U.S. Application Data

(60) Provisional application No. 62/415,517, filed on Nov. 1, 2016.

(51) Int. Cl.
*C12N 13/00* (2006.01)
*C40B 40/02* (2006.01)
*C12M 1/42* (2006.01)

(58) Field of Classification Search
USPC ........................................................ 435/287.1
See application file for complete search history.

(56) References Cited

U.S. PATENT DOCUMENTS

| | | | |
|---|---|---|---|
| 9,295,280 B2 | 3/2016 | Jacofsky et al. | |
| 9,521,736 B2 | 12/2016 | Jacofsky et al. | |
| 2016/0023183 A1* | 1/2016 | Levin ..................... | A61D 7/00 422/186.04 |

OTHER PUBLICATIONS

PCT Search Report for International Application No. PCT/IL2017/051192 dated Feb. 15, 2018.
PCT Written Opinion for International Application No. PCT/IL2017/051192 dated Feb. 15, 2018.
Analysis of the biological effects of a non-thermal plasma on *Saccharomyses cerevisiae*. Journal of the Korean Physical Society, 60(6), 916-920. https:// link.springer.com/article/10.3 93 8/jkps.60. 916, Park, G., Baik, K. Y., Kim, J. G., Kim, Y. J., Lee, K. A, Jung, R. J., & Cho, G., Mar. 22, 2012 (Mar. 22, 2012).
Impact of non-thermal plasma treatment on MAPK signaling pathways of human immune cell lines. Immunobiology, 218(10), 1248-1255. https://www.sciencedirect.com/science/article/pii/S0171298513000892, Bundscherer, L., Wende, K., Ottm?ller, K., Barton, A., Schmidt, A., Bekeschus, S., . . . & Lindequist, U. May 3, 2013 (May 3, 2013).
Proteomic tools to characterize non-thermal plasma effects in eukaryotic cells. Plasma Medicine, 3(1-2). http://www.dl.begellhouse.com/LJournals/5a5b4a3d4 I 93 87fb,4eec53 9e3 367 d43b,25dfe7f900c7bee5. html, Wende, K., Barton, A., Bekeschus, S., Bundscherer, L., Schmidt, A., Weltmann, K. D., & Masur, K. Dec. 31, 2013 (Dec. 31, 2013).
Large-scale gene function analysis with the PANTHER classification system. Nature protocols, 8(8), 1551. http://www.nature.com/articles/nprot.2013.092, Mi, H., Muruganujan, A., Casagrande, J. T., & Thomas, P. D., Jul. 18, 2013 (Jul. 18, 2013).
Ben Gadri et al. (2000). Sterilization and plasma processing of room temperature surfaces with a one atmosphere uniform glow discharge plasma (OAUGDP). Surface and Coatings Technology. 131. 528-541. doi: 10.1016/S0257-8972(00)00803-3.
Laroussi, M., & Lu, X. (2005). Room-temperature atmospheric pressure plasma plume for biomedical applications. Applied Physics Letters, 87(113902), 1-3. doi: 10.1063/1.2045549.
Montie, Th & Kelly-Wintenberg, Kimberly & Roth, J. (2000). An overview of research using a one atmosphere uniform glow discharge plasma (OAUGDP) for sterilization of surfaces and materials. Plasma Science, IEEE Transactions on. 28. 41-50. 10.1109/27.842860.
Nastuta, Andrei & Topala, Ionut & Grigoras, Constantin & Pohoata, Valentin & Popa, G. (2011). Stimulation of wound healing by helium atmospheric pressure plasma treatment. Journal of Physics D Applied Physics. 44. 10.1088/0022-3727/44/10/105204.
Middelkoop, Esther et al. (2012). Burn wound healing: a role for plasma medicine? In conference; 4th International Conference for Plasma Medicine (ICPM).
Nastuta, Andrei & Topala, Ionut & Grigoras, Constantin & Pohoata, Valentin & Popa, G. (2011). Stimulation of wound healing by helium atmospheric pressure plasma treatment. Journal of Physics D Applied Physics. 44. doi: 10.1088/0022-3727/44/10/105204.
Lee, Kwon-Yong & Park, bong joo & Lee, Dong & Lee, In-Seop & Hyun, Soon & Chung, Kie-Hyung & Park, Chul. (2005). Sterilization of *Escherichia coli* and MRSA using microwave-induced argon plasma at atmospheric pressure. Surface and Coatings Technology. 193. 35-38. doi: 10.1016/j.surfcoat.2004.07.034.
Sladek, R & Stoffels, Eva. (2005). Deactivation of *Escherichia coli* by Plasma Needle. Journal of Physics D: Applied Physics. 38. 1716. doi:10.1088/0022-3727/38/11/012.
Laroussi, Mounir & Mendis, Devan & Rosenberg, Mathilda. (2003). Plasma interaction with microbes. New Journal of Physics. 5. 41. doi: 10.1088/1367-2630/5/1/341.
Montenegro, J., Ruan, R., Ma, H. and Chen, P. (2002), Inactivation of *E. coli* O157:H7 Using a Pulsed Nonthermal Plasma System. Journal of Food Science, 67: 646-648. https://doi.org/10.1111/j.1365-2621.2002.tb10653.x.
Jingjing, Liu & Wang, X. & Xingcheng, Yuan & Mingzhe, Rong. (2006). Efficiency of Removing Sulfur Dioxide in the Air by Non-Thermal Plasma Along with the Application of the Magnetic Field. Plasma Science and Technology. 7. 3073. 10.1088/1009-0630/7/5/023.
K. Kelly-Wintenberg, Amanda Hodge, T. C. Montie, et al. (1999). Use of a one atmosphere uniform glow discharge plasma to kill a broad spectrum of microorganisms. Journal of Vacuum Science & Technology A 17, 1539 (1999); https://doi.org/10.1116/1.581849.
Dunaevsky, A & Chirko, Konstantin & Krasik, Yakov & Felsteiner, Joshua & Bernshtam, V. (2001). Spectroscopy of a Ferroelectric Plasma Cathode. Journal of Applied Physics—Journal of Applied Physics, 90(8) doi: 0.1063/1.1404421.
Holzer, F., Kopinke, F.D. & Roland, U. (2005). Influence of Ferroelectric Materials and Catalysts on the Performance of Non-Thermal Plasma (NTP) for the Removal of Air Pollutants. Plasma Chemistry and Plasma Processing, vol. 25, No. 6, Dec. 2005, DOI: 10.1007/s11090-005-6804-1.
Thiele, Thomas & Steil, Leif & Gebhard, Simon & Scharf, Christian & Hammer, Elke & Brigulla, Matthias & Lubenow, Norbert & Clemetson, Kenneth & Völker, Uwe & Greinacher, Andreas. (2007). Profiling of alterations in platelet proteins during storage of platelet concentrates. Transfusion. 47. 1221-33. doi: 10.1111/j.1537-2995. 2007.01255.x.
Hammer, Elke & Truong Quoc, Phong & Steil, Leif & Klingel, Karin & Gesell, Manuela & Bernhardt, Jörg & Kandolf, Reinhard & Kroemer, Heyo & Felix, Stephan & Völker, Uwe. (2010). Viral myocarditis induced by Coxsackievirus B3 in A.BY/SnJ mice: Analysis of changes in the myocardial proteome. Proteomics. 10. 1802-18. 10.1002/pmic.200900734.
Nesvizhskii, Alexey & Keller, Andrew & Kolker, Eugene & Aebersold, Ruedi. (2003). A Statistical Model for Identifying Proteins by Tandem Mass Spectrometry. Analytical chemistry. 75. 4646-58. doi: 10.1021/ac0341261.
E. Stoffels et al. (2002). Plasma needle: a non-destructive atmospheric plasma source for fine surface treatment of (bio)materials. Plasma Sources Sci. Technol. 11: 383-388; DOI 10.1088/0963-0252/11/4/304.
Eymann C, Dreisbach A, Albrecht D, Bernhardt J, Becher D, Gentner S, Tam Ie T, Büttner K, Buurman G, Scharf C, Venz S, Völker U, Hecker M. A comprehensive proteome map of growing Bacillus subtilis cells. Proteomics. Oct. 2004;4(10):2849-76. doi: 10.1002/pmic.200400907. PMID: 15378759.
Keller, Andrew & Nesvizhskii, Alexey & Kolker, Eugene & Aebersold, Ruedi. (2002). Empirical Statistical Model to Estimate the Accuracy of Peptide Identifications Made by MS/MS and Database Search. Analytical chemistry. 74. 5383-92. doi: 10.1021/ac025747h.

(56) References Cited

OTHER PUBLICATIONS

R.E.J Sladek and E. Stoffels (2005). Deactivation of *Escherichia coli* by the plasma needle. Journal of Physics D: Applied Physics. 38. 1716. doi: 10.1088/0022-3727/38/11/012.

Machala, Zdenko & Hensel, Karol & Akishev, Yuri. (2012). Plasma for Bio-Decontamination, Medicine and Food Security. NATO Science for Peace and Security Series A: Chemistry and Biology; doi: 10.1007/978-94-007-2852-3.

Zongbao Feng, Noboru Saeki, Tomoyuki Kuroki, et al. (2012). Surface modification by nonthermal plasma induced by using magnetic-field-assisted gliding arc discharge; Appl. Phys. Lett. 101, 041602 (2012); https://doi.org/10.1063/1.4738766.

* cited by examiner

- calcium-binding protein (PC00060)
- cell adhesion molecule (PC00069)
- chaperone (PC00072)
- enzyme modulator (PC00095)
- hydrolase (PC00121)
- ligase (PC00142)
- lyase (PC00144)
- membrane traffic protein (PC00150)
- nucleic acid binding (PC00171)
- oxidoreductase (PC00176)
- signaling molecule (PC00207)
- transcription factor (PC00218)
- transfer/carrier protein (PC00219)
- transferase (PC00220)
- transporter (PC00227)

PANTHER Pathway
Total #Genes: 82 Total# pathway hits: 15

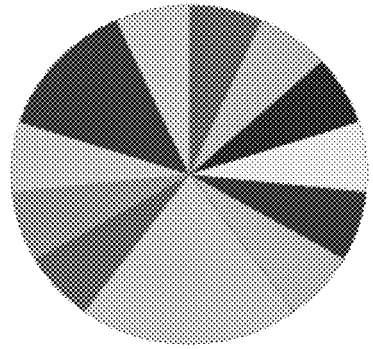

| | |
|---|---|
| | Apoptosis signaling pathway (P00006) |
| | DNA replication (P00017) |
| | General transcription regulation (P00023) |
| | Gonadotropin-releasing hormone receptor pathway (P06664) |
| | Heme biosynthesis (P02746) |
| | Methionine biosynthesis (P02753) |
| | Parkinson disease (P00049) |
| | Pyruvate metabolism (P02772) |
| | Salvage pyrimidine ribonucleotides (P02775) |
| | Transcription regulation by bZIP transcription factor (P00055) |
| | Ubiquitin proteasome pathway (P00060) |
| | Wnt signaling pathway (P00057) |

Fig. 3A

Apoptosis signaling pathway (P00006)

DNA replication (P00017)

General transcription regulation (P00023)

Gonadotropin-releasing hormone receptor pathway (P06664)

Heme biosynthesis (P02746)

Methionine biosynthesis (P02753)

Parkinson disease (P00049)

Pyruvate metabolism (P02772)

Salvage pyrimidine ribonucleotides (P02775)

Transcription regulation by bZIP transcription factor (P00055)

Ubiquitin proteasome pathway (P00060)

Wnt signaling pathway (P00057)

Fig. 3B

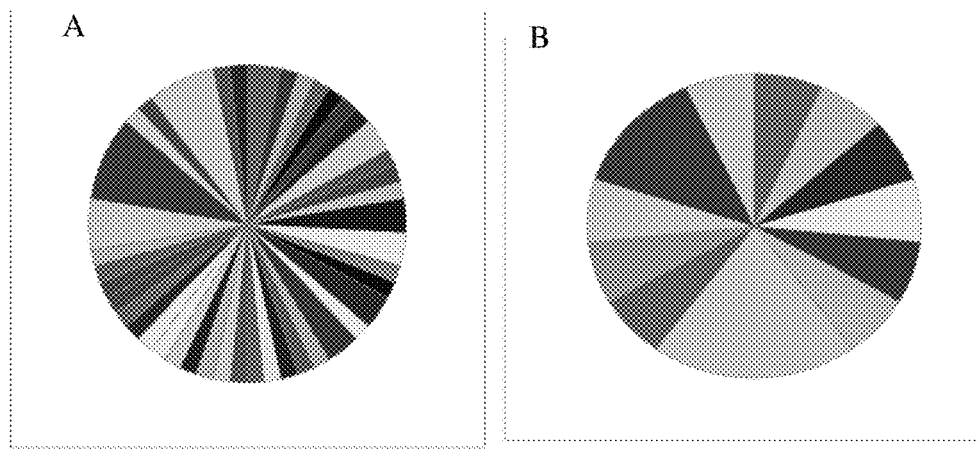

- 5-Hydroxytryptamine degradation
- Alanine biosynthesis
- Aminobutyrate degradation
- Apoptosis signaling pathway
- Arginine biosynthesis
- B cell activation
- CCKR signaling map
- Cell cycle
- Cholesterol biosynthesis
- Apoptosis signaling pathway (P00006)
- DNA replication (P00017)
- General transcription regulation (P00023)
- Gonadotropin-releasing hormone receptor pathway (P06664)
- Heme biosynthesis (P02746)
- Methionine biosynthesis (P02753)
- Parkinson disease (P00049)
- Pyruvate metabolism (P02772)
- Salvage pyrimidine ribonucleotides (P02775)

Fig. 4A

- Nicotinic acetylcholine receptor signaling pathway
- PDGF signaling pathway
- Parkinson disease
- Purine metabolism
- Pyridoxal phosphate salvage
- Pyridoxal-5-phosphate biosynthesis
- Pyruvate metabolism
- Ras Pathway
- TCA cycle
- TGF-beta signaling pathway
- Thiamin metabolism
- Transcription regulation by bZIP transcription factor
- Ubiquitin proteasome pathway
- Valine biosynthesis
- Vitamin B6 metabolism
- Wnt signaling pathway
- p38 MAPK pathway
- p53 pathway

Fig. 4C

A                                    B
PANTHER Pathway                     PANTHER Pathway
Total #Genes: 194 Total# pathway hits: 35    Total #Genes: 137 Total# pathway hits: 15
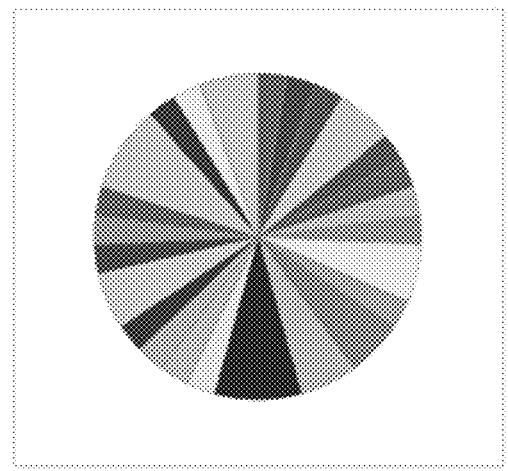 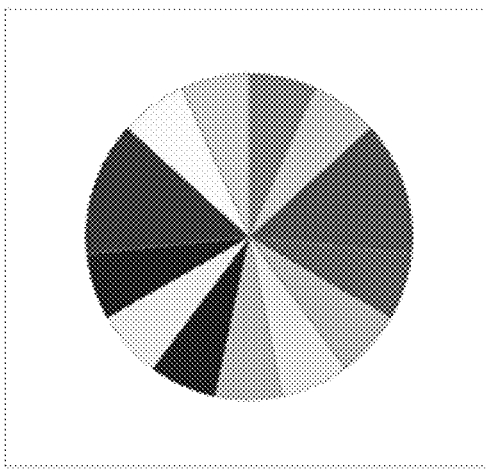
Fig. 5A

| | |
|---|---|
| 5-Hydroxytryptamine degradation (P04372) | Angiogenesis (P00005) |
| Adrenaline and noradrenaline biosynthesis (P00001) | Cell cycle (P00013) |
| | Cholesterol biosynthesis (P00014) |
| Cadherin signaling pathway (P00012) | Cytoskeletal regulation by Rho GTPase (P00016) |
| Cell cycle (P00013) | DNA replication (P00017) |
| Cholesterol biosynthesis (P00014) | Huntington disease (P00029) |
| Coenzyme A biosynthesis (P02736) | Methionine biosynthesis (P02753) |
| DNA replication (P00017) | PDGF signaling pathway (P00047) |
| De novo pyrimidine deoxyribonucleotide biosynthesis (P02739) | Purine metabolism (P02769) |
| | Tryptophan biosynthesis (P02783) |
| De novo pyrimidine ribonucleotides biosynthesis (P02740) | Ubiquitin proteasome pathway (P00060) |
| | VEGF signaling pathway (P00056) |
| EGF receptor signaling pathway (P00018) | mRNA splicing (P00058) |
| Flavin biosynthesis (P02741) | |

Fig. 5B

5-Hydroxytryptamine degradation (P04372)

Adrenaline and noradrenaline biosynthesis (P00001)

Cadherin signaling pathway (P00012)

Cell cycle (P00013)

Cholesterol biosynthesis (P00014)

Coenzyme A biosynthesis (P02736)

DNA replication (P00017)

De novo pyrimidine deoxyribonucleotide biosynthesis (P02739)

De novo pyrimidine ribonucleotides biosythesis (P02740)

EGF receptor signaling pathway (P00018)

Flavin biosynthesis (P02741)

Formyltetrahydroformate biosynthesis (P02743)

General transcription regulation (P00023)

Huntington disease (P00029)

Methionine biosynthesis (P02753)

Nicotinic acetylcholine receptor signaling pathway (P00044)

Oxidative stress response (P00046)

Parkinson disease (P00049)

S-adenosylmethionine biosynthesis (P02773)

Salvage pyrimidine ribonucleotides (P02775)

Fig. 5C

- Tetrahydrofolate biosynthesis (P02742)
- Transcription regulation by bZIP transcription factor (P00055)
- Ubiquitin proteasome pathway (P00060)
- Vitamin D metabolism and pathway (P04396)
- Wnt signaling pathway (P00057)
- 5-Hydroxytryptamine degradation (P04372)
- Adrenaline and noradrenaline biosynthesis (P00001)
- Cadherin signaling pathway (P00012)
- Cell cycle (P00013)
- Cholesterol biosynthesis (P00014)
- Coenzyme A biosynthesis (P02736)
- DNA replication (P00017)
- De novo pyrimidine deoxyribonucleotide biosynthesis (P02739)
- De novo pyrimidine ribonucleotides biosynthesis (P02740)
- EGF receptor signaling pathway (P00018)
- Flavin biosynthesis (P02741)
- Formyltetrahydroformate biosynthesis (P02743)
- General transcription regulation (P00023)
- Huntington disease (P00029)
- Methionine biosynthesis (P02753)
- Nicotinic acetylcholine receptor signaling pathway (P00044)
- Oxidative stress response (P00046)
- Parkinson disease (P00049)

Fig. 5D

Salvage pyrimidine ribonucleotides (P02775)

Tetrahydrofolate biosynthesis (P02742)

Transcription regulation by bZIP transcription factor (P00055)

Ubiquitin proteasome pathway (P00060)

Vitamin D metabolism and pathway (P04396)

Wnt signaling pathway (P00057)

Fig. 5E

A                                    B
PANTHER Pathway                PANTHER Pathway
Total #Genes: 88 Total# pathway hits: 72    Total #Genes: 94  Total# pathway hits: 74
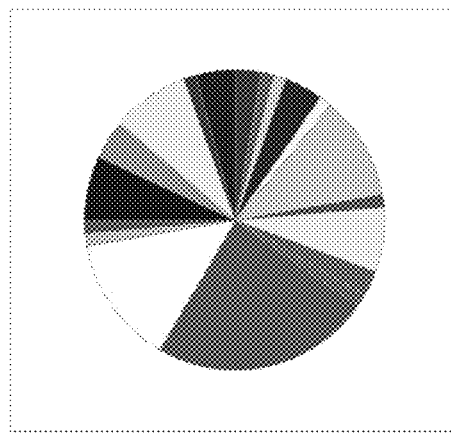 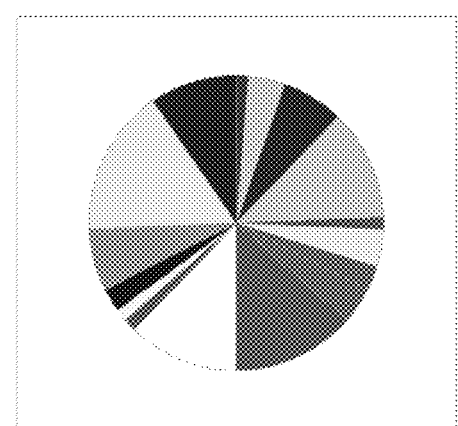
Fig. 6A

| | |
|---|---|
| calcium-binding protein (PC00060) | calcium-binding protein (PC00060) |
| chaperone (PC00072) | cytoskeletal protein (PC00085) |
| cytoskeletal protein (PC00085) | enzyme modulator (PC00095) |
| enzyme modulator (PC00095) | hydrolase (PC00121) |
| extracellular matrix protein (PC00102) | isomerase (PC00135) |
| hydrolase (PC00121) | ligase (PC00142) |
| isomerase (PC00135) | lyase (PC00144) |
| ligase (PC00142) | membrane traffic protein (PC00150) |
| lyase (PC00144) | nucleic acid binding (PC00171) |
| membrane traffic protein (PC00150) | oxidoreductase (PC00176) |
| nucleic acid binding (PC00171) | signaling molecule (PC00207) |
| oxidoreductase (PC00176) | storage protein (PC00210) |
| receptor (PC00197) | transcription factor (PC00218) |
| signaling molecule (PC00207) | transfer/carrier protein (PC00219) |
| transcription factor (PC00218) | transferase (PC00220) |
| transfer/carrier protein (PC00219) | transporter (PC00227) |
| transferase (PC00220) | |
| transmembrane receptor regulatory/ada protein (PC00226) | |
| transporter (PC00227) | |

Fig.6B

A
PANTHER Pathway
Total #Genes: 88 Total# pathway hits: 19
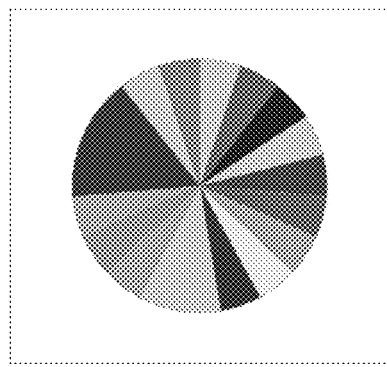
B
PANTHER Pathway
Level 1: Cholesterol biosynthesis (P00014)
Total #Genes: 94 Total# pathway hits: 21
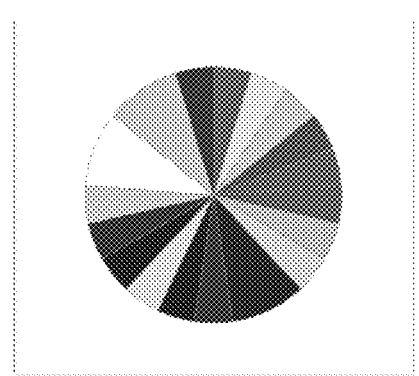
Fig. 7A

| | |
|---|---|
| ATP synthesis (P02721) | 5-Hydroxytryptamine degradation (P04372) |
| Apoptosis signaling pathway (P00006) | Ascorbate degradation (P02729) |
| CCKR signaling map (P06959) | Cell cycle (P00013) |
| Cell cycle (P00013) | Cholesterol biosynthesis (P00014) |
| Circadian clock system (P00015) | Coenzyme A biosynthesis (P02736) |
| Coenzyme A biosynthesis (P02736) | Cytoskeletal regulation by Rho GTPase (P00016) |
| EGF receptor signaling pathway (P00018) | DNA replication (P00017) |
| Gonadotropin-releasing hormone receptor pathway (P06664) | General transcription by RNA polymerase I (P00022) |
| Hedgehog signaling pathway (P00025) | General transcription regulation (P00023) |
| Parkinson disease (P00049) | Heme biosynthesis (P02746) |
| Pentose phosphate pathway (P02762) | Histidine biosynthesis (P02747) |
| Salvage pyrimidine ribonucleotides (P02775) | Inflammation mediated by chemokine and cytokine signaling pathway (P00031) |
| Toll receptor signaling pathway (P00054) | PDGF signaling pathway (P00047) |
| Ubiquitin proteasome pathway (P00060) | Pantothenate biosynthesis (P02761) |
| Wnt signaling pathway (P00057) | Parkinson disease (P00049) |
| p53 pathway by glucose deprivation (P04397) | Proline biosynthesis (P02768) |
| | Transcription regulation by bZIP transcription factor (P00055) |
| | Ubiquitin proteasome pathway (P00060) |

Fig. 7B

O-antigen biosynthesis (P02757)

Peptidoglycan biosynthesis (P02763)

Phenylalanine biosynthesis (P02765)

Proline biosynthesis (P02768)

Pyrimidine Metabolism (P02771)

Pyruvate metabolism (P02772)

Serine glycine biosynthesis (P02776)

TCA cycle (P00051)

Tetrahydrofolate biosynthesis (P02742)

Tryptophan biosynthesis (P02783)

Fig. 11B

PANTHER Pathway
Total #Genes: 72 Total# pathway hits: 43

▫ cytoskeletal protein (PC00085)

▪ enzyme modulator (PC00095)

▫ hydrolase (PC00121)

▪ isomerase (PC00135)

▪ lyase (PC00144)

▪ nucleic acid binding (PC00171)

oxidoreductase (PC00176)

▪ transcription factor (PC00218)

transferase (PC00220)

▪ transporter (PC00227)

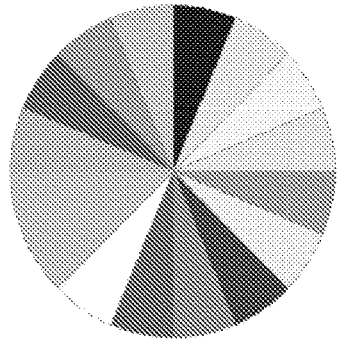

PANTHER Pathway

Total #Genes: 72

Total# pathway hits: 16

*Fig. 13*

- Arginine biosynthesis (P02728)
- Ascorbate degradation (P02729)
- Chorismate biosynthesis (P02734)
- De novo pyrimidine deoxyribonucleotide biosynthesis (P02739)
- Flavin biosynthesis (P02741)
- Formyltetrahydroformate biosynthesis (P02743)
- Histidine biosynthesis (P02747)
- Isoleucine biosynthesis (P02748)
- Mannose metabolism (P02752)
- N-acetylglucosamine metabolism (P02756)
- O-antigen biosynthesis (P02757)
- Pentose phosphate pathway (P02762)
- Peptidoglycan biosynthesis (P02763)
- Tetrahydrofolate biosynthesis (P02742)
- Wnt signaling pathway (P00057)

PANTHER Pathway

Total #Genes: 106 Total# pathway hits: 22

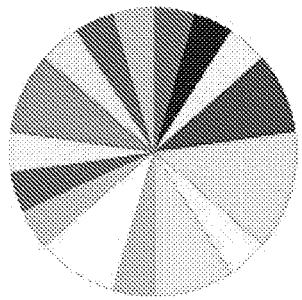

*Fig. 18*

5-Hydroxytryptamine degredation (P04372)

Arginine biosynthesis (P02728)

Chorismate biosynthesis (P02734)

De novo purine biosynthesis (P02737)

De novo pyrimidine deoxyribonucleotide biosynthesis (P0273)

De novo pyrimidine ribonucleotides biosythesis (P02740)

Formyltetrahydroformate biosynthesis (P02743)

Methionine biosynthesis (P02753)

N-acetylglucosamine metabolism (P02756)

O-antigen biosynthesis (P02757)

Peptidoglycan biosynthesis (P02763)

Pyridoxal phosphate salvage pathway (P02770)

Tetrahydrofolate biosynthesis (P02742)

Thiamin biosynthesis (P02779)

Vitamin B6 metabolism (P02787)

METHODS FOR MODULATING PROTEIN EXPRESSION IN MICROORGANISMS

CROSS-REFERENCE TO RELATED APPLICATIONS

This application is continuation-in-part of PCT International Application No. PCT/IL2017/051192 having International Filing Date of Nov. 1, 2017, which claims priority to U.S. Provisional Patent Application No. 62/415,517 filed Nov. 1, 2016. The content of these applications are both incorporated by reference in their entirety.

FIELD OF THE INVENTION

The invention relates to the field of non-thermal plasma technology and application. More particularly, the invention relates to means and methods for modulating protein expression, induction of proteins 'de-novo' and modulating biological pathways in microorganisms.

BACKGROUND OF THE INVENTION

Proteins are complex "molecular machines", the "engines of biological systems" that control our most vital cellular functions. Proteins are the main structural elements in cells and participate in nearly all cellular activities. Undeniably, proteins, the building materials of living cells, which are found within cells and cell membranes, are the most abundant and functionally diverse of all macromolecules. Human cells produce thousands of proteins that combine in highly complex physiological networks to perform precise actions through a wide variety of functions. They catalyze metabolic reactions, serve as structural components of biological assemblies, and are responsible for inter- and intracellular interactions and cell signaling events critical to life. Furthermore, all major cell processes are seen to involve the flow of information within the cell and organism through protein pathways and networks.

Proteins are also engaged in various cell functions and activities such as folding, assembly, disassembly, and trafficking through the subcellular compartments inside and outside the cell. Since they are responsible for the main cellular functions of cell growth, cell differentiation, and cell proliferation and death, protein dysfunction is responsible for many diseases, apparently due to errors relating to protein structure, function, and pathway/network-based interaction. In other words, deficiencies in the production of certain proteins or the synthesis of mutant, non-functional versions of biologically relevant proteins usually underlie pathologies ranging from mild to severe. For example, there is a wide variety of diseases known as protein conformational diseases which include neurodegenerative diseases, cancer, immunological, and metabolic diseases. When proteins mis-fold and if defensive homeostasis mechanisms cannot sustain protein-folding burdens, devastating human diseases ensue. More specifically, inaccurate protein modifications eventually manifest as loss-of-function diseases due to flawed protein folding, degradation, and localization. Among such diseases are Gaucher's disease, the most common lysosomal storage diseases, and cystic fibrosis. Diseases stemming from gain-of-toxic-function are mainly due to mutations causing toxic novel function and protein oxidation leading to increased protein hydrophobicity. These protein defects often result in toxic aggregates, dominant-negative mutations, amyloid accumulation diseases such as Huntington's disease (HD), Alzheimer's disease (AD), amyotrophic lateral sclerosis (ALS), respiratory distress syndrome, muscular dystrophy, cataractogenesis, rheumatoid arthritis, progeria, and Werner's syndrom. Dysfunction in proteins caused by abnormal amino acid sequences or the lack of a certain protein often leads to serious pathologies including diabetes, thalassaemia, impaired blood clotting, and other pathologies.

Since proteins are the engines for biological systems, nearly all pharmaceuticals act upon proteins and proteins themselves are increasingly used therapeutically. Protein deficiency treatment in humans includes prompt or repeated clinical administration of the missing protein until functional concentrations are achieved. This means that therapeutic proteins replace essential proteins that patients' body cannot produce by itself or it is under-produced by the body. Other therapeutic proteins supplement inadequate protein function with varying effects. Treatments can include supplementing the therapeutic proteins in antibodies to support the immune response or deactivating harmful substances in the body. This makes them valuable for treating autoimmune illnesses such as rheumatoid arthritis and Crohn's disease, which are triggered by immune system overreaction.

Although many human proteins have significant pharmaceutical value, they are difficult to extract from their natural sources. As a result biopharmaceuticals based on recombinant proteins have been developed which use genetic engineering technologies with pre-determined microbial cells. Indeed, advances in fermentation and engineering technologies have produced proteins for biopharmaceutical and other industrial purposes-mainly exploratory research, drug discovery initiatives, and biopharmaceuticals production. So far more than 200 recombinant protein-based biopharmaceuticals have been approved for human therapeutic and/or diagnostic use and more than 350 are in late-stage clinical trials. Recent advances increasingly stem from comprehensive genetic tools combined with a better understanding of the cellular nature of microorganisms. Consequently, insect cell lines, yeast, and fungi have become alternative candidates for producing glycosylated therapeutic proteins previously only produced in mammalian hosts due to the benefits of productivity and consistency in protein glycosylation structures.

Constant improvements and developments in genetic engineering technologies, especially systems metabolic engineering harnessing the concepts and techniques of systems biology, synthetic biology, and evolutionary engineering at the systems level, has facilitated more efficient protein production and a larger set of recombinant proteins. For example, metabolic engineering is used for producing drugs by effecting gene expression.

Therefore recombinant proteins play an important role in the pharmaceutical industry and an increasing number of the proteins are complex proteins, such as integral membrane proteins, antibodies, vaccines, and hormones, which are expected to treat currently untreatable diseases. Another important advantage of microbial expression systems for producing recombinant proteins is that the process time from gene to product is less than in mammalian cell cultures.

Protein engineering technologies can require overcoming limitations or restrictive conditions for efficient recombinant protein production. These restrictive conditions include: activation of cell stress response or causing metabolic stress following abuse of cellular systems for protein production; over-expression of a heterologous protein; abundance of misfolded polypeptides which fail to reach their native conformation; environmental stresses imposed by the cultivation conditions which largely depend on the design of the fermentation strategy; proteolytic instability; bottlenecks in in-vivo protein folding; unconventional or lack of post-translational modifications], and poor solubility.

In order to overcome such restrictive conditions affecting protein production, several processes and engineering strategies have been suggested, in particular for engineering yeasts. These processes include: engineering a non-activating unfolded protein response in order to produce the highest levels of heterologous protein production; generating specific strains of microbial species adapted to efficient protein production; modulating the various components of cellular networks and cell performance by introducing new pathways into organisms with high metabolic activity: increasing or deleting specific activities of perceived limiting enzymes or deleting endogenous enzymes (such as glucosides) for the production of desired enzymes (such as flavonoid glucosides); creating novel and fine-controlled metabolic and regulatory circuits which maximize metabolic fluxes in the desired products within the strain being developed to enhance innate metabolic capabilities or reach new capabilities in the production of target compounds; changing the external environment of bioprocesses in order to enhance growth, production, and productivity by providing optimum operating conditions; overexpressing molecular chaperones and other folding related proteins, or deleting deleterious pathways that may lead to misfolding, mistargeting, or degradation.

Undoubtedly the production of recombinant proteins in microbial systems has revolutionized the medical field and challenged the biotechnological field. Yet, several important drawbacks and limitations still remain to be approached for effectively and efficiently produce valuable proteins for medical and industrial purposes and more efficiently enrich a desired set of proteins.

For example, the choice of a host cell to provide the protein synthesis machinery needed to produce the desired protein depends on several factors. These factors include: the effects of genetic manipulation on growth and "unrelated" systems in the host; ease of cultivation and growth characteristics; ease of genetic manipulation and availability of molecular tools; ability to achieve post-translational modification (e.g., glycosylation patterns, disulfide bond formation), downstream processing, and regulatory functions.

It can be inferred from the above that despite major successes in producing recombinant proteins for the medical and industrial fields, the list of reported unsuccessful attempts to do so is disappointingly long and therefore there is still a need to new technologies to overcome the current traditional recombinant protein methodology disadvantages, obviously depending on the recombinant protein sought. Various suggestions have been made for extending the knowledge base for future rational engineering strategies using system biology. These suggestions emphasize the need to consider the information flow within the cell and organism through protein pathways and networks and the entire interconnecting circuits of proteins—both inside and outside a cell—as they coalesce following stimulus and disperse when the stimulus is removed.

Non-thermal plasma (NTP) systems have been emerging as useful tools for various clinical applications. Physical plasma is known to catalyze biochemical activities when applied on tissue and is able to regulate cellular processes such as proliferation, differentiation, and apoptosis. This, in part, is due to the reactive oxygen and nitrogen species (ROS and RNS) generated by application of non-thermal plasma. Most of the plasma research has been performed in vitro or ex vivo, which has led to investigation of potential applications such as disinfection of surfaces, promotion of hemostasis, enhancement of tissue regeneration, acceleration of wound healing, and for anti-cancer therapy. However, there has not been an extensive characterization of non-thermal plasma in in vivo model organisms. Furthermore, the exposure to NTP was not correlated with an effect on specific proteins or protein pathways or protein profile expression.

U.S. Pat. No. 8,725,248 to Gutsol et al. May 13, 2014 discloses that non-thermal plasma help establish mechanical connection between tissue parts through several possible mechanisms including plasma-chemical modification of biopolymers on the surfaces of tissue and formation of fiber material during blood coagulation. A barrier insulator or semiconductor is placed between the electrode and tissue resulting in limiting the current through plasma and through tissue to minimize tissue heating. The disclosed non-thermal plasma treatment can be employed to promote coagulation of blood, sterilization, disinfection, re-connection of tissue, and treatment of tissue disorders without causing significant thermal tissue damage.

It is further reported in U.S. Pat. No. 8,725,248 that the non-thermal plasma discharge may be employed to inactivate bacteria, viruses, micro-organisms, or destroying certain proteins that may exist on or within the tissue. Alternatively, the non-thermal plasma discharge may be employed for the purpose of destroying certain cells in the tissue, particularly cells located in a surface layer of the tissue.

U.S. Pat. No. 8,896,211 to Ish-Yamini Tomer, et al. Nov. 25, 2014, discloses a system for generating modified plasma. However, it does not teach how to achieve a biological effect on modulation of protein profile of living organisms. Furthermore it does not teach 'de-novo' production, generation or induction of proteins.

In patent KR101773846, the gas supply of the non-thermal plasma on the surface has dermatitis sterilization effect.

U.S. Pat. No. 9,295,280 to Jacofsky, et al. Mar. 29, 2016 discloses a cold plasma device for killing or reducing a microbiological pathogen, or denaturing a protein in food.

U.S. Pat. No. 9,521,736 to Jacofsky, et al. Dec. 13, 2016 discloses a method and device to apply a cold plasma to a substance at a treatment surface of a patient to cause electroporation of the substance into cells of the patient. The substance can be previously applied to the treatment surface. Alternatively, the substance can be placed in a foam-like material within a tip that passes the cold plasma from the cold plasma device to the treatment area.

In view of the above, there is still a long felt and unmet need to provide systems and methods for modulating protein production as well as 'de-novo' production, generation or induction of proteins in vivo which are not based on genetic engineering processes.

SUMMARY OF THE INVENTION

The present invention relates to the field of non-thermal plasma technology and application. In particular, the invention relates to novel means and methods for modulating protein expression and production, generation or induction of proteins 'de-novo', and biological pathways in microorganisms.

It is thus one object of the present invention to disclose a method for modulating protein expression in targeted microorganisms as well as production, generation or induction of proteins 'de-novo', the method comprises steps of: (a)

providing a system comprising: i. a plasma discharge source for discharging plasma to the microorganisms, the plasma comprising about 70-98% Argon, about 6-9% Nitrogen and about 1.5-2.5% Oxygen by % (wt.); the plasma discharge electric field is in the range of 200-500 v/m; ii. a plasma modifying mechanism comprising (1) at least one magnetic material, and at least one piezoelectric material, and (2) at least one optical crystal material, the plasma modifying mechanism providing modified plasma output having frequencies in the range of about 3 KHz to about 30 KHz; (b) providing target microorganisms; (c) providing instructions for the plasma source to discharge the plasma in a predetermined pulsed profile characterized by pulse cycle duration in the range of 0.1-2.1 min, each pulse cycle comprises a series of 6-57 "on pulses" and 3-44 pauses, and the number of pulse cycles is in the range of 3 to 20, the profile effective in modulating the protein expression as well as production, generation or induction of proteins 'de-novo', in said targeted microorganisms exposed to said modified plasma output as compared to control microorganisms not exposed to said modified plasma output.

It is another object of the present invention to disclose the method as defined above, wherein the distance between said plasma source and said targeted microorganisms is in the range of about 2 cm to about 10 cm, preferably about 3 cm to about 7 cm.

It is another object of the present invention to disclose the method as defined in any of the above, wherein said method is effective in modulation of said protein expression in said targeted microorganisms as well as production, generation or induction of proteins 'de-novo' between 0-24 hours following said exposure to said modified plasma output, preferably between about 0-6 hours following said exposure to said modified plasma output.

It is another object of the present invention to disclose the method as defined in any of the above, wherein said modified plasma output is effective in a depth of at least about 6 cm.

It is another object of the present invention to disclose the method as defined in any of the above, wherein said microorganisms are in a substrate.

It is another object of the present invention to disclose the method as defined in any of the above, wherein said substrate is selected from the group consisting of: food, liquid, beverage, suspension, biological culture, biological fluid, medium, growth medium, emulsion, biological tissue, plant, fluid, soil, minerals, media, gas, gas and liquid mixtures, gas mixtures, cells, tissue culture, organs and any combination thereof.

It is another object of the present invention to disclose the method as defined in any of the above, wherein said microorganisms are selected from the group consisting of yeast, bacteria, archaea, algae, fungi, protozoa, virus, spores, hypha, prion, *Candida*, corynebacteria, aerobic bacteria, anaerobic bacteria, *bacillus subtillis Listeria monocytogenes, Escherichia coli (E. coli), Salmonella*, bacteria of the Enterobacteriaceae family, bacteria of the Listeriaceae family, gram positive bacteria, gram negative bacteria, *Staphylococcus aureus, Pseudomonas aeruginosa, Staphylococcus epidermidis, Staphylococcus haemolyticus, Enterococcus faecalis*, Clostridiaceae family, *Clostridium*, corynebacteria, actinobacteria and any combination thereof.

It is another object of the present invention to disclose the method as defined in any of the above, wherein said modulation of protein expression and production, generation or induction of proteins 'de-novo' comprises induction, upregulation and/or downregulation of protein expression in said targeted microorganism as compared to said control microorganisms.

It is another object of the present invention to disclose the method as defined in any of the above, wherein said method is effective in modulation of at least one of: protein expression profile, protein class profile, protein pathways profile, protein isoelectric properties, protein molecular weight properties, protein modification properties, protein solubilization properties, and any combination thereof in said targeted microorganisms as compared to said control microorganisms.

It is another object of the present invention to disclose the method as defined in any of the above, wherein said method is effective in modulation of proteins and production or generation or induction of proteins 'de-novo' selected from the group consisting of pellet proteins, supernatant proteins, intracellular proteins, extracellular proteins and any combination thereof in said targeted microorganisms as compared to said control microorganisms.

It is another object of the present invention to disclose the method as defined in any of the above, wherein said method is effective in induction of yeast proteins belonging to a protein class selected from the group consisting of: calcium-binding protein (PC00060), chaperone (PC00072), cytoskeletal protein (PC00085), enzyme modulator (PC00095), hydrolase (PC00121), ligase (PC00142), lyase (PC00144), membrane traffic protein (PC00150), nucleic acid binding (PC00171), oxidoreductase (PC00176), receptor (PC00197) signaling molecule (PC00207), structural protein (PC00211), transcription factor (PC00218), transfer/carrier protein (PC00219), transferase (PC00220), transmembrane receptor regulatory/adaptor protein (PC00226), transporter (PC00227), calcium-binding protein (PC00060), cell adhesion molecule (PC00069), chaperone (PC00072) enzyme modulator (PC00095), hydrolase (PC00121), ligase (PC00142), lyase (PC00144) membrane traffic protein (PC00150), nucleic acid binding (PC00171), oxidoreductase (PC00176), signaling molecule (PC00207), transporter (PC00227) and any combination thereof, following exposure of said yeast to said modified plasma output for about 2.8 min as compared to non-exposed control yeast.

It is another object of the present invention to disclose the method as defined in any of the above, wherein said method is effective in induction of yeast proteins belonging to a protein class selected from the group consisting of calcium-binding protein (PC00060), chaperone (PC00072), cytoskeletal protein (PC00085), enzyme modulator (PC00095), extracellular matrix protein (PC00102), hydrolase (PC00121) isomerase (PC00135), ligase (PC00142), lyase (PC00144), membrane traffic protein (PC00150), nucleic acid binding (PC00171), oxidoreductase (PC00176), receptor (PC00197), signaling molecule (PC00207), transcription factor (PC00218), transfer/carrier protein (PC00219), transferase (PC00220), transmembrane receptor regulatory/adaptor protein (PC00226), transporter (PC00227) and nay combination thereof, following exposure of said yeast to said modified plasma output for about 4.9 min as compared to non-exposed control yeast.

It is another object of the present invention to disclose the method as defined in any of the above, wherein said method is effective in induction of yeast proteins belonging to a protein pathway selected from the group consisting of: Angiogenesis (P00005), Cell cycle (P00013), Cholesterol biosynthesis (P00014), Cytoskeletal regulation by Rho GTPase (P00016), DNA replication (P00017), Huntington disease (P00029), Methionine biosynthesis (P02753) PDGF signaling pathway (P00047), Purine metabolism (P02769), Tryptophan biosynthesis (P02783), Ubiquitin proteasome pathway (P00060), VEGF signaling pathway (P00056), mRNA splicing (P00058), Apoptosis signaling pathway (P00006), DNA replication (P00017), General transcription regulation (P00023), Gonadotropin-releasing hormone receptor pathway (P06664), Heme biosynthesis (P02746), Methionine biosynthesis (P02753), Parkinson disease (P00049), Pyruvate metabolism (P02772), Salvage pyrimidine ribonucleotides (P02775), Transcription regulation by bZIP transcription factor (P00055), Ubiquitin proteasome pathway (P00060), Wnt signaling pathway (P00057) and any combination thereof, following exposure of said yeast to said modified plasma output for about 2.8 min as compared to non-exposed control yeast.

It is another object of the present invention to disclose the method as defined in any of the above, wherein said method is effective in induction of yeast proteins belonging to a protein pathway selected from the group consisting of: ATP synthesis (P02721), Apoptosis signaling pathway (P00006), CCKR signaling map (P06959), Cell cycle (P00013), Circadian clock system (P00015), Coenzyme A biosynthesis (P02736), EGF receptor signaling pathway (P00018), Gonadotropin-releasing hormone receptor pathway (P06664), Hedgehog signaling pathway (P00025), Parkinson disease (P00049), Pentose phosphate pathway (P02762) Salvage pyrimidine ribonucleotides (P02775), Toll receptor signaling pathway (P00054), Ubiquitin proteasome pathway (P00060), Wnt signaling pathway (P00057) p53 pathway by glucose deprivation (P04397) and any combination thereof, following exposure of said yeast to said modified plasma output for about 4.9 min as compared to non-exposed control yeast.

It is another object of the present invention to disclose the method as defined in any of the above, wherein said method is effective in induction of yeast proteins selected from the group consisting of: P15624 Phenylalanine-tRNA ligase beta subunit, Q01939 26S protease regulatory subunit 8 homolog, P21242 Probable proteasome subunit alpha type-7, Q12018 Cell division control protein 53, P25375 Saccharolysin Could be involved in late stage of protein degradation, P32477 Glutamate—cysteine ligase, Q6Q560 Protein ISD1, P36528 54S ribosomal protein L17, mitochondrial Q08548 Lysophospholipid acyltransferase, P20484 Protein MAK11, Q12396 Protein EMP46, P53849 Zinc finger protein GIS2, O13297 mRNA-capping enzyme subunit beta, POCH09 Ubiquitin-60S ribosomal protein L40, Q99337 Transposon Ty1-NL2 Gag-Pol polyprotein, P36047 phosphatase 1 regulatory subunit SDS22, P39077 T complex protein 1 subunit gamma, P53549 26S protease subunit RPT4, P48510 Ubiquitin domain-containing protein DSK2, P25303 DnaJ-related protein SCJ1, P53192 Golgi to ER traffic protein 1, P53910 Uncharacterized protein YNL140C, Q01329 Pre-tRNA-processing protein PTA1, P04803 Tryptophan—tRNA ligase mitochondrial, Q03020 Iron sulfur cluster assembly protein 1 mitochondrial, Q08693 Putative zinc metalloprotease TRE2, P32378 4-hydroxybenzoate polyprenyltransferase, mitochondrial, P38783 Protein FYV4 mitochondrial, Q12743—DER1-like family member protein 1—Gene DFM1, Q04401 Succinate dehydrogenase assembly factor 3, mitochondrial—Gene SDH7, P52871 Protein transport protein SBH2—Gene SBH2, Q04235 tRNA wybutosine-synthesizing protein 2—Gene TRM12, P41058 40S ribosomal protein S29-B—Gene RPS29B, P04803 Tryptophan—tRNA ligase, mitochondrial—Gene MSW1, P40312 Cytochrome b5—Gene CYBS, Q03201 37S ribosomal protein S10, mitochondrial—Gene RSM10, P38840 Aromatic amino acid aminotransferase 2—Gene ARO9, P53220 Mitochondrial import inner membrane translocase subunit TIM21—Gene TIM21, Q04170 Uncharacterized protein YDR391C—Gene YDR391C, Q03281 Inner nuclear membrane protein HEH2—Gene HEH2, P39010 Palmitoyltransferase AKR1—Gene AKR1, Q08926 ULP1-interacting protein 4—Gene UIP4, Q03280 E3 ubiquitin-protein ligase TOM1—Gene TOM1, Q12033 pH-response regulator protein palA/RIM20—Gene RIM20, Q05949 Protein BUR2—Gene BUR2, Q12152 Putative serine/threonine-protein kinase YPL150W—Gene YPL150W, P06839 DNA repair helicase RAD3—Gene RAD3, P22204 Cell cycle protein kinase DBF2—Gene DBF2, Q07442 Bromodomain-containing factor 2—Gene BDF2, P40151 DNA-dependent ATPase MGS 1—Gene MGS 1, P53204 Nicotinamide/nicotinic acid mononucleotide adenylyltransferase 2—Gene NMA2, P16965 ATPase-stabilizing factor 15 kDa protein—Gene STF2, P36084 Splicing factor MUD2—Gene MUD2, P33893 Glutamyl-tRNA(Gln) amidotransferase subunit B, mitochondrial—Gene PET 112, Q12324 Calcium channel YVC1—Gene YVC1, Q02981 ABC1 family protein YPL109C, mitochondrial—Gene YPL109C, P38243 Uncharacterized protein YBR071W, P38782 Mediator of RNA polymerase II transcription subunit 6—Gene MED6, P38149 Probable di- and tripeptidase DUG2—Gene DUG2, P53733 37S ribosomal protein S19, mitochondrial—Gene RSM19, P40079 U3 small nucleolar ribonucleoprotein protein LCP5—Gene LCP5, Q92331 Vacuolar protein sorting-associated protein 5—Gene VPS5, P38719 ATP-dependent RNA helicase DBP8—Gene DBP8, P53336 Putative methyltransferase YGR283C—Gene YGR283C, P36036 RNA annealing protein YRA2—Gene YRA2, POC5N3 Uncharacterized protein YGL041W-A, mitochondrial—Gene YGL041W-A, Q12251 Uncharacterized mitochondrial carrier YPR011C, P38087 Carrier protein YMC2, mitochondrial—GeneYMC2, P36104 COMPASS component SWD2—Gene SWD2, P46676 Suppressor of marl-1 protein—Gene SUM1, P53170 [Pyruvate dehydrogenase (acetyl-transferring)] kinase 2, mitochondrial—Gene PKP2, P53972 25S rRNA (cytosine(2278)-C(5))-methyltransferase—Gene RCM1, P40038 PHO85 cyclin-6—Gene PCL6, P40533 Protein TED1—Gene TED1, Q03441 Sporulation protein RMD1—Gene RMD1, P38737 Proteasome component ECM29—Gene ECM29, P21825 Translocation protein SEC62—Gene SEC62, P47822 Mediator of RNA polymerase II transcription subunit 21—Gene SRB7, Q12392 Transposon Ty2-DR1 Gag polyprotein—Gene TY2A-DR1 and any combination thereof, immediately following exposure of said yeast to said modified plasma output for about 2.8 min as compared to non-exposed control yeast.

It is another object of the present invention to disclose the method as defined in any of the above, wherein said method is effective in induction of yeast proteins selected from the group consisting of: P18562 Uracil phosphoribosyltransferase, P15424 ATP-dependent RNA helicase MSS116 mitochondrial, Q02204 54S ribosomal protein L13 mitochondrial, Q04689 Altered inheritance of mitochondria protein 32, Q02792 5'-3' exoribonuclease 2, Q2V2Q1 Antisense of depressing factor protein 1, P53267 DASH complex subunit DAM1, Q12082 Uncharacterized protein YDL157C, mitochondrial, Q07793 Transposon Ty1-DR4 Gag-Pol polyprotein, Q12427 Protein STB3, Q99359, Protein RAD61P33767 Dolichyl-diphosphooligosaccharide-protein glycosyltransferase subunit WBP1, P40335 Carboxypeptidase Y-deficient protein 8, Q01163 37S ribosomal protein S23 mitochondrial, P38166 Protein transport protein SFT2, P53101 Cystathionine beta-lyase, P32318 Thiamine thiazole synthase, P53309 Clathrin coat assembly protein AP180B, P32774 Transcription initiation factor IIA subunit 2, P21657 Transcriptional activator protein DAL81, P50088 Stationary phase gene 1 protein, Q06497 Peroxisomal adenine nucleotide transporter 1, P52870 Protein transport protein SBH1, Q08492 Bud site selection protein 21, P39939 40S ribosomal protein S26-B, P14359 Protein SNA3, Q08269 Magnesium transporter ALR1, P06774 Transcriptional activator HAP2, P39001 Transcriptional regulatory protein UME6, P02293 Histone H2B.1, P26570 Serine/threonine-protein phosphatase PP-Z1, P32567 Phosphatidic acid phosphohydrolase 1, P32259 Mediator of RNA polymerase II transcription subunit 16—Gene SIN4, Q08960 S-adenosyl-L-methionine-dependent tRNA 4-demethylwyosine synthase—Gene TYW1, P53086 Kinesin-like protein KIP3—Gene KIP3, P35184 Ribosome assembly protein SQT1—Gene SQT1, P36024 Phosphopantothenoylcysteine decarboxylase subunit SIS2—Gene SIS2, P38929 Calcium-transporting ATPase 2—Gene PMC1, Q04341 Mitochondrial intermembrane space cysteine motif-containing protein MIX14—Gene MIX14, P18900 Hexaprenyl pyrophosphate synthase, mitochondrial—Gene COQ1, Q9URQ5 High temperature lethal protein 1—Gene HTL1, P26370 Transcriptional activator protein UGA3—Gene UGA3, P39965 Probable proline—tRNA ligase, mitochondrial—Gene AIM10, P10363 DNA primase small subunit—Gene PRI1, P40154 Ino eighty subunit 2—Gene IES2, Q02793 Antiviral protein SKI8—Gene SKI8, P39524 Probable phospholipid-transporting ATPase DRS2—Gene DRS2, P53824 Probable pyridoxal 5'-phosphate synthase subunit SNZ2—Gene SNZ2, Q12161 RING finger protein PSH1—Gene PSH1, Q12505 Serine/threonine-protein kinase SKS1—Gene SKS1, Q12753 Transcriptional activator HAA1—Gene HAA1, P40955 Chitin biosynthesis protein CHS6—Gene CHS6, P32618 Uncharacterized protein YEL043W, P53849 Zinc finger protein GIS2—Gene GIS2, P32504 Centromere DNA-binding protein complex CBF3 subunit A—Gene CBF2, P38604 Lanosterol synthase—Gene ERG7, P53154 Glycerol uptake protein 1—Gene GUP1, Q02260 Small nuclear ribonucleoprotein Sm D1—Gene SMD1, P32643 Trans-aconitate 3-methyltransferase—Gene TMT1, Q99207 Nucleolar complex protein 14—Gene NOP14, P49956 Chromosome transmission fidelity protein 18—Gene CTF 18, P12868 E3 ubiquitin-protein ligase PEPS—Gene PEPS, Q12470 Transposon Ty1-NL2 Gag polyprotein—Gene TY1A-NL2, Q12260 Transposon Ty2-B Gag polyprotein—Gene TY2B-B, and any combination thereof, 30 minutes following exposure of said yeast to said modified plasma output for about 2.8 min as compared to non-exposed control yeast.

It is another object of the present invention to disclose the method as defined in any of the above, wherein said method is effective in induction of yeast proteins selected from the group consisting of: P11484 Heat shock protein SSB1, Q05567 Sphingosine-1-phosphate lyase, P34223 UBX domain-containing protein 1, Q06010 A-factor-processing enzyme, Q07651 SUR7 family protein FMP45, Q07979 Chromatin structure-remodeling complex protein RSC58, Q03774 tRNA (guanine-N(7)-)-methyltransferase non-catalytic subunit TRM82, P33332 Exocyst complex component SEC3, P33417 Intrastrand cross-link recognition protein, P38837 Protein NSG1, O75012 37S ribosomal protein MRP10 mitochondrial, P38068 Monothiol glutaredoxin-7, P11792 Serine/threonine-protein kinase SCH9, Q03855 Transposon Ty1-DR1 Gag-Pol polyprotein, Q7LHD1 Putative covalently bound cell wall protein 22—Gene CCW22, P53341 Alpha-glucosidase MAL12—Gene MAL12, P53144 HD domain-containing protein YGL101W—Gene YGL101W, P23493 Mitochondrial biogenesis regulation protein 1—Gene MBR1, Q06608 Pyridoxamine 5'-phosphate oxidase homolog—Gene YPR172W, P40007 Nucleolar protein 16—Gene NOP16, Q08492 Bud site selection protein 21—Gene BUD21, P53980 Uncharacterized protein YNL011C—Gene BUD21, P25358 Elongation of fatty acids protein 2—Gene ELO2, Q12467 MIOREX complex component 4, Q03782 56 kDa U1 small nuclear ribonucleoprotein component—Gene SNU56, P38829 MIP18 family protein YHR122W—Gene YHR122W, Q08237 Protein putative 3'-5' exonuclease—REX4/YOL080C Protein, P39678 Transcription factor MBP1—Gene MBP1, P53267 DASH complex subunit DAM1—Gene DAM1, P36081 Uncharacterized protein YKL077W—Gene YKL077W, Q04533 Putative cystathionine gamma-synthase YML082W—Gene YML082W, Q12321 Mediator of RNA polymerase II transcription subunit 1—Gene MED1, P40368 Nucleoporin NUP82—Gene NUP82, P36014 Glutathione peroxidase 1—Gene GPX1, Q06682 UBX domain-containing protein 5—Gene UBX5, P40555 Probable 26S proteasome regulatory subunit p27—Gene NAS2, Q03266 Aminodeoxychorismate lyase—Gene ABZ2, Q06214 WD repeat-containing protein JIP5 or Jumonji domain-interacting protein 5—Gene JIP5, P32767 Importin beta-like protein KAP122—Gene KAP122, P32908 Structural maintenance of chromosomes protein 1—Gene SMC1, P81451 ATP synthase subunit K, mitochondrial—Gene ATP19, P48524 Ubiquitin ligase-binding protein BUL1—Gene BUL1, P22434 3',5'-cyclic-nucleotide phosphodiesterase 1—Gene PDE1, Q92392 Transposon Ty1-OL Gag polyprotein—Gene TY1B-H, Q05518 Protein PAL1—Gene PAL1, P38874 Elongator complex protein 5—Gene IKI1, P04911 Histone H2A.1 (dna repair)—Gene Gene HTA1, P20676 Nucleoporin NUP1—Gene NUP1, P38994 Probable phosphatidylinositol 4-phosphate 5-kinase MSS4—Gene MSS4, P53072 tRNA acetyltransferase TAN1—Gene TAN1, P25568 Autophagy-related protein 22—Gene ATG22, Q02100 CRE-binding bZIP protein SKO1—Gene SKO1, P35182 Protein phosphatase 2C homolog 1—Gene PTC1, P53067 Importin subunit beta-5—Gene KAP114, P06778 DNA repair and recombination protein RAD52—Gene RAD52, P13711 Acyl-coenzyme A oxidase—Gene POX1, Q04471 Putative peptidase YMR114C—Gene YMR114C, P53195 Conserved oligomeric Golgi complex subunit 7—Gene COG7, P34239 Protein LST4—Gene LST4, P26570 Serine/threonine-protein phosphatase PP-Z1—Gene PPZ1, Q02647 Dynein light chain 1, cytoplasmic—Gene DYN2, P19263 Mediator of RNA polymerase II transcription subunit 14—Gene RGR1, Q12485 Transposon Ty1-GR2 Gag polyprotein—Gene TY1A-GR2 and any combination thereof 1 hour following exposure of said yeast to said modified plasma output for about 2.8 min as compared to non-exposed control yeast.

It is another object of the present invention to disclose the method as defined in any of the above, wherein said method is effective in induction of yeast proteins selected from the group consisting of, Cytochrome c iso-1 CYC1_YEAST, Glycogen [starch] synthase isoform 2GYS2_YEAST, Acetolactate synthase small subunit, mitochondrial ILV6_YEAST, Mitochondrial distribution and morphology protein 38 MDM38_YEAST, Family of serine hydrolases 1 FSH1_YEAST, E3 ubiquitin-protein ligase RSP5 RSP5_YEAST, Protein translocation protein SEC63 SEC63_YEAST, 6-phosphogluconate dehydrogenase, decarboxylating 2 6PGD2_YEAST, 26S proteasome regulatory subunit RPN6 RPN6_YEAST, H/ACA ribonucleoprotein complex subunit 4CBF5_YEAST, Eukaryotic translation initiation factor 2 subunit beta IF2B_YEAST, 40S ribosomal protein S25-A RS25A_YEAST, Protein arginine N-methyltransferase SFM1 SFM1_YEAST, 60S ribosomal protein L6-B RL6B_YEAST, 60S ribosomal protein L34-A RL34A_YEAST, Coronin-like protein CORO_YEAST, Putative Xaa-Pro aminopeptidase FRA1 FRA1_YEAST, SNF 1 protein kinase subunit beta-2

SIP2_YEAST, Putative carboxymethylenebutenolidase DLHH_YEAST, Protein phosphatase 2C homolog 2 PP2C2_YEAST, Mitochondrial phosphate carrier protein 2 PIC2_YEAST, 60S ribosomal protein L16-A RL16A_YEAST, Protein SIP18 SIP18_YEAST, ATP synthase subunit H, mitochondrial ATP14_YEAST, Dolichyl-phosphate-mannose—protein mannosyltransferase 1PMT1_YEAST, Uncharacterized protein YFR016C YFI6_YEAST Sphingosine-1-phosphate lyase SGPL_YEAST, Mitochondrial outer membrane protein IML2 IML2_YEAS7, D-serine dehydratase DSD1_YEAST, Golgi to ER traffic protein 4 GET4_YEAST, Very long-chain fatty acid transport protein FAT1_YEAST, ADP-ribosylation factor GTPase-activating protein GLO3 GLO3_YEAST, Mitogen-activated protein kinase HOGiHOGI_YEAST, Succinate dehydrogenase assembly factor 4, mitochondrial SDHF4_YEAST, UPF0674 endoplasmic reticulum membrane protein YNR021W YN8B_YEAST, Mitochondrial genome maintenance protein MGM101, MG101_YEAST, Altered inheritance of mitochondria protein 46, mitochondrial AIM46_YEAS7, Cytochrome c oxidase protein 20, mitochondrial COX20_YEAST, Benzil reductase ((S)-benzoin forming) IRC24 BZRD_YEAST, Regulator of Ty1 transposition protein 102 RT102_YEAST, Vacuolar protein-sorting-associated protein 60 VPS60_YEAST, 3-hydroxyisobutyryl-CoA hydrolase, mitochondrial, HIBCH_YEAST, AP-1-like transcription factor YAP 1, YAPI_YEAST, Exosome complex component CSL4CSL4_YEAST, Uncharacterized protein YER152C YEY2_YEAST and any combination thereof, immediately following exposure of said yeast to said modified plasma output for about 4.9 min as compared to non-exposed control yeast.

It is another object of the present invention to disclose the method as defined in any of the above, wherein said method is effective in induction of yeast proteins selected from the group consisting of: 13 kDa ribonucleoprotein-associated protein SNU13_YEAST, Protease B inhibitor 1 IPB1_YEASX, Histone H2B.1 H2B1_ASHGO, Multisite-specific tRNA:(cytosine-C(5))-methyltransferase NCL1_YEAST, RNA polymerase II degradation factor 1 DEF1_YEAS2, Cytochrome c oxidase subunit 6A, mitochondrial COX13_YEAST, 3-ketoacyl-CoA thiolase, peroxisomal THIK_YEAST; Probable secreted beta-glucosidase SIM1 SIM1_YEAST, Mitochondrial import inner membrane translocase subunit TIM9 TIM9_YEAST, ATP-dependent (S)-NAD(P)H-hydrate dehydratase NNRD_YEAST, Ubiquitin-conjugating enzyme variant MMS2MMS2_YEAST, Covalently-linked cell wall protein 14 CCW14_YEAST; Protein phosphatase 1 regulatory subunit SDS22 SDS22_YEAST, DNA damage-inducible protein 1 DDIl_YEAST, Proteasome subunit beta type-4 PSB4_YEAST, Reticulon-like protein 2 RTN2_YEAST, ARS-binding factor 2, mitochondrial ABF2_YEAST; Histone chaperone ASF1 ASF1_YEAST, Ribosome biogenesis protein TSR1 TSR1_YEAST; Thioredoxin-3, mitochondrial TRX3_YEAST, C-8 sterol isomerase ERG2_YEAST, Uncharacterized protein YGR130C YG3A_YEAST, Uncharacterized phosphatase YNL010W YNBO_YEAST, Periodic tryptophan protein 1 PWP1_YEAST, Protein AIM2 AIM2_YEAST, RNA annealing protein YRA1 YRA1_YEAST, Kynureninase KYNU_YEAST, Signal transduction protein MDG1 MDG1_YEAS1, Phosphatidylinositol transfer protein CSR1 CSR1_YEAST, ER-derived vesicles protein ERV29 ERV29_YEAST, Biotin—protein ligase BPL1_YEAST, LOG family protein YJL055W YJF5_YEAST, 6-phosphogluconolactonase-like protein 2 SOL2_YEAST, Protein HRB 1HRB 1_YEAST, Uncharacterized protein YML079W YMH9_YEAST, Uncharacterized protein YOR389WYO389_YEAST, Casein kinase I homolog HRR25 HRR25_YEAST, GTP-binding protein YPT32/YPT11 YPT32_YEAST, Glucose-repressible alcohol dehydrogenase transcriptional effector CCR4_YEAST, 20S rRNA accumulation protein 4TSR4_YEAST, Cell wall mannoprotein CIS3 CIS3_YEAST, Phosphopantothenate—cysteine ligase CAB2 PPCS_YEAST, Uncharacterized protein YDR476CYD476_YEAST, Cruciform DNA-recognizing protein 1 CRP1_YEASB, Protein VHS2 VHS2_YEAST, Styryl dye vacuolar localization protein 3SVL3_YEAST, Iron transport multicopper oxidase FET3 FET3_YEAST, Nucleolar GTP-binding protein 1 NOGI_YEAST, Protein EAP1 EAP1_YEAST, U3 small nucleolar RNA-associated protein 25 UTP 25_YEAS1, GPN-loop GTPase 1

GPN1_YEAST, 5-oxoprolinase OPLA_YEAST, Cytosine deaminase FCY1_YEAST, AP-1 complex subunit mu-1-I AP1M1_YEAST, 54S ribosomal protein L35, mitochondrial RM35_YEAST, Mitochondrial inner membrane protein OXA1 OXA1_YEAST, Uncharacterized protein YBR096W YBU6_YEAST, and any combination thereof, 3 hours following exposure of said yeast to said modified plasma output for about 4.9 min as compared to non-exposed control yeast.

It is another object of the present invention to disclose the method as defined in any of the above, wherein said method is effective in upregulation of yeast proteins selected from the group consisting of: P38011 GBLP Guanine nucleotide-binding protein subunit beta-like protein, P00817 IPYR Inorganic pyrophosphatase, P00549 KPYK1 Pyruvate kinase 1, P00560 PGK Phosphoglycerate kinase, P00359 G3P3 Glyceraldehyde-3-phosphate dehydrogenase 3, P53549 PRS10 26S protease subunit RPT4, P53327 SLH1 Antiviral helicase SLH1, P38013 AHP1 Peroxiredoxin type-2, P00925 ENO2 Enolase 2, P34760 TSA1 Peroxiredoxin TSA1, P00924 ENO1 Enolase 1, P10591 HSP71 Heat shock protein SSA1, P11484 HSP75 (SSB1) Ribosome-associated molecular chaperone SSB1, P23301 IF5A1 Eukaryotic translation initiation factor 5A-1, P40069 IMB4 Importin subunit beta-4, P38999 LYS9 Saccharopine dehydrogenase [NADP(+), L-glutamate-forming], P40096 NCB 1 Negative cofactor 2 complex subunit alpha, P07560 SEC4 Ras-related protein SEC4, P26637 SYLC Leucine—tRNA ligase, cytoplasmic, P16521 EF3A Elongation factor 3A, P00925 ENO2 Enolase 2, P14540 ALF Fructose-bisphosphate aldolase, P00924 ENO1 Enolase 1, P34215 YBZ4 Putative uncharacterized protein YBR144C, P05694 METE 5-methyltetrahydropteroyltriglutamate—homocysteine methyltransferase, P34760TSA1 Peroxiredoxin TSA1, P16521 EF3A Elongation factor 3A, P00925 ENO2 Enolase 2, P49435 APT1 (3R8) Adenine phosphoribosyltransferase 1, P36047 YKT6 Synaptobrevin homolog YKT6, P00924 ENO1 Enolase 1, P38624 PSB1 Proteasome subunit beta type-1, P07143 CY1 Cytochrome cl, heme protein, mitochondrial, P38523 GRPE GrpE protein homolog, mitochondrial P11484 HSP75 Ribosome-associated molecular chaperone SSB1, P22768 ASSY Argininosuccinate synthase, P38886 RPN10 26S proteasome regulatory subunit RPN10, P14832 CYPH Peptidyl-prolyl cis-trans isomerase, P05743 RL26A 60S ribosomal protein L26-A, P19414 ACON Aconitate hydratase, mitochondrial, Q3E841 YN034 Uncharacterized protein YNR034W-A, P38061 RL32 60S ribosomal protein L32, P00358 G3P2 Glyceraldehyde-3-phosphate dehydrogenase 2, P09457 ATPO ATP synthase subunit 5, mitochondrial, P16474 GRP78 78 kDa glucose-regulated protein homolog and any combination thereof, following exposure of said yeast to said modified plasma output for about 4.9 min as compared to non-exposed control yeast.

It is another object of the present invention to disclose the method as defined in any of the above, wherein said method is effective in induction of E. coli proteins belonging to a protein class selected from the group consisting of: enzyme modulator (PC00095), hydrolase (PC00121), isomerase (PC00135), ligase (PC00142), lyase (PC00144), membrane traffic protein (PC00150), nucleic acid binding (PC00171), oxidoreductase (PC00176), transcription factor (PC00218), transferase (PC00220), transporter (PC00227), and any combination thereof, following exposure of said E. coli to said modified plasma output for about 4.2 min as compared to non-exposed control E. coli.

It is another object of the present invention to disclose the method as defined in any of the above, wherein said method is effective in induction of E. coli proteins belonging to a protein pathway selected from the group consisting of: 5-Hydroxytryptamine degradation (P04372), Adenine and hypoxanthine salvage pathway (P02723), Aminobutyrate degradation (P02726), Arginine biosynthesis (P02728), Ascorbate degradation (P02729), De novo pyrimidine deoxyribonucleotide biosynthesis (P02739), Flavin biosynthesis (P02741), Formyltetrahydroformate biosynthesis (P02743), Gamma-aminobutyric acid synthesis (P04384), Heme biosynthesis (P02746), Histidine biosynthesis (P02747), Hypoxia response via HIF activation (P00030), Lysine biosynthesis (P02751), Pentose phosphate pathway (P02762), Tetrahydrofolate biosynthesis (P02742), Tryptophan biosynthesis (P02783), and any combination thereof, following exposure of said E. coli to said modified plasma output for about 4.2 min as compared to non-exposed control E. coli It is another object of the present invention to disclose the method as defined in any of the above, wherein said method is effective in induction in of E. coli proteins selected from the group consisting of: PYRI_ECOLI Aspartate carbamoyltransferase regulatory chain, YHHA_ECOLI Uncharacterized protein YhhA, ZAPD_ECOLI Cell division protein ZapD, RIBA_ECOLI GTP cyclohydrolase-2, YIAD_ECOLI Probable lipoprotein YiaD, UDG_ECOLI UDP-glucose 6-dehydrogenase, GLTD_ECOLI Glutamate synthase [NADPH] small chain, GABD_ECOLI Succinate-semialdehyde dehydrogenase [NADP(+)] GabD, PYRF_ECOLI Orotidine 5'-phosphate decarboxylase, ARGE_ECOLI Acetylornithine deacetylase, FTSN_ECOLI Cell division protein FtsN, PAL_ECOLI Peptidoglycan-associated lipoprotein, DXR_ECOLI 1-deoxy-D-xylulose 5-phosphate reductoisomerase, SOHB_ECOLI Probable protease SohB, ADD_ECOLI Adenosine deaminase, YDHR_ECOLI Putative monooxygenase YdhR, YCII_ECOLI Protein YciI, ARAD_ECOLI L-ribulose-5-phosphate 4-epimerase AraD, GLND_ECOLI Bifunctional uridylyltransferase/uridylyl-removing enzyme, PDXJ_ECOLI Pyridoxine 5'-phosphate synthase, RODZ_ECOLI Cytoskeleton protein RodZ, YAAA_ECOLI UPF0246 protein YaaA, YFCH_ECOLI Epimerase family protein YfcH, FUCI_ECOLI L-fucose isomerase, HEM3_ECOLI Porphobilinogen deaminase, YECJ_ECOLI Uncharacterized protein YecJ, RUVA_ECOLI Holliday junction ATP-dependent DNA helicase RuvA, RL32_ECOLI 50S ribosomal protein L32, YDJN_ECOLI L-cystine transporter YdjN, QUEC_ECOLI 7-cyano-7-deazaguanine synthase, SPPA_ECOLI Protease 4, RNPH_ECOLI Inactive ribonuclease PH, SUFS_ECOLI Cysteine desulfurase, EPTA_ECOLI Phosphoethanolamine transferase EptA, NARP_ECOLI Nitrate/nitrite response regulator protein NarP, RUVB_ECOLI Holliday junction ATP-dependent DNA helicase RuvB, KDSC_ECOLI 3-deoxy-D-manno-octulosonate 8-phosphate phosphatase KdsC, YKGE_ECOLI Uncharacterized protein YkgE, DDPA_ECOLI Probable D,D-dipeptide-binding periplasmic protein DdpA, YFCZ_ECOLI UPF0381 protein YfcZ, PPA_ECOLI Periplasmic AppA protein, YFCF_ECOLI Glutathione S-transferase YfcF, MLAA_ECOLI Probable phospholipid-binding lipoprotein MlaA, ABGA_ECOLI p-aminobenzoyl-glutamate hydrolase subunit A, SFSA_ECOLI Sugar fermentation stimulation protein A, FEPA_ECOLI Ferrienterobactin receptor, LPTB_ECOLI Lipopolysaccharide export system ATP-binding protein LptB, RS8_ECOLI 30S ribosomal protein S8, YBBN_ECOLI Uncharacterized protein YbbN, YHGF_ECOLI Protein YhgF, UVRD_ECOLI DNA helicase II, GLPD_ECOLI Aerobic glycerol-3-phosphate dehydrogenase, SPEE_ECOLI Polyamine aminopropyltransferase, GUDD_ECOLI Glucarate dehydratase, YGFB_ECOLI UPF0149 protein YgfB, YCAR_ECOLI UPF0434 protein YcaR, CUSA_ECOLI Cation efflux system protein CusA and any combination thereof immediately following exposure of said E. coli to said modified plasma output for about 4.2 min as compared to non-exposed control E. coli.

It is another object of the present invention to disclose the method as defined in any of the above, wherein said method is effective in induction of E. coli proteins selected from the group consisting of: YEAK_ECOLI Uncharacterized protein YeaK, RNC_ECOLI Ribonuclease 3, RSMG_ECOLI Ribosomal RNA small subunit methyltransferase G, HIS8_ECOLI Histidinol-phosphate aminotransferase, THIL_ECOLI, Thiamine-monophosphate kinase, MNME_ECOLI tRNA modification GTPase MnmE, ZAPA_ECOLI Cell division protein ZapA, NUDK_ECOLI GDP-mannose pyrophosphatase NudK, OPPF_ECOLI Oligopeptide transport ATP-binding protein OppF, GLSA1_ECOLI Glutaminase 1, ARNC_ECOLI Undecaprenyl-phosphate 4-deoxy-4-formamido-L-arabinose transferase, HIS5_ECOLI Imidazole glycerol phosphate synthase subunit HisH, DUT_ECOLI Deoxyuridine 5'-triphosphate nucleotidohydrolase, NLPE_ECOLI Lipoprotein NlpE, BEPA_ECOLI Beta-barrel assembly-enhancing protease, YGJR_ECOLI Uncharacterized oxidoreductase YgjR, GLTD_ECOLI Glutamate synthase [NADPH] small chain, COPA_ECOLI Copper-exporting P-type ATPase A, ARGE_ECOLI Acetylornithine deacetylase, LEXA_ECOLI LexA repressor, SPEE_ECOLI Polyamine aminopropyltransferase, GUDD_ECOLI Glucarate dehydratase, YMDB_ECOLI O-acetyl-ADP-ribose deacetylase, MALK_ECOLI Maltose/maltodextrin import ATP-binding protein MalK, RSTA_ECOLI Transcriptional regulatory protein RstA, YFCH_ECOLI Epimerase family protein YfcH, RSGA_ECOLI Small ribosomal subunit biogenesis GTPase RsgA, WECB_ECOLI UDP-N-acetylglucosamine 2-epimerase, RHLE_ECOLI ATP-dependent RNA helicase RhlE, RUVA_ECOLI Holliday junction ATP-dependent DNA helicase RuvA, RNPH_ECOLI Inactive ribonuclease PH, RDGC_ECOLI Recombination-associated protein RdgC, SECY_ECOLI Protein translocase subunit SecY, RIBB_ECOLI 3,4-dihydroxy-2-butanone 4-phosphate synthase, OPGH_ECOLI Glucans biosynthesis glucosyltransferase H, YIHW_ECOLI Uncharacterized HTH-type transcriptional regulator YihW, POTD_ECOLI Spermidine/putrescine-binding periplasmic protein, TRPA_ECOLI Tryptophan synthase alpha chain, GPR_ECOLI L-glyceraldehyde 3-phosphate reductase, GLPD_ECOLI Aerobic glycerol-3-phosphate dehydrogenase, SOHB_ECOLI Probable protease SohB, MOAB_ECOLI Molybdenum cofactor biosynthesis protein B, and any combination thereof, 1 hour following exposure of said E. coli to said modified plasma output for about 4.2 min as compared to non-exposed control E. coli.

It is another object of the present invention to disclose the method as defined in any of the above, wherein said method is effective in induction of E. coli proteins selected from the group consisting of HIS7_ECOLI Histidine biosynthesis bifunctional protein HisB, STPA_ECOLI DNA-binding protein StpA, F16PA_ECOLI Fructose-1,6-bisphosphatase class 1, YQFB_ECOLI UPF0267 protein YqfB, RLM-J_ECOLI Ribosomal RNA large subunit methyltransferase J, YAJD_ECOLI Putative HNH nuclease YajD, YIAF_ECOLI Uncharacterized protein YiaF; SECF_ECOLI Protein translocase subunit SecF; YECJ_ECOLI Uncharacterized protein YecJ; RL32_ECOLI 50S ribosomal protein L32; TOLQ_ECOLI Protein TolQ; YEAK_ECOLI Uncharacterized protein YeaK; RNC_ECOLI Ribonuclease 3; ARNC_ECOLI Undecaprenyl-phosphate 4-deoxy-4-formamido-L-arabinose transferase; XYLA_ECOLI Xylose isomerase, UDG_ECOLI UDP-glucose 6-dehydrogenase, NARL_ECOLI Nitrate/nitrite response regulator protein NarL, LEXA_ECOLI LexA repressor, YMDB_ECOLI O-acetyl-ADP-ribose deacetylase, ARAD_ECOLI L-ribulose-5-phosphate 4-epimerase AraD, YMBA_ECOLI Uncharacterized lipoprotein YmbA, FOLC_ECOLI Dihydrofolate synthase/folylpolyglutamate synthase; PIMT_ECOLI Protein-L-isoaspartate O-methyltransferase, YFCH_ECOLI Epimerase family protein YfcH, TOLA_ECOLI Protein TolA, YKGF_ECOLI Uncharacterized electron transport protein YkgF, RNPH_ECOLI Inactive ribonuclease PH, DAPE_ECOLI Succinyl-diaminopimelate desuccinylase, GLNQ_ECOLI Glutamine transport ATP-binding protein GlnQ, YDCF_ECOLI Protein YdcF, ASTC_ECOLI Succinylornithine transaminase, SAD_ECOLI Succinate semialdehyde dehydrogenase [NAD(P)+] Sad, RF3_ECOLI Peptide chain release factor RF3, YEJL_ECOLI, UPF0352 protein YejL, UVRD_ECOLI DNA helicase II and any combination thereof, 6 hours following exposure of said E. coli to said modified plasma output for about 4.2 min as compared to non-exposed control E. coli.

It is another object of the present invention to disclose the method as defined in any of the above, wherein said method is effective in upregulation of E. coli proteins selected from the group consisting of: Lipopolysaccharide export system ATP-binding protein LptB—LPTB_ECOLI, Probable lipoprotein YiaD—YIAD_ECOLI, Cell division protein FtsN—FTSN_ECOLI, Adenosine deaminase—ADD_ECOLI, L-cystine transporter YdjN—YDJN_ECOLI, Cation efflux system protein CusA—CUSA_ECOLI, Orotidine 5'-phosphate decarboxylase—PYRF_ECOL, Beta-barrel assembly-enhancing protease—BEPA_ECOLI, Uncharacterized oxidoreductase YgjR—YGJR_ECOLI, L-glyceraldehyde 3-phosphate reductase—GPR_ECOLI, Ribosomal RNA small subunit methyltransferase G—RSMG_ECOLI and any combination thereof following exposure of said E. coli to said modified plasma output for about 4.2 min as compared to non-exposed control E. coli.

It is another object of the present invention to disclose the method as defined in any of the above, wherein said method is effective in downregulation of E. coli proteins selected from the group consisting of: Uncharacterized protein YeaK—YEAK_ECOLI; Uncharacterized HTH-type transcriptional regulator YihW-YIHW_ECOLI, Molybdenum cofactor biosynthesis protein B—MOAB_ECOLI, GDP-mannose pyrophosphatase NudK—NUDK_ECOLI, Probable protease SohB—SOHB_ECOL, Orotidine 5'-phosphate decarboxylase—PYRF_ECOLI, UPF0149 protein YgfB—YGFB_ECOLI, Adenosine deaminase—ADD_ECOLI, Aspartate carbamoyltransferase regulatory chain—PYRI_ECOLI, Cytoskeleton protein RodZ—RODZ_ECOLI, Cell division protein FtsN—FTSN_ECOLI and any combination thereof following exposure of said E. coli to said modified plasma output for about 4.2 min as compared to non-exposed control E. coli.

It is another object of the present invention to disclose the method as defined in any of the above, wherein said method is effective in induction of E. coli proteins belonging to a protein class selected from the group consisting of: calcium-binding protein (PC00060), chaperone (PC00072), enzyme modulator (PC00095), hydrolase (PC00121), isomerase (PC00135), ligase (PC00142), lyase (PC00144), nucleic acid binding (PC00171), oxidoreductase (PC00176), transcription factor (PC00218), transferase (PC00220), transporter (PC00227) and any combination thereof, following exposure of said E. coli to said modified plasma output for about 9.8 min as compared to non-exposed control E. coli.

It is another object of the present invention to disclose the method as defined in any of the above, wherein said method is effective in induction of E. coli proteins belonging to a protein pathway selected from the group consisting of: 5-Hydroxytryptamine degradation (P04372), Arginine biosynthesis (P02728), Asparagine and aspartate biosynthesis (P02730), Chorismate biosynthesis (P02734), De novo purine biosynthesis (P02738), De novo pyrimidine deoxyribonucleotide biosynthesis (P02739) De novo pyrimidine ribonucleotides biosynthesis (P02740), Formyltetrahydroformate biosynthesis (P02743), Heme biosynthesis (P02746), Histidine biosynthesis (P02747), Huntington disease (P00029), Hypoxia response via HIF activation (P00030), N-acetylglucosamine metabolism (P02756), O-antigen biosynthesis (P02757), Peptidoglycan biosynthesis (P02763), Phenylalanine biosynthesis (P02765), Proline biosynthesis (P02768), Pyrimidine Metabolism (P02771), Pyruvate metabolism (P02772), Serine glycine biosynthesis (P02776), TCA cycle (P00051), Tetrahydrofolate biosynthesis (P02742) and Tryptophan biosynthesis (P02783) and any combination thereof, following exposure of said E. coli to said modified plasma output for about 9.8 min as compared to non-exposed control E. coli.

It is another object of the present invention to disclose the method as defined in any of the above, wherein said method is effective in induction of E. coli proteins selected from the group consisting of: HPF_ECOLI Ribosome hibernation promoting factor, UBIE_ECOLI Ubiquinone/menaquinone biosynthesis C-methyltransferase UbiE, PYRI_ECOLI Aspartate carbamoyltransferase regulatory chain, NDK_ECOLI Nucleoside diphosphate kinase, GUAC_ECOLI GMP reductase, RLMN_ECOLI Dual-specificity RNA methyltransferase RlmN, YIHI_ECOLI Der GTPase-activating protein YihI, PROB_ECOLI Glutamate 5-kinase, YIAD_ECOLI Probable lipoprotein YiaD, AK2H_ECOLI Bifunctional aspartokinase/homoserine dehydrogenase 2, TATA_ECOLI Sec-independent protein translocase protein TatA, RMLB1_ECOLI dTDP-glucose 4,6-dehydratase 1, TRPB_ECOLI Tryptophan synthase beta chain, GLTD_ECOLI Glutamate synthase [NADPH] small chain, ALAC_ECOLI Glutamate-pyruvate aminotransferase AlaC, GALF_ECOLI UTP—glucose-1-phosphate uridylyltransferase, YBBN_ECOLI Uncharacterized protein YbbN, MIAA_ECOLI tRNA dimethylallyltransferase, BAER_ECOLI Transcriptional regulatory protein BaeR, MASZ_ECOLI Malate synthase G, FTSN_ECOLI Cell division protein FtsN, ALAA_ECOLI Glutamate-pyruvate aminotransferase AlaA, THIL_ECOLI Thiamine-monophosphate kinase, DXR_ECOLI 1-deoxy-D-xylulose 5-phosphate reductoisomerase, YFBT_ECOLI Hexitol phosphatase A, MDTE_ECOLI Multidrug resistance protein MdtE, SUFC_ECOLI Probable ATP-dependent transporter SufC, CYSD_ECOLI Sulfate adenylyltransferase subunit 2, OXYR_ECOLI Hydrogen peroxide-inducible genes activator, YCCU_ECOLI Uncharacterized protein YccU, GLRX1_ECOLI Glutaredoxin 1, YGGS_ECOLI Pyridoxal phosphate homeostasis protein, CSDA_ECOLI Cysteine desulfurase CsdA, YCEI_ECOLI Protein YceI, RODZ_ECOLI Cytoskeleton protein RodZ, GCH1L_ECOLI GTP cyclohydrolase 1 type 2 homolog, MURI_ECOLI Glutamate racemase, RSGA_ECOLI Small ribosomal subunit biogenesis GTPase RsgA, SERB_ECOLI Phosphoserine phosphatase, RLMB_ECOLI 23S rRNA (guanosine-2'-O-)-methyltransferase RlmB, YFCL_ECOLI Uncharacterized protein YfcL, RCSF_ECOLI Outer membrane lipoprotein RcsF, DLHH_ECOLI Putative carboxymethylenebutenolidase, YGJR_ECOLI Uncharacterized oxidoreductase YgjR, RNPH_ECOLI Inactive ribonuclease PH, RNG_ECOLI Ribonuclease G, TATB_ECOLI Sec-independent protein translocase protein TatB, YEBE_ECOLI Inner membrane protein YebE, LEP_ECOLI Signal peptidase I, GLPA_ECOLI Anaerobic glycerol-3-phosphate dehydrogenase subunit A, YEBV_ECOLI Uncharacterized protein YebV, AROC_ECOLI Chorismate synthase, RLMM_ECOLI Ribosomal RNA large subunit methyltransferase M, RATB_ECOLI UPF0125 protein RatB, UBII_ECOLI 2-octaprenylphenol hydroxylase, SPOT_ECOLI Bifunctional (p)ppGpp synthase/hydrolase SpoT, MUKE_ECOLI Chromosome partition protein MukE, OSME_ECOLI Osmotically-inducible putative lipoprotein OsmE, LDCI_ECOLI Inducible lysine decarboxylase, PFLA_ECOLI Pyruvate formate-lyase 1-activating enzyme, MTOX_ECOLI N-methyl-L-tryptophan oxidase, AROG_ECOLI Phospho-2-dehydro-3-deoxyheptonate aldolase Phe-sensitive, YHHA_ECOLI Uncharacterized protein YhhA, LPTB_ECOLI Lipopolysaccharide export system ATP-binding protein LptB, FRDB_ECOLI Fumarate reductase iron-sulfur subunit, DSBA_ECOLI Thiol:disulfide interchange protein DsbA, MDAB_ECOLI Modulator of drug activity B, TSX_ECOLI Nucleoside-specific channel-forming protein tsx, CSDE_ECOLI Sulfur acceptor protein CsdE, RSUA_ECOLI Ribosomal small subunit pseudouridine synthase A, INGK_ECOLI Inosine-guanosine kinase, DNLJ_ECOLI DNA ligase, NADC_ECOLI Nicotinate-nucleotide pyrophosphorylase [carboxylating], FKBX_ECOLI FKBP-type 16 kDa peptidyl-prolyl cis-trans isomerase, MAK_ECOLI Fructokinase, DYR_ECOLI Dihydrofolate reductase, MLAF_ECOLI Probable phospholipid import ATP-binding protein MlaF, MUKB_ECOLI Chromosome partition protein MukB, POTD_ECOLI Spermidine/putrescine-binding periplasmic protein, MLAC_ECOLI Probable phospholipid-binding protein MlaC, MGLA_ECOLI Galactose/methyl galactoside import ATP-binding protein MglA, OPGD_ECOLI Glucans biosynthesis protein D, QOR1_ECOLI Quinone oxidoreductase 1, MAO1_ECOLI NAD-dependent malic enzyme and any combination thereof, immediately following exposure of said E. coli to said modified plasma output for about 9.8 min as compared to non-exposed control E. coli.

It is another object of the present invention to disclose the method as defined in any of the above, wherein said method is effective in induction of E. coli proteins selected from the group consisting of: YCCU_ECOLI Uncharacterized protein YccU, GRCA_ECOLI Autonomous glycyl radical cofactor; AROG_ECOLI Phospho-2-dehydro-3-deoxyheptonate aldolase, Phe-sensitive, EFEO_ECOLI Iron uptake system component EfeO, LPXD_ECOLI UDP-3-O-(3-hydroxymyristoyl)glucosamine N-acyltransferase, SOHB_ECOLI Probable protease SohB, NRDD_ECOLI Anaerobic ribonucleoside-triphosphate reductase, HELD_ECOLI DNA helicase IV, OTSA_ECOLI Trehalose-6-phosphate synthase, LEXA_ECOLI LexA repressor, GPPA_ECOLI Guanosine-5'-triphosphate,3'-diphosphate pyrophosphatase, 3PASE_ECOLI Inorganic triphosphatase, RL28_ECOLI 50S ribosomal protein L28, YBBN_ECOLI Uncharacterized protein YbbN, PREA_ECOLI NAD-dependent dihydropyrimidine dehydrogenase subunit PreA, DXR_ECOLI 1-deoxy-D-xylulose 5-phosphate reductoisomerase, GUDD_ECOLI Glucarate dehydratase, YMDB_ECOLI O-acetyl-ADP-ribose deacetylase, NAGA_ECOLI N-acetylglucosamine-6-phosphate deacetylase, PTH_ECOLI Peptidyl-tRNA hydrolase, YFGD_ECOLI Uncharacterized protein YfgD, CUEO_ECOLI Blue copper oxidase CueO, YNIC_ECOLI Hexitol phosphatase B, RSMA_ECOLI Ribosomal RNA small subunit methyltransferase A, RSGA_ECOLI Small ribosomal subunit biogenesis GTPase RsgA, YEEN_ECOLI Probable transcriptional regulatory protein YeeN, RHLE_ECOLI ATP-dependent RNA helicase RhlE, ANMK_ECOLI Anhydro-N-acetylmuramic acid kinase, YKGF_ECOLI Uncharacterized electron transport protein YkgF, RCSF_ECOLI Outer membrane lipoprotein RcsF, KDSC_ECOLI 3-deoxy-D-manno-octulosonate 8-phosphate phosphatase KdsC, ARTP_ECOLI Arginine transport ATP-binding protein ArtP, ATDA_ECOLI Spermidine N(1)-acetyltransferase, YGHA_ECOLI Uncharacterized oxidoreductase YghA, YFEY_ECOLI Uncharacterized protein YfeY, OSME_ECOLI Osmotically-inducible putative lipoprotein OsmE, PTM3C_ECOLI PTS system mannitol-specific EIICBA component, RF3_ECOLI Peptide chain release factor RF3, YGGS_ECOLI Pyridoxal phosphate homeostasis protein, BETB_ECOLI NAD/NADP-dependent betaine aldehyde dehydrogenase, RS16_ECOLI 30S ribosomal protein S16, NRDR_ECOLI Transcriptional repressor NrdR, and any combination thereof, 1 hour following exposure of said E. coli to said modified plasma output for about 9.8 min as compared to non-exposed control E. coli.

It is another object of the present invention to disclose the method as defined in any of the above, wherein said method is effective in induction of E. coli proteins selected from the group consisting of: PHEA_ECOLI P protein; FTSA_ECOLI Cell division protein FtsA; STPA_ECOLI DNA-binding protein StpA, UDG_ECOLI UDP-glucose 6-dehydrogenase, YJBR_ECOLI Uncharacterized protein YjbR, YCIO_ECOLI Uncharacterized protein YciO, GPR_ECOLI L-glyceraldehyde 3-phosphate reductase, RS8_ECOLI 30S ribosomal protein S8, GLTD_ECOLI Glutamate synthase [NADPH] small chain, ISCU_ECOLI Iron-sulfur cluster assembly scaffold protein IscU, CSDA_ECOLI Cysteine desulfurase CsdA, HIS5_ECOLI Imidazole glycerol phosphate synthase subunit HisH, YBIC_ECOLI Hydroxycarboxylate dehydrogenase B, YCFP_ECOLI UPF0227 protein YcfP, SDHD_ECOLI D-serine dehydratase, OTSA_ECOLI Trehalose-6-phosphate synthase, GPPA_ECOLI Guanosine-5'-triphosphate, 3'-diphosphate pyrophosphatase, TSAE_ECOLI tRNA threonylcarbamoyladenosine biosynthesis protein TsaE, YEGQ_ECOLI Uncharacterized protease YegQ, YHGF_ECOLI Protein YhgF, DXR_ECOLI 1-deoxy-D-xylulose 5-phosphate reductoisomerase, FDOH_ECOLI Formate dehydrogenase-O iron-sulfur subunit, GUDD_ECOLI Glucarate dehydratase, YMDB_ECOLI O-acetyl-ADP-ribose deacetylase, MGSA_ECOLI Methylglyoxal synthase, RS16_ECOLI 30S ribosomal protein S16, SUFC_ECOLI Probable ATP-dependent transporter SufC, OTC 1_ECOLI Ornithine carbamoyltransferase subunit I, UBID_ECOLI 3-octaprenyl-4-hydroxybenzoate carboxy-lyase, YNIC_ECOLI Hexitol phosphatase B, IAAA_ECOLI Isoaspartyl peptidase, RSGA_ECOLI Small ribosomal subunit biogenesis GTPase RsgA, SUPH_ECOLI Sugar phosphatase YbiV, HEM3_ECOLI Porphobilinogen deaminase, FHUA_ECOLI Ferrichrome-iron receptor, RSMC_ECOLI Ribosomal RNA small subunit methyltransferase C, QUEC_ECOLI 7-cyano-7-deazaguanine synthase, PKA_ECOLI Protein lysine acetyltransferase Pka, YJGR_ECOLI Uncharacterized protein YjgR, TATB_ECOLI Sec-independent protein translocase protein TatB, YEBE_ECOLI Inner membrane protein YebE, RMLB2_ECOLI dTDP-glucose 4,6-dehydratase 2, MNMC_ECOLI tRNA 5-methylaminomethyl-2-thiouridine biosynthesis bifunctional protein MnmC, TOLQECOLI Protein TolQ, YCED_ECOLI Large ribosomal RNA subunit accumulation protein YceD, KDSC_ECOLI 3-deoxy-D-manno-octulosonate 8-phosphate phosphatase KdsC, ATDA_ECOLI Spermidine N(1)-acetyltransferase, E4PD_ECOLI D-erythrose-4-phosphate dehydrogenase, PRMA_ECOLI Ribosomal protein L11 methyltransferase, PTRA_ECOLI Protease 3, NUDJ_ECOLI Phosphatase NudJ, CYSD_ECOLI Sulfate adenylyltransferase subunit 2, UGPB_ECOLI sn-glycerol-3-phosphate-binding periplasmic protein UgpB, GHRA_ECOLI Glyoxylate/hydroxypyruvate reductase A, GNSA_ECOLI Protein GnsA, FTSN_ECOLI Cell division protein FtsN, RLMB_ECOLI 23S rRNA (guanosine-2'-O-)-methyltransferase RlmB, PYRF_ECOLI Orotidine 5'-phosphate decarboxylase, YKGE_ECOLI Uncharacterized protein YkgE, YBBN_ECOLI Uncharacterized protein YbbN and any combination thereof, 6 hours following exposure of said *E. coli* to said modified plasma output for about 9.8 min as compared to non-exposed control *E. coli*.

It is another object of the present invention to disclose the method as defined in any of the above, wherein said method is effective in upregulation of *E. coli* proteins selected from the group consisting of: dTDP-glucose 4,6-dehydratase 1—RMLB1_ECOLI, Hexitol phosphatase A—YFBT_ECOLI, Ribosome hibernation promoting factor—HPF_ECOLI, Lipopolysaccharide export system ATP-binding protein LptB LPTB_ECOLI, Fumarate reductase iron-sulfur subunit—FRDB_ECOLI, Modulator of drug activity B—MDAB_ECOLI, Sulfur acceptor protein CsdE—CSDE_ECOLI, Transcriptional regulatory protein BaeR—BAER_ECOLI, Glutamate-pyruvate aminotransferase AlaA—ALAA_ECOLI, GMP reductase—GUAC_ECOLI, Glutamate 5-kinase (upregulated in two time points)—PROB_ECOLI, UTP—glucose-1-phosphate uridylyltransferase—GALF_ECOL, Pyridoxal phosphate homeostasis protein—YGGS_ECOL, Dual-specificity RNA methyltransferase RlmN—RLMN_ECOLI, N-methyl-L-tryptophan oxidase—MTOX_ECOLI), Ubiquinone/menaquinone biosynthesis C-methyltransferase UbiE—UBIE_ECOLI, Glutamate-pyruvate aminotransferase AlaC—ALAC_ECOLI, DNA ligase—DNLJ_ECOLI, Fructokinase—MAK_ECOLI, Dihydrofolate reductase—DYR_ECOLI, Putative carboxymethylenebutenolidase—DLHH_ECOLI, Malate synthase G—MASZ_ECOLI, Chromosome partition protein MukB—MUKB_ECOLI, PTS system mannitol-specific EIICBA component—PTM3C_ECOLI, Transcriptional repressor NrdR—NRDR_ECOLI, L-glyceraldehyde 3-phosphate reductase—GPR_ECOLI, UPF0227 protein YcfP—YCFP_ECOLI, D-serine dehydratase—SDHD_ECOLI, Orotidine 5'-phosphate decarboxylase—PYRF_ECOLI, Uncharacterized electron transport protein YkgF—30YKGE_ECOL, and any combination thereof, following exposure of said *E. coli* to said modified plasma output for about 9.8 min as compared to non-exposed control *E. coli*

It is another object of the present invention to disclose the method as defined in any of the above, wherein said method is effective in downregulation of *E. coli* proteins selected from the group consisting of: FKBP-type 16 kDa peptidyl-prolyl cis-trans isomerase—FKBX_ECOLI, Probable lipoprotein YiaD—YIAD_ECOLI, Tryptophan synthase beta chain—TRPB_ECOLI, Glutamate-pyruvate aminotransferase AlaC—ALAC_ECOLI, Uncharacterized protein YccU—YCCU_ECOLI, Ubiquinone/menaquinone biosynthesis C-methyltransferase UbiE—UBIE_ECOLI, Dual-specificity RNA methyltransferase RlmN—RLMN_ECOLI, Sulfate adenylyltransferase subunit 2—CYSD_ECOLI, Nucleoside diphosphate kinase—NDK_ECOLI, Thiol:disulfide interchange protein DsbA—DSBA_ECOLI, Uncharacterized protein YccU*2—YCCU_ECOLI, P-protein—PHEA_ECOLI and any combination thereof, following exposure of said *E. coli* to said modified plasma output for about 9.8 min as compared to non-exposed control *E. coli*.

It is another object of the present invention to disclose a protein produced by the method as defined in any of the above.

It is another object of the present invention to disclose the use of a protein as defined in any of the above, as a drug or pro-drug, food additive or food supplement, industrial enzyme and any combination thereof.

It is another object of the present invention to disclose a system for modulating protein expression as well as production, generation or induction of proteins 'de-novo', in targeted microorganisms, said system comprises: (a) a plasma discharge source for discharging plasma to said microorganisms, said plasma comprising about 70-98% Argon, about 6-9% Nitrogen and about 1.5-2.5% Oxygen by % (wt.); said plasma discharge electric field is in the range of 200-500 v/m; (b) a plasma modifying mechanism comprising (1) at least one magnetic material, and at least one piezoelectric material, and (2) at least one optical crystal material, said plasma modifying mechanism providing modified plasma output having frequencies in the range of about 3 KHz to about 30 KHz; (c) a non-transitory medium providing instructions for said plasma source to discharge said plasma in a predetermined pulsed profile characterized by pulse cycle duration in the range of 0.1-2.1 min each pulse cycle comprises a series of 6-57 "on pulses" and 3-44 pauses and the number of pulse cycles is in the range of 3 to 20, said profile effective in modulating said protein expression and production, generation or induction of proteins 'de-novo' in said targeted microorganisms exposed to said modified plasma output as compared to control microorganisms not exposed to said modified plasma output.

It is one object of the present invention to disclose a non-GM method for de novo generating of proteins in microorganisms from within the proteome of said microorganisms, said method comprises steps of:
a. providing a system comprising:
i. a plasma discharge source for discharging pulses of plasma to said microorganisms, said plasma comprising about 70 to about 98% argon, about 6 to 9% nitrogen and about 1.5 to about 2.5% oxygen by % (wt.); said plasma discharge electric field is in the range of 200 to about 500 v/m; and
ii. a plasma modifying mechanism comprising (1) at least one magnetic material, and at least one piezoelectric material, and (2) at least one optical crystal material, said plasma modifying mechanism providing modified plasma output having frequencies in the range of about 3 KHz to about 30 KHz; and
b. discharging said plasma towards microorganisms in a pulsed profile, said profile characterized by pulse cycle duration ranging from about 0.1 to about 2.1 min, each pulse cycle comprises a series of about 6 to about 57 "on pulses" and about 3 to about 44 pauses, number of pulse cycles ranging from about 3 to about 20, thereby activating proteins from said target microorganisms to de novo generating of proteins in microorganisms from within the proteome of said microorganisms.

It is another object of the present invention to disclose a method as defined in any of the above, wherein the distance between said plasma source and said targeted microorganisms is in the range of about 2 cm to about 10 cm, preferably about 3 cm to about 7 cm.

It is another object of the present invention to disclose a method as defined in any of the above, wherein said method is effective in generation of proteins de novo in said targeted microorganisms between 0 to 24 hours following said exposure to said modified plasma output, preferably between about 0 to 6 hours following said exposure to said modified plasma output.

It is another object of the present invention to disclose a method as defined in any of the above, wherein said modified plasma output is effective in a depth of at least about 6 cm.

It is another object of the present invention to disclose a method as defined in any of the above, wherein said microorganisms are in a substrate selected from a group consisting of food, liquid, beverage, suspension, biological culture, biological fluid, medium, growth medium, emulsion, biological tissue, plant, fluid, soil, minerals, media, gas, gas and liquid mixtures, gas mixtures, cells, tissue culture, organs and any combination thereof.

It is another object of the present invention to disclose a method as defined in any of the above, wherein said microorganisms are selected from a group consisting of yeast, bacteria, archaea, algae, fungi, protozoa, virus, spores, hypha, prion, *Candida*, corynebacteria, aerobic bacteria, anaerobic bacteria, *Listeria monocytogenes, Escherichia coli (E. coli), Salmonella*, bacteria of the Enterobacteriaceae family, bacteria of the Listeriaceae family, gram positive bacteria, gram negative bacteria, *Staphylococcus aureus, Pseudomonas aeruginosa, Staphylococcus epidermidis, Staphylococcus haemolyticus*, enterococcusfaecalis, Clostridiaceae family, *Clostridium*, corynebacteria, actinobacteria and any combination thereof.

It is another object of the present invention to disclose a method as defined in any of the above, wherein said proteins are selected from a group consisting of pellet proteins, supernatant proteins, intracellular proteins, extracellular proteins and any combination thereof in said targeted microorganisms as compared to said control microorganisms.

It is one object of the present invention to disclose non-GM method for modulating proteins in microorganisms, comprising steps of:
a. providing a system comprising:
i. a plasma discharge source, said plasma comprising about 70 to about 98% (wt.) argon, about 6 to 9% (wt.) nitrogen, and about 1.5 to about 2.5% oxygen by % (wt.); said plasma discharge electric field is in the range of about 200 to about 500 v/m; and
ii. a plasma modifying mechanism comprising (1) at least one magnetic material, and at least one piezoelectric material, and (2) at least one optical crystal material, said plasma modifying mechanism providing modified plasma output having frequencies in the range of about 3 KHz to about 30 KHz;
b. discharging said plasma towards said microorganisms in a pulsed profile, said profile characterized by pulse cycle duration ranging from about 0.1 to about 2.1 min, each pulse cycle comprises a series of 6 to 57 "on pulses" and about 3 to about 44 pauses, number of pulse cycles ranging from about 3 to about 20, thereby modulating proteins from said target microorganisms.

It is another object of the present invention to disclose a method as defined in any of the above, wherein the distance between said plasma source and said targeted microorganisms is in the range of about 2 cm to about 10 cm, preferably about 3 cm to about 7 cm.

It is another object of the present invention to disclose a method as defined in any of the above, wherein said method is provided useful for modulating proteins in said targeted microorganisms between 0 to about 24 hours following said exposure to said modified plasma output, preferably between about 0 to about 6 hours following said exposure to said modified plasma output.

It is another object of the present invention to disclose a method as defined in any of the above, wherein said modified plasma output is effective in a depth of at least about 6 cm.

It is another object of the present invention to disclose a method as defined in any of the above, wherein said microorganisms are in a substrate selected from the group consisting of: food, liquid, beverage, suspension, biological culture, biological fluid, medium, growth medium, emulsion, biological tissue, plant, fluid, soil, minerals, media, gas, gas and liquid mixtures, gas mixtures, cells, tissue culture, organs and any combination thereof.

It is another object of the present invention to disclose a method as defined in any of the above, wherein said microorganisms are selected from a group consisting of yeast, bacteria, archaea, algae, fungi, protozoa, virus, spores, hypha, prion, *Candida*, corynebacteria, aerobic bacteria, anaerobic bacteria, *Listeria monocytogenes, Escherichia coli (E. coli), Salmonella*, bacteria of the Enterobacteriaceae family, bacteria of the Listeriaceae family, gram positive bacteria, gram negative bacteria, *Staphylococcus aureus, Pseudomonas aeruginosa, Staphylococcus epidermidis, Staphylococcus haemolyticus*, enterococcusfaecalis, Clostridiaceae family, *Clostridium*, corynebacteria, actinobacteria and any combination thereof.

It is another object of the present invention to disclose a method as defined in any of the above, wherein said proteins are selected from the group consisting of pellet proteins, supernatant proteins, intracellular proteins, extracellular proteins and any combination thereof in said targeted microorganisms as compared to said control microorganisms.

It is one object of the present invention to disclose a system operable in a method as defined in a claim 1 or claim 8, said system comprises
  a. a plasma discharge source for discharging pulses of plasma to said microorganisms, said plasma comprising about 70 to about 98% (wt.) argon, about 6 to about 9% (wt.) nitrogen and about 1.5 to about 2.5% (wt.) oxygen; said plasma discharge electric field is in the range of about 200 to about 500 v/m;
  b. a plasma modifying mechanism comprising (1) at least one magnetic material, and at least one piezoelectric material, and (2) at least one optical crystal material, said plasma modifying mechanism providing modified plasma output having frequencies in the range of about 3 KHz to about 30 KHz; and
  c. a non-transitory medium providing instructions for said plasma source to discharge said plasma in a predetermined pulsed profile characterized by pulse cycle duration in the range of about 0.1 to about 2.1 min each pulse cycle comprises a series of about 6 to about 57 "on pulses" and about 3 to about 44 pauses and the number of pulse cycles is in the range of about 3 to about 20, and activating proteins from said target microorganisms, wherein at least one of said proteins is absent from control microorganisms not exposed to said modified plasma output.

It is one object of the present invention to disclose use of a protein provided in a method as defined in a claim 1 or claim 8 as a drug or pro-drug, food additive or food supplement, industrial enzyme and any combination thereof.

BRIEF DESCRIPTION OF THE FIGURES

In order to better understand the invention and its implementation in practice, a plurality of embodiments will now be described, by way of non-limiting example only, with reference to the accompanying drawings, wherein
FIGS. 3A-3B are diagrams presenting protein classifications uniquely revealed in the treated pellet cells;
FIGS. 4A-4C are diagrams presenting protein pathways in supernatant-based control (panel A) and treated (panel B) cells;
FIGS. 5A-5E are diagrams presenting protein pathways in pellet-based control (panel A) and treated (panel B) cells;
FIG. 6A-6B are diagrams presenting the protein class identified by the Panther software in treatment samples (panel A) and in control samples (panel B);
FIGS. 7A-7B are diagrams presenting protein pathways in the treated (panel A) and control (panel B) yeasts cells;
FIG. 8A presents PCA analysis performed in 2D, while
FIGS. 8B-8C present PCA performed in 3D;
FIGS. 11A-11B are diagrams presenting protein pathways analysis, in *E. coli* treatment samples of deep solution (BEAKER), identified by the Panther software;
FIG. 13 is a diagram presenting protein pathways analysis, in *E. coli* control samples of deep solution (BEAKER), identified by the Panther software;
FIG. 18 is a diagram presenting protein pathways analysis, in *E. coli* control samples of shallow solution (Petri Dish), identified by the Panther software.

DETAILED DESCRIPTION OF THE PREFERRED EMBODIMENTS

Figure 1:
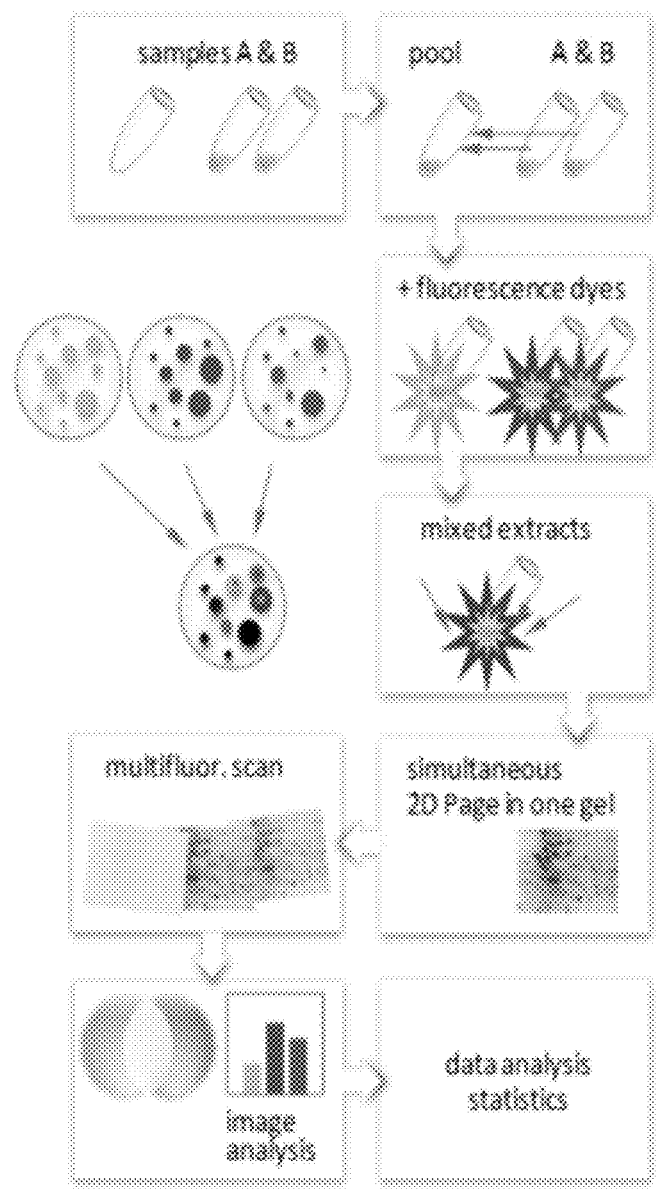
FIG. 1 is a schematic presentation of 2D-DIGE experimental setup and workflow as an embodiment of the present invention.

The following description is provided, alongside all chapters of the present invention, so as to enable any person skilled in the art to make use of said invention and sets forth the best modes contemplated by the inventor of carrying out this invention. Various modifications, however, is adapted to remain apparent to those skilled in the art, since the generic principles of the present invention have been defined specifically to provide means and methods for modulating protein expression as well as production, generation or induction of proteins de novo in microorganisms.

The present invention describes the proteins expressed in microbial cells following exposure to the herein defined modified plasma discharge output and compares them to corresponding cell samples not exposed to the same. The technology of the present invention enables to rapidly and effectively induce the production of specific proteins in microorganisms, without using recombinant proteins and genetic engineering methods.

The present disclosure also describes the pathways expressed or produced following exposure to the produced modified plasma discharge output. This approach describes the proteome of the microorganism in response to the exposure to the modified plasma output, which is the entire set of proteins that are produced or modified by the organism or system.

According to further embodiments, the unique proteins obtained following exposure of yeast and bacterial cells to the application of the specifically designed modified plasma technology, are herein described. It is further within the scope to examine differences in the cellular and post-translational modification processes of treated and non-treated cells by the modified plasma technology. Furthermore, the secreted/produced proteins of the cell pellet and supernatant are examined separately in order to identify specific proteins and protein pathways that are induced or upregulated in response to the treatment with or without exposure to different environmental conditions and metabolic stresses.

According to main embodiments, the disclosed system generates atmospheric pressure non-thermal plasma influenced by magnetic and piezoelectric materials combined with optical crystal material. The modified plasma output is provided to the treated subject in a predefined pulsed profile effective for upregulation or induction of specific protein expression, as well as production, generation or induction of proteins 'de-novo' in microorganisms.

It is emphasized that the system and method of the present invention is not restricted to producing proteins from a particular organism, but it is a non-invasive method that can be adjusted to various organisms, as opposed to genetic engineering methods and approaches which are based and dependent on the specific selected organism which produces recombinant proteins.

The current invention uses microorganisms such as yeast, in particular the *S. cerevisiae*, and *E. coli* as target organisms for production of proteins by the non-invasive method of the present invention. Using yeast as targeted organism has several advantages such as being a unicellular organism (i.e., ease of genetic manipulation and rapid growth), ability to perform eukaryotic protein folding, assembly, and post-translational modification, production of high protein titers and a well-defined genome therefore being a genetically tractable organism. In addition, the yeast *S. cerevisiae*, which the American Food and Drug Administration (FDA) recognizes as an organism generally regarded as safe (GRAS), has a high glycosylation capacity leading to hyper-glycosylation and reduced secretion rate. Furthermore, yeast is considered a model organism for studying human proteins associated with genetic and degenerative diseases. More specifically, yeast is a valuable model for studying the molecular mechanisms of infectious diseases or endocrinal, nutritional, and metabolic disorders and other diseases such as cystic fibrosis, Huntington's disease, the prion-related diseases, Alzheimer's disease, and antitrypsin deficiency, Parkinson, diabetes mellitus, atherosclerosis and ischemia, and liver and heart diseases, and for researching new treatments for cancer, arthritis, immune and inflammatory disorders.

According to one embodiment, the present invention provides a method for modulating protein expression as well as production, generation or induction of proteins 'de-novo' in targeted microorganisms. The method comprises steps of:
(a) providing a system comprising: (i) a plasma discharge source for discharging plasma to said microorganisms, said plasma comprising about 70-98% Argon, about 6-9% Nitrogen and about 1.5-2.5% Oxygen by % (wt.); said plasma discharge electric field is in the range of 200-500 v/m; and (ii) a plasma modifying mechanism comprising (1) at least one magnetic material, and at least one piezoelectric material, and (2) at least one optical crystal material, said plasma modifying mechanism providing modified plasma output having frequencies in the range of about 3 KHz to about 30 KHz;
(b) providing preselected targeted microorganisms;
(c) providing instructions for said plasma source to discharge said plasma in a predetermined pulsed profile characterized by pulse cycle duration in the range of 0.15 to 1.68 min, each pulse cycle comprises a series of 6-57 "on pulses" and 3-44 pauses and the number of pulse cycles is in the range of 3 to 20, said profile effective in modulating said protein expression as well as production, generation or induction of proteins 'de-novo' in said targeted microorganisms exposed to said modified plasma output as compared to control microorganisms not exposed to said modified plasma output.

The present invention further provides a system for modulating protein expression as well as production, generation or induction of proteins 'de-novo' in targeted microorganisms. The aforementioned system comprises:
(a) a plasma discharge source for discharging plasma to said microorganisms, said plasma comprising about 70-98% Argon, about 6-9% Nitrogen and about 1.5-2.5% Oxygen by % (wt.); said plasma discharge electric field is in the range of 200-500 v/m;
(b) a plasma modifying mechanism comprising (1) at least one magnetic material, and at least one piezoelectric material, and (2) at least one optical crystal material, said plasma modifying mechanism providing modified plasma output having frequencies in the range of about 3 KHz to about 30 KHz;
(c) a non-transitory medium providing instructions for said plasma source to discharge said plasma in a predetermined pulsed profile characterized by pulse cycle duration in the range of 0.15 to 1.68 min, each pulse cycle comprises a series of 6-57 "on pulses" and 3-44 pauses and the number of pulse cycles is in the range of 3 to 20, said profile effective in modulating said protein expression, as well as production, generation or induction of proteins 'de-novo' in said targeted microorganisms exposed to said modified plasma output as compared to control microorganisms not exposed to said modified plasma output.

According to one embodiment, the plasma modifying mechanism optionally comprises a gas plasma flow regulator or monitoring means configured to control and/or monitor gas plasma flow parameters such as flow rate, flow pressure, mass flow, and gas plasma composition ratios.

In a specific embodiment, the gas plasma discharge comprises a gas mixture combination comprising Argon (Ar), $N_2$ and $O_2$. It is noted that the gas plasma flow regulator or monitoring means is configure to control and/or monitor the plasma flow parameters of the gas plasma mixture and each of its components or ingredients separately.

In main aspects the modified plasma output treatments and methods of the present invention are highly advantageous over the currently conventionally used methods for protein production in microorganisms. The following advantages of the system and method of the present invention are noted:

1. The system and method of the present invention require relatively short administration or exposure time of the treated subject (i.e. substrate hosting the microorganism) of between about 0.45 min to about 34 min, particularly between about 0.6 min to about 25 min and more particularly between about 2.8 min and about 9.8 min per treatment.

2. The resulted desirable effect is achieved after a relatively short recovery or incubation time of up to 24 hours, particularly up to 6 hours and more particularly up to 1 hour from exposure of the subject or microorganism to the modified plasma output treatment.

3. The modified plasma output treatment of the present invention is applied to the targeted subject or microorganism non-invasively, without the requirement for genetic engineering, transformation or transplantation processes, and without the use of catalyzing materials.

4. The modified output treatments of the present invention can be designed or adjusted by preselection of the pulse profile (including duration of each pulse cycle, number of pulse cycles, pattern of each pulse cycle in terms of number and duration of "on pulses" and number and duration of "pauses") for a predefined desirable organism, biological effect and/or desired protein expression profile.

5. The modified output treatments of the present invention can penetrate beneath the outer integument or surface of the treated subject or microorganism. On the other hand, the current conventionally used methods and systems report experiments showing surface modification, particularly treating superficial wounds on the outer surface of the skin (epidermis) or affecting the seed coat or sterilization of the outer layer of the skin or seed. The present invention is further configured to induce protein expression effect on layers or tissues, cells or regions not limited to the surface of the treated subject or microorganism. It is within the scope that the modified plasma output treatment is effective in a depth of at least about 6 cm, particularly in a depth of at least 8 cm and more particularly in a depth of at least 10 cm beneath the outer integument or surface or membrane of the treated subject or microorganisms.

According to further embodiments, the inventors provide a system comprising a non transitory medium for providing instructions to discharge plasma from a plasma source in a predetermined pulsed profile especially designed and effective in modulating protein expression as well as production, generation or induction of proteins 'de-novo' in targeted microorganisms exposed to modified plasma output, as compared to control microorganisms not exposed to said modified plasma output.

It is further within the scope of the invention, wherein the system and method of the present invention is adapted to provide a synergic effect with respect to effecting or modulating or inducing or upregulation or downregulating protein expression in microorganisms, as well as producing generating or inducing of proteins 'de-novo' as compared to the effect induced by conventionally used non-thermal plasma (NTP) source or discharger (absent of the plasma modifying mechanism of the present invention) or by each of the plasma modifying mechanism components or materials; individually or in a partial combination administered or provided.

In a further embodiment, the system of the present invention is adapted to provide a synergic effect with respect to inducing or upregulation protein expression which is at least about 5% higher than the effect provided by each of the components of the system of the present invention or their partial combination.

As used herein the term "about" denotes ±25% of the defined amount or measure or value.

As used herein, the term "plasma" or "non-thermal plasma" or "nonthermal plasma" or "cold plasma" or "NTP" generally refers hereinafter to any quasi-neutral mixture of charged particles and radicals in a partially ionized gas. More particularly, it refers to non-thermal atmospheric pressure plasma (NTAPP) which is defined as a partially ionized gas with electrically charged particles at atmospheric pressure. NTAPPs can be used without causing thermal damage to cells.

It is within the scope of the invention that the plasma, particularly, NTP is discharged by a plasma discharge source or device which can include "gliding arc", "plasma pencil", "plasma needle", "plasma jet", "dielectric barrier discharge", "one atmosphere uniform glow discharge plasma", "atmospheric plasma", "ambient pressure non-thermal discharges", "non-equilibrium atmospheric pressure plasmas" and dielectric barrier discharge (DBD)-type atmospheric pressure plasma device. The aforementioned terms relate to both: non-thermal plasma and plasma operated at or near atmospheric pressure. It is further within the context of the present invention that the term further refers to "cold" plasma defined as the one-atmosphere, near room temperature plasma discharges, which is distinguished from other plasmas, operating at hundreds or thousands of degrees above ambient.

It is further in the scope of the invention, wherein the plasma generated by the plasma source is selected from the group consisting of positive ions, negative ions, electrons metastables, atoms, free radicals and photons.

According to certain embodiments, the NTP emitting source is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

It is noted that the plasma gas composition of the present invention comprises a combination of ingredients or components in % (wt.) including about 70-98% Ar, about 6-9% $N_2$ and about 1.5-2.5% $O_2$.

The term "essentially" as used herein is generally defined as constituting or being part of the nature or essence of something; inherent. In the context of the present invention it may refer to a range of ±25% of the defined amount or measure or value.

The term "modulating" or "modulation" as used herein generally and interchangeably refers to regulation or adjustment to a certain degree. In the context of the present invention it particularly refers to regulating or adjusting to altering or adapting the expression of a gene or protein in microorganisms, with a view to use it to alleviate some form of an ailment or medical condition. In specific embodiments, the term "modulating" or "modulation" includes induction, regulation, upregulation or downregulation of protein expression, i.e. specific proteins, protein classes and protein pathways, in treated microorganisms exposed to the modified plasma output as compared to non-treated control microorganisms which were not exposed to the modified plasma output.

The term "protein expression" as used herein refers to protein synthesis, modification and regulation in living organisms. It is within the scope of the present invention that the term refers to generating specific proteins in microorganisms by the method of the present invention. It may include production or generation or induction of proteins 'de-novo' as a result of the exposure to the modified plasma output of the targeted microorganisms. These induced proteins do not appear in the control corresponding microorganisms not exposed to the modified plasma output treatment. In other aspects it includes upregulation or downregulation of specific proteins' expression as compared to the control group of microorganisms, not exposed to the modified plasma output treatment. The term "protein expression" refers both to prokaryotic and eukaryotic cells. It further refers to controlled and integrated actions of genes that can produce specific sets of proteins with characteristic structures that carry specific modifications needed for the cells to function. It further relates to "gene expression", which refers to the conversion of the information encoded in a gene first into messenger RNA and finally to a protein. The present invention provides means and methods for affecting the proteome of microorganisms or other organisms, which is the entire set of proteins expressed by a genome, cell, tissue, or organism at a certain time. More specifically, it is the set of expressed proteins in a given type of cell or organism, at a given time, under defined conditions. The term is a blend of proteins and genome and it includes an effect on protein pathways and classes.

The term "protein pathway" as used herein refers to a biological pathway which is a series of interactions among molecules in a cell that leads to a certain product or a change in a cell. Some of the most common biological pathways are involved in metabolism, the regulation of gene expression and the transmission of signals. Software are used by the present methods (such as the PANTHER) to identify protein pathways, each with subfamilies and protein sequences mapped to individual pathway components. The software provides a list of names of the pathways in which a query gene will be shown.

The term "protein class" as used herein refers to broad categories of protein topologies. They describe groups of proteins that share similar amino acid and/or secondary structure and/or function proportions. Each class contains multiple, independent protein superfamilies. Amongst other bioinformatics tools, the PANTHER (Protein ANalysis THrough Evolutionary Relationships) classification system is herein used to classify and identify the function of gene products. It has a large curated biological database of gene/protein families and their functionally related subfamilies designed to classify proteins and their genes for high-throughput analysis. At least one of the following parameters are used for the protein class analysis: ontology—One of "biological_process", "molecular_function" or "cellular_component".

The term "subject" as used herein refers to human, animal, plant, flatworms, microorganisms, planaria, fluids, food, emulsions, suspensions, soil, minerals, media, gas, liquid, gas mixtures, gas and liquid mixtures and/or to an object.

The term "substrate" as used herein refers to food or food product, liquid, beverage, suspension, biological culture, medium, growth medium, emulsion, biological tissue, biological organism, animal, plant, fluid, soil, minerals, media, gas, gas and liquid mixtures, gas mixtures, cells, tissue culture, organs and any combination thereof.

The term "microorganism" as used herein generally refers to a microscopic living organism, which may be single celled or multicellular. It is within the scope that microorganisms include yeast, bacteria, archaea, algae, corynebacteria, aerobic bacteria anaerobic bacteria, fungi, protozoa, virus, spores, hypha, *Candida*, prion, and any combination thereof. In specific embodiments, it includes industrial microorganisms, which refer to types of microorganisms such as bacteria and yeast that are used for large-scale production of industrial items. Industrial microbiology includes the use of microorganisms to manufacture food or industrial products in large quantities. Numerous microorganisms are used within industrial microbiology; including naturally occurring organisms, selected mutants or otherwise treated micro-organisms or genetically modified organisms (GMOs).

Non limiting examples of bacteria included within the scope of the present invention are *Listeria monocytogenes, Escherichia coli (E. coli), Salmonella*, bacteria of the Enterobacteriaceae family, bacteria of the Listeriaceae family, gram positive bacteria, gram negative bacteria, anaerobic bacteria, aerobic bacteria, *Bacillus subtillis, Staphylococcus aureus, Pseudomonas aeruginosa, Staphylococcus epidermidis, Staphylococcus haemolyticus, Enterococcus faecalis*, Clostridiaceae family, *Clostridium, Corynebacterium*, actinobacteria and any combination thereof.

The term "targeted microorganism" as used herein refers to a preselected microorganism which is exposed to the modified plasma output as compared to a non targeted control microorganism, which is of the same species but not exposed to the modified plasma output treatment.

The term "plasma modifying mechanism" relates to a mechanism that is positioned distally or remotely or externally to or separately from the NTP source and is configured and designed to convert or affect or influence or modify or to couple with the plasma discharge emitted from the plasma source. It is within the scope of the invention that the plasma modifying mechanism comprises (1) at least one magnetic material, and at least one piezoelectric material, and (2) at least one optical crystal material. According to core embodiments the plasma modifying mechanism provides modified plasma output having frequencies in the range of about 3 KHz to about 30 KHz. The aforementioned elements or materials of the plasma modifying mechanism at can be positioned within the system of the present invention in various configurations and arrangements as exemplified below.

The magnetic material or element is configured to provide electric and/or magnetic and/or electromagnetic and/or ferroelectric and/or ferromagnetic induced field.

In some embodiments, the magnetic material comprises at least one ferromagnetic element/material and at least one ferrimagnetic material/element and any combination thereof. Non limiting examples of ferromagnetic and ferrimagnetic materials include Chromium(IV) oxide, Cobalt, Dysprosium, Ferrite (iron), Ferrite (magnet), Iron(II,III) oxide, Magnetite ($Fe_3O_4$), α-ferrite (a Fe), Gadolinium, Gallium manganese arsenide, Iron, Neodymium magnet, Nickel, Permalloy, Rare-earth magnet, Samarium-cobalt magnet, Suessite, Yttrium iron garnet, ferromagnetic alloys, and any combination thereof.

The terms "ferromagnetic material" and "ferromagnetic element" used herein interchangeably refer to an element comprising a material which exhibit ferromagnetism in the broad sense that includes ferrimagnetism. According to certain aspects, the ferromagnetic element is selected from the group consisting of a permanent magnet, an electromagnet, a superconducting magnet, and any combination thereof. It is within the scope of the invention that such materials include elemental metals, and in other embodiments include alloys, oxides or other chemical compounds or mixtures thereof.

The term "ferroelectric element" used herein generally refers to a material having a property of a spontaneous electric polarization that can be reversed by the application of an external electric field. In other words, ferroelectric materials refer to materials that maintain a permanent electric polarization that can be reversed, or switched, in an external electric field. In specific embodiments, ferroelectric materials are pyroelectric and inherently piezoelectric. In certain embodiments, ferroelectric capacitors may have the combined properties of memory, piezoelectricity, and pyroelectricity. According to some aspects, piezoelectricity generally refers to the generation of a surface charge in response to the application of an external stress to a material. According to further aspects, pyroelectricity generally refers to a change in the spontaneous polarization of a material in response to a change in temperature.

It is within the scope of the present invention that ferroelectric materials and/or elements include ferroelectric polymers, particularly polyvinylidene fluoride, or polyvinylidene difluoride (PVDF). In alternative embodiments, ferroelectric elements included within the scope of the present invention may at least partially comprise PZT, lead zirconium titanate, ferroelectric oxides, Pb[Zr(x)Ti(1−x)]O3, PbZrO3, Barium Titanate (BaTiO3), (Ba, Sr)TiO3, Ba(1−x) Sr(x)TiO3 and any combination thereof.

The terma "piezoelectric material" and "piezoelectric element" used herein generally interchangeably refer to materials or certain crystals having the ability to generate a voltage in response to applied mechanical stress. Non limiting examples of piezoelectric material within the scope of the present invention include: Barium titanate (BaTiO3), Lead zirconate titanate (Pb[ZrxTi1−x]O3 with 0≤x≤1) (PZT), Potassium niobate (KNbO3), Sodium tungstate (Na2WO3), Ba2NaNb5O5, Pb2KNb5O15, Zinc oxide (ZnO). PZT (lead-zirconia-titanate or lead zirconate titanate) is the most common piezoelectric ceramic in use today. It is one of a large family of materials, whose structure change on the application of an electric current or, when strained, generate electricity. These specific piezo or ferroelectric effects have the properties that when a current is applied, a volume change occurs in the material. Lead zirconate titanate is an intermetallic inorganic compound with the chemical formula Pb[ZrxTi1−x]O3 (0≤x≤1), also called PZT, it is a ceramic perovskite material that shows a marked piezoelectric effect, meaning that the compound changes shape when an electric field is applied.

Thus it is herein acknowledged that according to one embodiment, an important piezoelectric material is lead zirconate titanate (PZT), which is part of the solid solution formed between ferroelectric lead titanate and anti-ferroelectric lead zirconate. Different compositions of PZT are used for different applications. For example, for memory applications, lead titanate ($PbTiO_3$) is preferred, whereas piezoelectric applications make use of the diverging piezoelectric coefficients associated with the morphotropic phase boundary.

It is further within the scope of the present invention that piezoelectric materials such as $Pb(ZrTi)O_3$ (PZT) or $PbTiO_3$ or any of the above mentioned piezoelectric materials are used in various arrangements and configurations as generators affecting the plasma discharge in which interactive electrical-mechanical energy conversion occurs based on piezoelectric effect.

The term "piezomagnetic element" used herein generally refers to antiferromagnetic crystals and materials, such as Piezomagnetic ferrite materials, magnetoelectric ceramic materials (e.g., Ba6¡ xR2x(Nb1¡ xFe2+x)O3), nickel, Ni—Fe alloy, V—Fe alloy, Fe—Co—Ni alloy, Ni—Cr—V alloy, (Fe, Cu system) Monel alloy; nickel ferrite, nickel-copper ferrite, nickel-zinc ferrite, composition systems including magnesium-manganese ferrite, nickel-cobalt ferrite etc. Piezomagnetizem may be characterized by a linear coupling between the system's magnetic polarization and mechanical strain. In a piezomagnetic, one may induce a spontaneous magnetic moment by applying physical stress, or a physical deformation by applying a magnetic field, see IEEE Std 319-1990 (1991), IEEE Standard on Magnetostrictive Materials: Piezomagnetic Nomenclature, which is incorporated herein as a reference. Moreover, it is further in the scope of the invention wherein at least one or more members of a group comprising magnetostrictive, electromagnetic, piezoelectric, and electrostrictive transducers and elements thereof are utilized.

The term "optical crystal material" used herein generally refers to a component at least partially comprising spherical and aspherical lenses or crystal materials. Non limiting examples of such materials include made from BK 7, UV grade fused silica, Infrared grade Calcium Fluoride (CaF2), Magnesium Fluoride (MgF2), AMTR, BaF2, Crystal Quartz, borosilicate, a glass ceramic material and Zinc Selenide materials. These materials have a wide transmission range, preferably from 0.2 µm up to 13 µm. In addition, specifications for important basic parameters such as index of refraction, transmission across various wavelength ranges, reflectance, Abbe Number, coefficient of thermal expansion, conductivity, heat capacity, density, Knoop hardness, and Young's modulus are publicly available. The at least one optical crystal material component of the system of the present invention can be arranged and configured in such a way as to bring to convergence or focusing of the plasma discharge and in combination with the magnetic and piezoelectric material provide or generate the modified plasma output having frequencies in the range of about 3 KHz to about 30 KHz.

According to certain aspects, the at least one optical crystal material component of the plasma modifying mechanism is configured to focus and enhance the modified plasma output. According to other aspects, the at least one optical crystal material is configured to centralized and/or gather and/or reduce loss of the generated modified plasma. According to a still other aspect of the invention, the at least one focusing element is configured to increase the efficiency of the discharged modified plasma.

It is within the scope that the system of the present invention comprises non transitory medium providing instructions for the plasma source to discharge the plasma in a predetermined pulsed profile. The pulse profile is effective in modulating (i.e. induction, upregulation or downregulation) of protein expression as well as production or generation or induction of proteins 'de-novo' in targeted microorganisms.

According to some embodiments, the pulse profile may be characterized by at least one of the following properties:

The terms "pulse cycle" and "cycle" are interchangeably herein defined as a predefined series of more than one "on pulse" followed by a pause. The pulse cycle duration is in the range of 0.15 to 1.68 min, particularly between 0.3 min to 1.5 min, more particularly between 0.5 min to 1.0 min.

The number of pulse cycles administered to the treated subject is in the range of 3 to 20 cycles, particularly 4 to 15 cycles.

The overall treatment session or exposure time of the treated subject (i.e. substrate hosting the microorganism) to the pulsed modified plasma is between about 0.45 min to about 34 min, particularly between about 0.6 min to about 25 min and more particularly between about 2.8 min and about 9.8 min per treatment.

Each pulse cycle comprises a series of 6-57 "on pulses" and 3-44 pauses. According to some embodiments, the duration of each "on pulse" is in the range of 1-8 seconds. According to further embodiments, the duration of each pause is in the range of 1-7 seconds.

Examples of pulse cycle profiles within the scope of the present invention include sequential number of pulses in the cycle ($1^{st}$ pulse, $2^{nd}$ pulse etc.). Each pulse comprises "on pulse" (e.g. defined in seconds) followed by a pause in seconds. A cycle or a pulse cycle is defined as a series or pattern of pulses (1st pulse, $2^{nd}$ pulse etc.).

In specific embodiments the number of pulses i in each cycle is at least 4 and up to 30, particularly, at least 6 and up to 30, more particularly at least 8 and up to 20 pulses in each cycle.

In some embodiments, the duration of one cycle or pulse cycle is between about 9 seconds and about 101 seconds, and more particularly between about 20 seconds and about 60 seconds.

According to other aspects, the number of cycles is administered according to the method or protocol of the present invention is between 2 and 50, particularly between 3 and 20.

It is further within the scope of the present invention that any combination of the above defined pulses can be used and applied for the modified plasma treatments of the present invention The terms "modified plasma output", "modified plasma discharge" and "modified plasma" as used herein interchangeably refer to a plasma or plasma beam comprising about 70-98% Argon, about 6-9% Nitrogen and about 1.5-2.5% Oxygen by % (wt.) and having discharge electric field in the range of 200-500 v/m at maximal flow, which is converted, coupled, or modified, or transformed, or generated by the plasma modifying mechanism of the present invention comprising at least one magnetic material, and at least one piezoelectric material, and at least one optical crystal material. The provided modified plasma output has frequencies in the range of about 3 KHz to about 30 KHz.

It is within the scope of the present invention that a modified plasma output refers to plasma oscillations influenced by or converted by the modifying plasma mechanism herein described. The modified plasma output is applied to a subject in a predetermined pulsed manner to produce specific protein expression profile and more particularly to induce generation or upregulation of specific proteins in the treated subject.

In one embodiment, the modified plasma output is applied to the subject in a predetermined pulsed mode, which is determined or more specifically adjusted according to the classification (i.e., taxonomic classification) of the treated subject and/or according to the desirable protein expression pattern or profile (e.g. induction or upregulation of specific proteins and protein pathways).

Examples of pulse profiles or cycles or patterns or parameters are provided within the scope of the present invention.

The term "fluid" as used herein generally refers to a substance that flows or continually deforms. In certain aspects, such substance continually deforms under an applied shear stress. The term "fluid" includes liquids, gases, liquid and gas mixtures, emulsions, suspensions, plasmas and, to some extent, plastic solids. Non limiting examples of "fluid" included within the scope of the present invention comprise any liquid or fluid or suspension such as water, oil, fuel, diesel, petroleum, beverage, raw oil, milk, honey, ketchup, blood, biological fluid, or other media, water in oil or oil in water mixtures, petroleum, fuel, fossil oil, liquefied petroleum gas, liquid petroleum gas or propane or butane or mixtures thereof, biofuels and products thereof, biodiesel and products thereof, hydrocarbon gas, gas, liquid and mixtures thereof, gas mixtures, and any combination thereof.

The term "unit discharge" as used herein refers to the voltage oscillation at a time.

It is according to another embodiment of the invention wherein the system and method is designed and operated to a remote or indirect treatment of the object; Gadri et al., 2000. Surface Coatings Technol 131:528-542 and Laroussi and Lu, 2005. Appl. Phys. Lett. 87:113902 and Montie et al., 2000. IEEE Trans Plasma Sci 28:41-50 and Topala and Nastuta, 2012. Plasma for Bio-Decontamination, Medicine and Food Security, NATO Science for Peace and Security Series A: Chemistry and Biology. ISBN 978-94-007-2851-6. Springer Science+Business Media B.V., p. 335 and Middelkoop et al. Burn wound healing: a role for plasma medicine and Vasile Nastuta et al., 2011. Journal of Physics D: Applied Physics. 44(10):105204; are publications incorporated herein by reference and non-limiting examples of NTP. This type of NTP in use is, e.g. a decaying plasma (afterglow)—longer lived chemical species. The NTP density and energy is e.g., of a moderate density—subject is located remote from electrodes. However, a larger volume of NTP can be generated using multiple electrodes. The spacing of target from NTP-generating electrode is approx. 5 to 20 cm; particularly 15 cm arcing (filamentous discharge) unlikely to contact subject at any power setting. In this system, there is no electrical conduction through target. The suitability for irregular surfaces is high—remote nature of NTP generation means maximum flexibility of application of NTP afterglow stream.

In other embodiments, the NTP in use is atmospheric pressure plasma jet (APPJ). The plasma may be generated using principles of corona discharge, DBD and microdischarges. Examples of applications of the NTP plasma or modified-plasma may include treatment of living cells or tissues, wound healing, cancerous cell apoptosis, blood coagulation i.e. on wounds, bone tissue modification, sterilization and decontamination. In such a case, the low temperature plasma jet is driven by high voltage pulses. In a specific embodiment, plasma jet works in helium. According to a main object, the system for administering modified plasma to a subject is applied to provide positive medical results related to recovery process of wounds i.e. of burned wounds, skin regeneration and re-epitelization.

It is according to another embodiment of the invention wherein the system is designed and operated to a direct treatment of the object; Lee et al., 2005. *Surface Coatings Technol* 193:35-38; Sladek and Stoffels, 2005. *J Phys D: Appl Phys* 38:1716-1721 and Stoffels et al., 2002. *Plasma Sources Sci. Technol*. 11:383-388 are publications incorporated herein as a reference and non limiting examples of systems designed and operated to a direct treatment. This type of NTP in use is, e.g., Active plasma—short and long-lived species. The NTP density and energy is e.g., Higher density—target in the direct path of a flow of active NTP. The spacing of target from NTP-generating electrode is approx. 1-5 cm; arcing can occur at higher power settings, can contact target. In this system, an electrical conduction through target is provided under a normal operation, but possible during arcing. The suitability for irregular surfaces is moderately high—NTP is conveyed to target in a directional manner, requiring either rotation of target or multiple NTP emitters.

It is according to another embodiment of the invention wherein the system is designed and operated in a method of electrode contact; Kelly-Wintenberg et al., 1999. *J. Vac. Sci. Technol*. A 17(4):1539-44; Laroussi et al., 2003. *New J Phys* 5:41.1-41.10; and Montenegro et al., 2002. *J Food Sci* 67:646-648 are publications incorporated herein as a reference and are provided as non limiting examples of embodiments included within the scope of the present invention. This type of NTP in use is, e.g., Active plasma—all chemical species, including shortest lived and ion bombardment. The NTP density and energy is e.g., highest density—target within NTP generation field. The spacing of target from NTP-generating electrode is approx. ≤1 cm; arcing can occur between electrodes and target at higher power settings. In this system, regarding the electrical conduction—the system is operatable e.g., if target is used as an electrode or if target between mounted electrodes is electrically conductive. The suitability for irregular surfaces is moderately low—close spacing is required to maintain NTP uniformity. However, electrodes can be shaped to fit a defined, consistent surface.

It is according to another embodiment of the invention wherein the system is designed and operated to discharge plasma affected by piezoelectric materials.

Examples of piezoelectric materials used in the system of the present invention include Barium titanate (BaTiO3), Lead zirconate titanate (Pb[ZrxTi1−x]O3 with 0≤x≤1) (PZT), Potassium niobate (KNbO3), Sodium tungstate (Na2WO3), Ba2NaNb5O5, Pb2KNb5O15, Zinc oxide (ZnO) or PbTiO$_3$. Such materials in combination with an optical crystal material are used for converting the NTP beam to a modified plasma output with the characteristics inter alia disclosed.

It is according to another embodiment of the invention wherein the system is designed and operated to discharge non-thermal plasma created by a plasma source (i.e. plasma jet) and exposed to the modifying plasma mechanism configured to discharge generated modified plasma output in a predefined pulsed manner.

It is according to another embodiment of the invention wherein the system is designed and operated to discharge non-thermal plasma coupled to a magnetic field. Liu Jingjing et al. 2005. *Plasma Science& Technology* Vol. 7 No. 5 3073-3077; and Zongbao Feng et al., 2012 *App. Phys. Lett* 101 041602 are publications incorporated herein as a reference and are provided as non-limiting examples of embodiments included within the scope of the present invention.

It is according to another embodiment of the invention wherein the system and method is designed and operated to discharge ferroelectric coupled non-thermal plasma field. Dunaevsky A. et al., 2001. *Journal of applied Physics* 90: 8 4108-4114; and Holzer F. et al., 2005. Plasma Chemistry and Plasma Processing 25:6 595-611, are publications incorporated herein as a reference and are provided as non-limiting examples of embodiments included within the scope of the present invention.

According to further aspects, it is within the scope of the present invention to disclose uses of a protein identified or produced by the system and method inter alia disclosed as a drug or pro-drug, food additive or food supplement, industrial enzyme and any combination thereof. Examples of such uses are herein provided.

Protein expression was modulated and proteins were 'de-novo' produced generated or induced, using the modified plasma discharge system of the current invention. Proteins expressed by the current invention have a potential usage in various medical indications, for research as well as by comprising new and unique supplements. The aforementioned paragraphs, list several of the herein expressed proteins in relation to their potential usage.

1. Proteins Expressed by Yeast:
   1.1. Proteins Related to Medical Indications
Proteins Related to Male Fertility
   P11792 Serine/Threonine Protein Kinase (SSTK) Gene SCH9—exists in the market as a partial recombinant protein. Human Ortholog is Q13188; Gene STK3 (STK3_Human).
   Q08220 Glutathione synthase (GSS) Gene GSH2—Does not exist in the market. Human Ortholog: P48637 Gene GSS (GSHB_Human).
   Q07979 Chromatin structure remodeling complex protein (RSC) Gene RSC58. Does not exist in the market.
   P36014 Glutathione peroxidase 1 (GSH px) Gene GPX1. (Exists in the market as recombinant protein) Human Ortholog P07203 Gene GPX1 (GPX1_Human).
Proteins Related to Skin Care/Regeneration
   Q02647 Dynein light chain 1 cytoplasmic. (Does not commercially produced) Human Ortholog P63167 Gene DYNLL1 (DYL1_Human).
   P32477 Glutamate cysteine ligase (GCL). (Exists in the market as partial recombinant) Possible Human Ortholog: P48506 Gene GCLC (GSH1_Human).
Proteins Related to Diseases Prevention (Mineral-Based and More)
   P38929 Calcium transporting ATPase 2 Gene PMC1 (Does not commercially produced) Human Ortholog P98194 Gene ATP2C1 (AT2C1_Human)
   Q12324 Calcium channel; Gene YVC1. (Exists as a recombinant protein) Human Ortholog
   Q08269 Magnesium transporter Gene ALR1 (Does not commercially produced)
   P38604 Lanestrol cynthase (LSS) Gene ERG7 (exists as partial recombinant protein) prevention from cataract Human Ortholog P48449 Gene LSS (ERG7_Human).
Anti-Viruses
   Q02793 Antiviral protein sk18.
   P35207 Antiviral helicase skI2.
   P53527 Antiviral helicase SLH1.
   Q03370 Peroxisomal membrane protein (anti-viral innate immunity).
   P15424 ATP dependent RNA helicase.
Proteins for Regulating Balancing or Maintaining the Immune System
   Q03370 Peroxisomal membrane protein (PMP) Gene PEX29 (Does not commercially produced) Human Orthologs: P40855 (Gene PEX19) (PEX19_Human) or Q9Y5Y5 Gene PEX16
   (PEX16_Human) or O43808 Gene SLC25A17 (PM34_Human).
   P32327 Pyruvate carboxylase 2 (PC) Gene PYC2. (Exists as partial recombinant protein)
   P15424 ATP dependent RNA helicase, mitochondrial MSS116 Gene MSS116.Exists as partial recombinant protein. Human Ortholog Q8IYB8 Gene SUPV3L1 (SUV3_Human).
   P40955 Chitin biosynthesis protein CHS6 Gene CHS6. (Exists as partial recombinant protein)
   P11792 Serine/Threonine protein kinase (SSTK) Gene SCH9. (Exists as partial protein) Human Ortholog is Q13188; Gene STK3 (STK3_Human).
   P22768 Arginino succinate synthase (ASS) Gene ARG1. (Exists as a recombinant protein) Human Ortholog P00966 Gene ASS1 (ASSY_Human).
Regulating/Modulating Focused Attention
   Q06608 Pyridoxamine-5'-phosphate oxidase homolg (PNPox or PPOX) Gene YPR172W. (Does not commercially produced).

P53824 Probably pyridoxal 5 phosphate synthase subunit SNZ2 (PLP) Gene SNZ2. Exists as a Probable pyridoxine biosynthesis recombinant protein—recombinant protein.

P04803 Trypthophan RNA ligase, mitochondrial TrpRS Gene MSW1. (Exists as a recombinant protein) Human orthlog Q9UGM6 (Gene WARS2 (SYWM_Human).

Neurological Diseases

Q01939 26S protease regulatory subunit 8 homolog (Gene RPT6). Linked to neurodegenerative diseases.

P32477 Glutamate—cysteine ligase (Gene GSH1). Deficiency in some cases lead to impaired neurological function Q08220 Glutathione synthetase (Gene GSH2). Severe form of Glutathione deficiency is linked to neurological systems P04803 Tryptophan—tRNA ligase, mitochondrial (MSW1). Deficiency linked to Multiple Sclerosis (MS), Alzheimer and Epilepsy Q05567 Sphingosine-1-phosphate lyase (S1P) (Gene DPL1). Modulation of S1P signaling is linked to Multiple Sclerosis (MS) treatment. Linked also to inflammatory properties Q08548 Lysophospholipid acyltransferase (Gene ALE1). Damage to brain membrane phospholipids has a role in pathogenesis of Alzheimer disease.

P48510 Ubiquitin domain-containing protein DSK2 (Gene DSK2). Linked to several neurodegenerative diseases Q6Q560 Protein ISD11 (Gene IDS11). Linked to Friedreich's ataxia causing progressive damage to the nervous system P15424 ATP-dependent RNA helicase MS S116, mitochondrial (Gene MSS116). Linked to neurological and rheumatic disorders and neurodegenerative diseases (ALS, SMA, Ataxia)

P23493 Mitochondrial biogenesis regulation protein 1 (Gene MBR1). Mitochondrial dis-function contributes to pathogenesis of neurodegenerative diseases Q12743 DER1-like family member protein 1 (Gene DFM1). Involved in neuronal diseases Q03280 E3 ubiquitin-protein ligase (Gene TOM1). Associated with neurodegenerative diseases and interact with neurological disease-associated proteins.

P32327 Pyruvate carboxylase 2 (Gene PYC2). Deficiency causing lactic acid and toxic compounds causes damage to the nervous system.

P39965 Probable proline—tRNA ligase, mitochondrial (Gene AIM10). Linked to progressive degenerative disease (Alpers) of the central nervous system P39001 Transcriptional regulatory protein UME6 (Gene UME6). Mutation in regulatory regions and in transcriptional factors are linked to neurological disorders and autoimmunity.

P40368 Nucleoporin NUP82 (Gene NUP82). Linked to neurological diseases and autoimmune dis-function.

Proteins Produced by the Method of the Present Invention and are not Commercially Available in the Protein Market Q07793 Transposon Ty1-DR4 Gag-Pol Polyprotein (gene TY1B-DR4). Resembles retroviruses structurally and functionally linked to the AIDs virus and has great potential as a basis for vaccine.

Q02793 Antiviral Protein SKI8 ((gene SKI8). Essential for controlling the propagation of M double-stranded RNA (dsRNA) and thus for preventing virus-induced cytopathology Q03834 DNA mismatch repair protein (gene ULS1). Has several functions highly relevant to carcinogenesis. Hereditary non-polyposis colon cancer (HNPCC) is a syndrome of deficient DNA mismatch repair and also Lynch syndrome and Gardner's syndrome.

Q08220 Glutathione synthase ((GSS), Gene GSH2). Glutathione synthetase deficiency is a disorder that prevents the production of an important molecule called glutathione. Severe form of Glutathione deficiency is linked to neurological systems; linked to skin care & regeneration Q05567 Sphingosine-1-phosphate lyase (Gene DPL1). Modulation of S1P signaling is linked to Multiple Sclerosis (MS) treatment. Linked also to inflammatory properties and mainly Crohn disease.

Q08269 Magnesium transporter ALR1, (Gene ALR1). Transports magnesium across the cell membrane.

Q01163 37 S ribosomal protein S23, mitochondrial (Gene RSM23). Required for maintenance of mitochondrial DNA.

Q07979 Chromatin structure-remodeling complex protein (Gene RSC58). Packages DNA into a smaller volume, prevent DNA damage, and control gene expression and DNA replication. Linked to male fertility.

Q03280 E3 ubiquitin-protein ligase (Gene TOM1). Associated with neurodegenerative diseases and interact with neurological disease-associated proteins.

Q06668 Methyltransferase OMS1, mitochondrial. Controls T-cell production, fighting infections and viruses and regulating the immune response.

Q02784 Monothiol glutaredoxin-5, mitochondrial (Gene GRX5): Required for normal iron homeostasis.

Proteins Produced by the Method of the Present Invention which are Available as Partial Recombinant Proteins in the Protein Market Q12018 Cell division control protein 53 (gene CDC53). Monitors cell division and kills cells if they have Wnt pathway defects. The p53 gene is a tumor suppressor gene, i.e., its activity stops the formation of tumors. The p53 protein is also a key player in apoptosis.

P35207 Antiviral helicase SK12 (gene SKI2). Functions as nucleic acid receptors in viral immunity.

P38604 Lanosterol Synthase (gene ERG7). An amphipathic molecule enriched in the lens and reverses protein aggregation in cataracts; also a key four-ringed intermediate in cholesterol biosynthesis.

P15424 ATP dependent RNA helicase, mitochondrial. Protects cells from apoptosis, sense viral infections and trigger the innate antiviral immune response; linked also to neurological, degenerative neurological diseases, and rheumatic disorders, and regulate aging and age-related diseases.

P06839 DNA repair helicase RAD3 (Gene RAD3). Plays an essential role in the cell viability. Involved in the maintenance of the fidelity of DNA replication.

Q12018 Cell division control protein 53 (Gene CDC53). Also known as TP53 or tumor protein; suppress cancer. P53 has been described as "the guardian of the genome"; Mutations in this gene are associated with a variety of human cancers, including hereditary cancers such as Li-Fraumeni syndrome.

P38339 RHO GTPase-activating protein (Gene RGD1). Modulates Rho mediated signaling pathways may lend themselves as targets for small molecule therapeutic agents against cancer. Associated also with Crohn disease.

P33417 Intrastrand cross-link recognition protein (Gene IXR1). Represents a major challenge for DNA replication and transcription by preventing DNA strand separation P32327: Pyruvate carboxylase 2 (Gene PYC2). Deficiency initiating lactic acid and toxic compounds to cause damage to the nervous system.

P39965 Probable proline—tRNA ligase, mitochondrial (Gene AIM10). Linked to progressive degenerative disease (Alpers) of the central nervous system.

P11792 Serine/Threonine Protein Kinase (SCH9) (Gene SCH9). Involved in regulation of lymphocyte migration and linked to male fertility.

P40955 Chitin biosynthesis protein CHS6 (Gene CHS6). An essential component of the cell walls.

P40368 Nucleoporin NUP82 (Gene NUP82). Linked to cellular and developmental defects and to neurological diseases and autoimmune dis-function, cardiovascular disorders and cancer.

P32477 Glutamate cysteine Ligase (Gene CHS1). Reduced levels of erythrocyte glutathione, leading to hemolytic anemia and in some cases, impaired neurological function.

Proteins Produced by the Method of the Present Invention which are Available as Recombinants P81451 ATP synthase subunit K, mitochondrial (Gene ATP19)

P04803 Tryptophan—tRNA ligase, mitochondrial (Gene MSW1)

Q12415 Transcription factor tau 55 kDa subunit (Gene TFC7)

P36014 Glutathione peroxidase 1 (Gene GPX1)

P35207 Antiviral helicase SKI2 (Gene SKI2)

P35197 ADP-ribosylation factor GTPase-activating protein GCS1

P22768 Argininosuccinate synthase (Gene ARG1)

Q12324 Calcium channel YVC1 (Gene YVC1)

P48524 Ubiquitin ligase-binding protein BUL1 (Protein BUL1)

Q92392 Transposon Ty1-OL Gag polyprotein (Gene TY1A-OL)

Q12470 Transposon Ty1-NL2 Gag polyprotein (Gene TY1A-NL2)

P38874 Elongator complex protein 5 (Gene IKI1)

Q12246 Sphingoid long chain base kinase 4 (GeneLCB4)

P53220 Mitochondrial import inner membrane translocase subunit TIM21

P16965 ATPase-stabilizing factor 15 kDa protein (Gene STF2)

P36036 RNA Annealing protein YRA2 (Gene YRA2)

P47822 Mediator of RNA polymerase II transcription subunit 21 (Gene SRB7)

Proteins Produced by the Method of the Present Invention for Research Purposes

P53824 Probable pyridoxal 5'-phosphate synthase subunit SNZ2 (NA, Name)

P21242 Probable proteasome subunit alpha type-7 (A; Name)

P38149 Probable di- and tripeptidase DUG2 Gene DUG2 (A, Partial)

P39965 Probable proline—tRNA ligase, mitochondrial—gene AIM10 (partial)

P39524 Probable phospholipid-transporting ATPase DRS2—gene DRS2 (NA, partial)

P40555 Probable 26S proteasome regulatory subunit p27—gene (NA)

P38994 Probable phosphatidylinositol 4-phosphate 5-kinase MSS4—GENE MSS4 (A-name, Partial)

P53336 Putative methyltransferase YGR283C (uncharacterized)

Q7LHD1 Putative covalently bound cell wall protein 22—gene CCW22 (uncharacterized cell wall);

Q04533 Putative cystathionine gamma-synthase YML082W—gene YML082W (NA)

Q04471 Putative peptidase YMR114C—gene YMR114C (NA)

Q12152 Putative serine/threonine-protein kinase YPL150W gene YPL150W (A, Partial)

Q08693 Putative zinc metalloprotease TRE2 (NA)

Specific Extracellular and Intracellular Proteins Produced by the Method of the Present Invention Linked to Diseases (after 4.9 Min. Treatment—2 Time Points)

P22768 Argininosuccinate synthase. Lack of Assay is observed in several types of cancers cell including pancreatic cancer, liver cancer and melanoma. Defects in ASSy causing ammonia and toxic substances to accumulate in the blood.

P14832 Peptidyl-prolyl cis-trans isomerase. Regulates many biological processes (protein folding, transcription, apoptosis, RNA processing) and has been implicated in a broad range of inflammatory diseases: Atherosclerosis; arthritis and viral infections. (Available as recombinant).

P49435 Adenine phosphoribosyltransferase 1: Catalyzed salvage reaction resulting in formation of AMP. Deficiency if not treated, can bring to kidneys failure (Non available).

P53327 Antiviral helicase SLH1. Involved in antiviral defense, preventing L-A dsRNA virus propagation by specifically blocking translation of viral mRNAs (Partial).

P10591 Heat shock protein SSA1: Has a protective effect against environmental stress (temperature, oxidation, toxic metabolites etc. (Partial)

P38886 26S proteasome regulatory subunit RPN10. A pivotal component of the ubiquitin Proteasome system and the cellular protein quality control. Deregulation of UPS contributes to pathogenesis of several neurodegenerative disorders (Non available).

Specific Supernatant and Pellet-Based Proteins Produced by the Method of the Present Invention Linked to Diseases (after 2.8 Min Treatment—3 Time Points/Examples)

3—TransposonTy1 Gag-pol polyproteins. Resembles retroviruses structurally and functionally and have the potential to be involved in producing vaccine for AIDS.

DNA mismatch repair protein. Has several functions that are highly relevant to carcinogenesis. Hereditary non-polyposis colon cancer (HNPCC) or, the most common form of hereditary colon cancer, is a syndrome of deficient DNA mismatch repair (MMR).

ATP-dependent mitochondrial RNA helicase. Protects cells from apoptosis, and in the form of RNA helicases, sense viral infections and trigger the innate antiviral immune response. The RNA helicases are also linked to neurological, degenerative neurological diseases, and rheumatic disorders, and regulate aging and age-related diseases.

Cell Division control protein 53. Monitors cell division and kills cells if they have Wnt pathway defects. The p53 gene is a tumor suppressor gene, i.e., its activity stops the formation of tumors. The p53 protein is also a key player in apoptosis.

Rho GTPase-activating protein RGD1. Modulates Rho mediated signaling pathways may lend themselves as targets for small molecule therapeutic agents against cancer. Associated also with Crohn disease.

Methyltransferase OMS1, mitochondrial. Controls T-cell production, fighting infections and viruses and regulating the immune response Antiviral protein SKI8 Gene SKI8. Essential for controlling the propagation of M double-stranded RNA (dsRNA) and thus for preventing virus-induced cytopathology Specific Supernatant and Pellet-Base Proteins Produced by the Method of the Present Invention Linked to Diseases (after 4.9 Min. Treatment—2 Time Points/Examples).

Argininosuccinate synthase ASSY (urea cycle). Lack of Assy is observed in several types of cancers cell including pancreatic cancer, liver cancer and melanoma. Defects in ASSy causing ammonia and toxic substances to accumulate in the blood Peptidyl-prolyl cis-trans isomerase. Regulates many biological processes (protein folding, transcription, apoptosis, RNA processing) and has been implicated in a broad range of inflammatory diseases: Atherosclerosis; arthritis and viral infections Adenine phosphoribosyltransferase 1. Catalyzed salvage reaction resulting in formation of AMP. Deficiency if not treated, can lead to kidneys failure.

Antiviral helicase SLH1. Involved in antiviral defense, preventing L-A dsRNA virus propagation by specifically blocking translation of viral mRNAs.

Heat shock protein SSA1. Has a protective effect against environmental stress (temperature, oxidation, toxic metabolites etc.)

26S proteasome regulatory subunit RPN10. A pivotal component of the ubiquitin Proteasome system and the cellular protein quality control. Deregulation of UPS contributes to pathogenesis of several neurodegenerative disorders Exemplified Functions of Proteins Produced by the Present Invention Q12018—cell division control protein 53—tumor/cancer suppressor. The p53 protein is also a key player in apoptosis.

Q03834—DNA mismatch repair protein. Binds to DNA mismatches thereby initiating DNA repair.

P32474—Protein disulfide-isomerase PDI. Allows proteins to quickly find the correct arrangement of disulfide bonds in their fully folded state (helps refolding).

Q08562—ATP-dependent helicase ULS1. Plays a role in the formation of DNA replication focal centers.

P06839—DNA repair helicase RAD 3. Plays an essential role in the cell viability.

Exemplified Functions of Proteins Produced by the Present Invention in *E. Coli*

Dihydrofolate reductase. Deficiency has been linked to megaloblastic anemia (an important class of therapeutic compounds, as evidenced by their use as anti-infective, antineoplastic, and anti-inflammatory drug.

Ubiquinone/menaquinone biosynthesis C-methyltransferase UbiE: Coenzyme Q 10 Nucleoside-diphosphate kinases. NDPKs, also NDP kinase. Linked to Alzheimer's disease and Down syndrome. Human brain nucleoside diphosphate kinase activity is decreased in Alzheimer's disease and Down syndrome.

Tryptophan synthase beta chain. As humans do not have tryptophan synthase, this enzyme has been explored as a potential drug target.

UTP—glucose-1-phosphate uridylyltransferase. Named also: UDP-glucose pyrophosphorylase linked to galactosemia a disorder that affects the development of newborns and children as they cannot metabolize the sugar galactose properly. It is speculated that overexpression of UDP-glucose pyrophosphorylase may relieve symptoms in humans with galactosemia. Also this enzyme has been found to be required for the biosynthesis of capsular polysaccharide, an important virulence factor of *Streptococcus pneumoniae*, a bacterial cause of pneumonia, bronchitis, and other breathing issues.

Malate synthase G. Perceived as a future drug target against tuberculosis and other microorganisms.

Thiamine-monophosphate kinase. Thiamin monophosphate kinase (ThiL) catalyzes the ATP-dependent phosphorylation of thiamin monophosphate (TMP) to form thiamin pyrophosphate (TPP), the active form of vitamin B 1.

1-Deoxy-D-xylulose 5-phosphate reductoisomerase—has been shown to be the molecular target for fosmidomycin, a promising antimalarial drug Multidrug Resistance Protein 4—MRP4. Protects Bone Marrow, Thymus, Spleen, and Intestine from Nucleotide Analogue-Induced Damage Pyridoxal phosphate homeostasis protein. Pyridoxal phosphate and pyridoxamine phosphate, the catalytically active forms of vitamin B(6), influence brain function by participating at stages in metabolism of proteins, lipids, carbohydrates, other coenzymes and hormones.

GTP cyclohydrolase 1 type 2 homolog (GCH1) GTP cyclohydrolase I, Ib, and II are potential targets for novel anti-infectives; has been shown to be a promising therapeutic target in ischemic heart disease, hypertension, atherosclerosis and diabetes Signal peptidase I—potential as a target for novel antibacterial agents Chorismate synthase. Considered to be potential targets for new antimicrobial chemotherapy/drug target/treatments for *Mycobacterium tuberculosis*

Quinone oxidoreductase 1 NQO1. Has a potential protective role in cardiovascular diseases and related conditions. It also possesses other important biological activities. These include anti-inflammatory effects, direct scavenging of superoxide anion radicals, and stabilization of p53 and other tumor suppressors.

In order to understand the invention and to see how it may be implemented in practice, a plurality of preferred embodiments will now be described, by way of non-limiting example only, with reference to the following examples.

Example 1

Effect of the System and Method of the Present Invention on Protein Production in Yeast Study Aims:

To determine which gene/protein pathways are modified or produced in yeast cells after exposure to pulsed modified plasma output of about 2.8 min (Study 1) or 4.9 min (Study 2) in comparison to gene/protein pathways in control samples of untreated yeast cells. The differences in the pathways produced or modified are also examined in pellet cells versus supernatant.

To determine which proteins are produced in yeasts cells after exposure to pulsed modified plasma output of about 2.8 min (Study 1) or 4.9 min (Study 2) as compared to proteins produced by non-treated yeast cells. The differences in the proteins produced in the yeast cells pellet and supernatant, and percentage of the produced proteins in existing databases are described.

Experimental Procedure:

Sampling and Sample Preparation:

*Saccharomyces cerevisiae* Meyen ex E.C. 1H-ansen yeasts and Cell Cultures (DSM No. 1333 (WDCM No. ATCC 9763) were used.

The yeast culture for the experiment was derived from a pre-culture yeast suspension in a stationary growth phase. From this suspension, $1 \times 10^7$ cells were used to inoculate the 48 h culture (20 g dextrose, 6.7 g Yeast Nitrogen Base (YNB) per 1 liter of distilled water) at 28° C. Within 48 h the yeast reached a titre of $1.13 \times 10^8$ cells per ml. At this time point, the yeast cells reentered the stationary growth phase and were physiologically synchronized. Immediately before the study treatment, the yeasts from the synchronized culture were diluted 1:10 with a fresh medium to allow growth to resume. At the start of the experiment, $1.13 \times 10^7$ yeast cells per ml, approximately 8.097 mg wet weight was achieved.

Following the 48 h incubation, samples to be used as treatment and control samples were formed. 12×5 ml samples were transferred into petri dishes (5.5 cm diameter) under sterile conditions without lid positioned exposed to the modified plasma output source. Dishes were placed on a rotary shaker for about 2.8 minutes, 4 pulse cycles (Study 1) or 4.9 min, 7 pulse cycles (Study 2) of modified plasma output exposure and corresponding mock treatments were performed (non-treated=control). The distance between the support or substrate on which the examined sample was put and the lower part of the modifying plasma mechanism was about 3 cm both for Study 1 and for study 2. Immediately after treatment (t0-time-point), samples were taken from the treated and non-treated t0 petri dishes for CFU/cell count and proteomics. The remaining yeast suspensions were transferred into 15 ml Falcon tubes, placing the tubes at 28° C. 60 stroke/minutes without shaking. In study 1: thirty minutes after treatment (time point t0.5 h) 0.2 ml were used for CFU and 2 ml were extracted from treated and non-treated vials (K1-3 and P1-3, respectively) for proteomics. The remaining vials continued their cultivation up to 1 hour after treatment (time point t1.0 h) and samples were taken as above for CFU/cell count and proteomics (K4-6 and P4-6, respectively). In study 2: samples were taken immediately following treatment (t0) and 3 hours following treatment (t3.0 h).

Immediately after the samplings for proteomics, the yeast cell suspensions were pelleted by centrifugation at 1400 rpm/5 min. The supernatant for each sample (time-point) was divided into equal parts creating 3 equal replicates and immediately frozen. The cell pellet was lysed using a Ribolyser tube for homogenization (two cycles at 6.5 m/sec) using a 375 µl of lysis buffer and then frozen for LCMS preparation. The supernatant and pellet samples were treated independently. Samples were formed as follows: 3 samples for each of the 3 time points for the treated and control samples, and for the supernatant samples and pellet samples. Frozen samples (cell lysate and supernatant) were stored at −80° C. prior to mass spectrometry preparation.

Sample Workup Procedure:

Ultra-deep frozen samples consisting of cell lysate samples and supernatant samples for each of the time-points (t0, t0.5 h, t1.0 h), were thawed on ice. The suspension was clarified from cell debris by centrifugation (10 min, 15,000*G). The clear supernatant from each sample was transferred into a fresh reaction tube and the protein content measured with Biorads RC DC protein quantification kit to ensure that identical amount of protein (50 µg) from each sample was used for the subsequent workup.

For the subsequent workup, 50 g protein from each sample was precipitated by acetone in a −20° C. freezer for 15 hours. Precipitated protein was pelleted by high speed centrifugation (10 min, 15,000*G) and the supernatant discarded. The yellowish-white protein pellet was resolubilized using 1% Rapigest® (Waters) in 25 mM ammonium bicarbonate buffer pH 8. Protein was denatured by adding dithiothreitol until a final concentration of 2.5 mM was achieved and heated to 60° C. for 10 min. The now reduced thiol groups were masked by iodacetamide (7.5 mM final concentration) at room temperature for 30 min. Digestion of protein was performed overnight by adding 2 g sequencing grade trypsin (Promega V511) for each sample. Finally, Rapigest® was removed by acid hydrolysis and sequential high speed centrifugation (3 times, 10 min/15,000*G). The digested protein solutions were desalted by solid phase extraction using zip tip nano columns (Thermo Scientific) augmented with additional 10 mg Aerys RP18 material (Phenomenex). After samples were eluted by 60% acetonitrile/MS grade water into HPLC vials with micro inserts (501, VWR) they were dried by 45 min vacuum centrifugation, resolubilized with mass spectrometry grade water and either immediately measured or snap frozen (−80° C.).

Mass Spectroscopy:

Samples prepared as described above were transferred to the MS lab on wet ice and immediately placed into the cooled (7° C.) sample compartment of the liquid chromatography system (Proxeon nanoLC II, Thermo Scientific). The LC system was equilibrated using appropriate settings (leak test, flush air, etc.) and 2 µl of each sample were directly injected in duplicates onto an Aerys RP18 3 µm column, 75 µm×200 mm (Phenomenex).

The digested proteins were separated by a 240 min gradient of acetonitrile (Fluka MS ultra gradient grade)/0.1% acetic acid (Roth, Ultrapure) and MS grade distilled water/0.1% acetic acid with a flow rate of 300 nL/min. The gradient began with 2% acetonitrile and ended with 70% acetonitrile/0.1% acetic acid/30% water/0.1% acetic acid. The separated analytes, i.e., the components of the digested proteins—the peptides-were transferred by ABsciex' nano ESI source (electrospray ionization) into an ABsciex TripleTOF5600 high-resolution time-of-flight mass spectrometer calibrated every 8 hours using yeast enolase digest (Waters).

Mass spectrometry was performed using an independent data acquisition mode (IDA experiment) as follows: all ions between 300 and 1250 mass/charge ration (m/z) were collected. All ions greater than 400 m/z and with a charge of ≥2 and an intensity of ≥100 counts per second were further fragmented by an energy impulse adjusted to the m/z and charge of each ion. Raw data were stored on a lossless server-based solution Mass Spectroscopy Data Analysis:

After acquiring the raw data as described above, data analysis was performed using the ProteinPilot 4.5 (ABsciex) software running on a Dell T7500 work station. A yeast database (generated from uniprot.org, as of Dec. 11, 2015) was used. Thereafter, protein IDs and protein quantitative data were calculated using PeakView, MarkerView, Wordpad, Uniprot.org, and MS Excel. The Panther (Protein ANalysis THrough Evolutionary Relationships) classification system was also used to classify and identify proteins, their genes, their functions and pathways.

Two Dimensional-Differential in Gel Electrophoresis (2D-DIGE)

Reference is now made to FIG. 1 presenting 2D-DIGE experimental setup and workflow as an embodiment of the present invention. In this embodiment, the first step is the creation of an internal standard, which is pooled from all samples. The second step is the fluorescent labelling of the different protein samples and the internal standard. Subsequent 2D-PAGE separates the proteins of two different samples (G200 and G300 labelled) and the internal standard (G100 labelled) by their pI and their molecular weight. After scanning and image analyses, expression data can be analysed via statistics.

More specifically, quantified protein extracts were minimally labeled using the Refraction-2D™-kit according to manufactures' suggestions (NH DyeAGNOSTICS GmbH, Halle/S., Germany) before electrophoresis. Individual sample extracts, 50 µg each (n=3 per group) were labelled with 400 pmol of either G-200 or G-300 dyes. As an internal standard, aliquots of all individual samples were pooled and labelled with G-100. The labelling of the samples was done by dye swapping such that protein extracts from two animals per group were labelled with G-200 and G-300 each.

Linear pH 4-7, 24 cm IPG strips (GE Healthcare) were rehydrated overnight in rehydration solution (urea 8 M, thiourea 2 M, pharmalyte 3-10 and 10×dithiothreitol (DTT)) containing two labelled samples (G-200 and G-300, each 50 µg) and the corresponding internal standard (G-100, 50 µg) for first dimension separation. The isoelectric focusing (IEF) was performed using a Multiphor II apparatus (GE Healthcare) with voltages ranging from 500 V to 3500 V for 17.50 h as suggested by the manufacturer. After IEF, the strips were reduced and alkylated in equilibration buffers containing 10% DTT w/v or 25% 2-iodoacetamide w/v, respectively, along with urea 8 M, Tris-HCl 1.5 M, pH 8.8, glycerol 87% w/v, and SDS 20% w/v before second dimension separation of proteins on 12.5% SDS-polyacrylamide gels in low fluorescent glass plates [Thiele T, Steil L, Gebhard S, Scharf C. et al. Profiling of alterations in platelet proteins during storage of platelet concentrates. Transfusion. 2007; 47:1221-1233. doi: 10.1111/j.1537-2995.2007.01255.x]

Image Analysis and Statistical Tests:

After separation in the second dimension, the gel images were recorded on a Typhoon 9400 Scanner (GE Healthcare) and analyzed with Delta 2D software version 4.0 (Decodon, Greifswald, Germany) [Hammer E, Phong T Q, Steil L, Klingel K. et al. Viral myocarditis induced by Coxsackievirus B3 in A.BY/SnJ mice: analysis of changes in the myocardial proteome. Proteomics. 2010; 10:1802-1818. doi: 10.1002/pmic.200900734.]. After matching the gels, the spot volumes were analyzed by Delta2D and the TMEV (Multi Experiment Viewer) statistic module of the same software package. Statistically significant differences in spot intensities among the groups consisting of four individual biological replicates each were calculated by one-way ANOVA applying Welch t-test with a p-value cutoff of ≤0.05.

nanoLC-ESI-MS/MS: In-Gel Digestion of Proteins and Mass Spectrometric Analysis

Preparative gels were run each with 450 µg of the pooled samples. Protein spots were visualized by colloidal coomassie staining as described in [Thiele T, Steil L, Gebhard S, Scharf C. et al. Profiling of alterations in platelet proteins during storage of platelet concentrates. Transfusion. 2007; 47:1221-1233. doi: 10.1111/j.1537-2995.2007.01255.x.], images were recorded and aligned with those of analytical gels in Delta2D. The protein spots displaying significant changes were excised from the preparative gels, destained with 30% acetonitrile/50 mM ammonium bicarbonate and after dehydration with 100% acetonitrile, the gel spots were subjected to proteolysis with trypsin (Promega, Madison, Wis., U.S.A.) overnight (16 h) at 37° C. The tryptic peptides were sequentially extracted from the gel pieces by ultra-sonication using initially 0.1% acetic acid in 50% acetonitrile and then 0.05% acetic acid in 80% acetonitrile.

The extracted peptides were separated on an Acclaim PepMap 100 reverse phase column (3 µm, 75 µm i.d×150 mm, LC Packings, Dionex, Idstein, Germany) with a nano-HPLC (EASY-nLC, Proxeon Biosystems A/S, Odense, Denmark) coupled with LTQ-Orbitrap-XL mass spectrometer (Thermo Electron, Bremen, Germany) using a 35 min linear gradient ranging from 5-60% ACN in 0.1% acetic acid (0 min-5% B-3 min-5%-23 min-35%-28 min-60%-30 min-100%-32 min-100%-35 min-0%) at a constant flow rate of 0.3 µL/min.

nanoLC-ESI-MS/MS: Identification of Proteins

DATABASE SEARCHING—Tandem mass spectra were extracted by Unspecified version Unspecified. Charge state deconvolution and deisotoping were not performed. All MS/MS samples were analyzed using Sequest (Thermo Fisher Scientific, San Jose, Calif., USA; version 1.0). Sequest was set up to search the uniprot-Saccharomyces_Cerevisiae database (unknown version, 9597 entries) assuming the digestion enzyme stricttrypsin. Sequest was searched with a fragment ion mass tolerance of 1.00 Da and a parent ion tolerance of 10.0 PPM. Oxidation of methionine and carbamidomethyl of cysteine were specified in Sequest as variable modifications.

CRITERIA FOR PROTEIN IDENTIFICATION—Scaffold (version Scaffold_4.7.2, Proteome Software Inc., Portland, Oreg.) was used to validate MS/MS based peptide and protein identifications. Peptide identifications were accepted if they could be established at greater than 95.0% probability by the Peptide Prophet algorithm (Keller, A et al Anal. Chem. 2002; 74(20):5383-92) with Scaffold delta-mass correction. Protein identifications were accepted if they could be established at greater than 95.0% probability and contained at least 2 identified peptides. Protein probabilities were assigned by the Protein Prophet algorithm (Nesvizhskii, Al et al Anal. Chem. 2003; 75(17):4646-58). Proteins that contained similar peptides and could not be differentiated based on MS/MS analysis alone were grouped to satisfy the principles of parsimony.

MALDI-TOF/TOF-MS: In-Gel Digestion of Proteins and Mass Spectrometric Analysis

Preparative two-dimensional gel electrophoresis was performed as previously described [T. Thiele, L. Steil, S. Gebhard et al., "Profiling of alterations in platelet proteins during storage of platelet concentrates," Transfusion, vol. 47, no. 7, pp. 1221-1233, 2007.]. Briefly, 450 µg of protein was pooled from treated and untreated samples of each condition (75 µg each) and added to the rehydration buffer. The resulting 2D-PAGE gels were stained with colloidal Coomassie brilliant blue according to the manufacturer's instructions (GE Healthcare). Digital documentation of the gel images was performed by a transmission light scan. Gel image analyses were performed with the Delta2D software package (Decodon GmbH) as described above. Spots of interest were processed for identification as described by Eymann et al. [C. Eymann, A. Dreisbach, D. Albrecht et al., "A comprehensive proteome map of growing Bacillus subtilis cells," Proteomics, vol. 4, no. 10, pp. 2849-2876, 2004.]. Briefly, spots were excised manually with a 2 mm picking head and transferred into 96-well microplates, which were loaded with 100 µL of Lichrosolv water in each well. Tryptic digestion was performed automatically in an Ettan Spot Handling Workstation (Amersham Biosciences) as well as the subsequent spotting of peptide solution onto MALDI targets. For peptide extraction, gel pieces were covered with 60 µL 50% v/v ACN/0.1% w/v TFA and incubated for 30 min at 37° C. Supernatants containing peptides were transferred into new microtiter plates. Peptide extraction was performed again with 40 µL of the same solution. Joined supernatants were now completely dried at 40° C. for 220 min. Peptides were dissolved in 2.2 µL of 0.5% w/v TFA/50% v/v ACN and 0.7 µL of each solution was spotted directly onto MALDI targets. Then, this sample solution was mixed with 0.4 µL of matrix solution by aspirating five times. After drying for 10-15 min, samples were measured using the MALDI-TOF-TOF instrument.

Matrix-Assisted Laser Desorption-Ionization Time-of-Flight Mass Spectrometry (MALDI-TOF-MS)

MALDI-TOF-MS measurements were performed with a Proteome-Analyzer 4800 (Applied Biosystems, Foster City, Calif., USA). Reflector mode was used in order to record the spectra in a mass range from 900 to 3700 Da with a mass focus to 2000 Da. Twenty-five sub spectra with 100 shots per subspectrum were accumulated for one main spectrum using a random search pattern. The standard peptide search tolerance was set to 50 ppm. The peak lists were created and searched automatically by using GPS-Explorer software package (Applied Biosystems, Foster City, Calif., USA). These peak lists were compared to a UniProt-SwissProt database (Rel. 51.5 restricted to human taxonomy) by the MASCOT search engine (Version 2.1). Positive identifications had to reach the following specifications: sequence coverage of at least 30% and a MOWSE-score of at least 49. Proteins and peptides, which failed to meet the 30% sequence coverage requirement, were reanalysed with more accurate MALDI-TOF-MS. The MALDI-TOF-MS/MS analyses were used for the five strongest peaks of the previous MS-spectrum. Here, 20 subspectra with 125 shots per subspectrum were accumulated using a random search pattern. The same tools were used for peak list interpretation. Results reaching a MOWSE-score of at least 49 in reflector mode (MALDI-TOF-MS) and being confirmed by subsequent measurement of the strongest peaks (MS/MS) were regarded as positively identified proteins. The confirmation by subsequent measurements (MS/MS) was particularly useful for protein identification in spots, which contained multiple proteins. Protein identifications and statistically relevant data were combined via unique spot-IDs using the MSRepo database software (Decodon, Greifswald, Germany).

Results:

Study 1

I. Total Proteins Quantitative Analysis

A large number of expressed proteins, both shared (expressed in both the treated and non-treated samples) and unique (expressed only in the treated—not in the control samples), were identified in the pellet-based and supernatant-based samples—treated and control samples (see Table 1).

TABLE 1

Total number of proteins (shared and unique) expressed in the supernatant and pellet samples of both treated and control samples

|  | Supernatant | Pellet | Total |
| --- | --- | --- | --- |
| Treated Samples | 4571 | 10918 | 15489 |
| Control Samples | 5937 | 11300 | 17237 |
| Total | 10508 | 22218 | 32726 |

Reference is now made to Table 2 showing the numbers of proteins which were uniquely expressed in the treated versus control samples for both the supernatant and pellet samples, for all time points (t0: immediately after treatment, t0.5 h: ½ hour after treatment and t1 h: 1 hour after treatment).

TABLE 2

Number of unique* proteins expressed in the supernatant and pellet samples for both treated and control samples

|  | Supernatant | Pellet | Total |
| --- | --- | --- | --- |
| Unique proteins in Treated Samples | 92 | 162 | 254 |
| Unique proteins in Control Samples | 242 | 219 | 461 |
| Total | 334 | 381 | 715 |

*Unique proteins in treated samples = Protein expressed only in the treated sample and not expressed in the non-treated/control samples
*Unique proteins in control samples = Protein expressed only in the non-treated sample and not expressed in the treated samples As can be seen from Table 2, 254 unique proteins were expressed in the treated groups at all time points examined: 92 in the supernatant sample and 162 in the pellet sample. This means that none of the 254 unique proteins was common to both the treated and non-treated samples in both the supernatant and pellet samples. The results also show a statistically significant relationship (Chi square=17.428 df=1. p<0.0001) between the number of proteins expressed and the protein source/location. More specifically, the results show that following exposure to the modified plasma output, significantly more unique pellet-based proteins were expressed than unique supernatant-based proteins (63.7% vs 36.3% respectively). This contrasts with the control samples where the number of unique pellet-based control proteins expressed was relatively similar to the number of supernatant proteins (53.3 and 46.7, respectively) which were expressed. This shows that the treatment modulated the relative ratios of unique proteins expressed in the supernatant versus pellet-based groups.

II. Analysis of Supernatant-Based and Pellet-Based Protein Expression

The UniProt database and Panther software were used to identify and describe protein class and protein pathways in the treated and control yeasts cells.

a. Treated Supernatant and Pellet Protein Classification Hits

Figure 2:
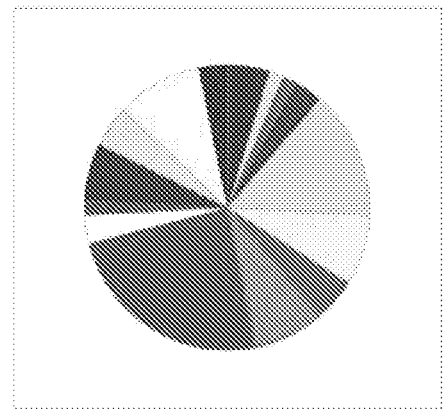
FIG. 2 are diagrams presenting protein classifications uniquely revealed in the treated supernatant cells.

Reference is now made to FIG. 2 describing the most significant protein classifications uniquely revealed in the treated supernatant cells. The total number of expressed genes in this group was 92 out of which 82 were identified, and the total number of protein class hits revealed was 62.

Figure 4B:
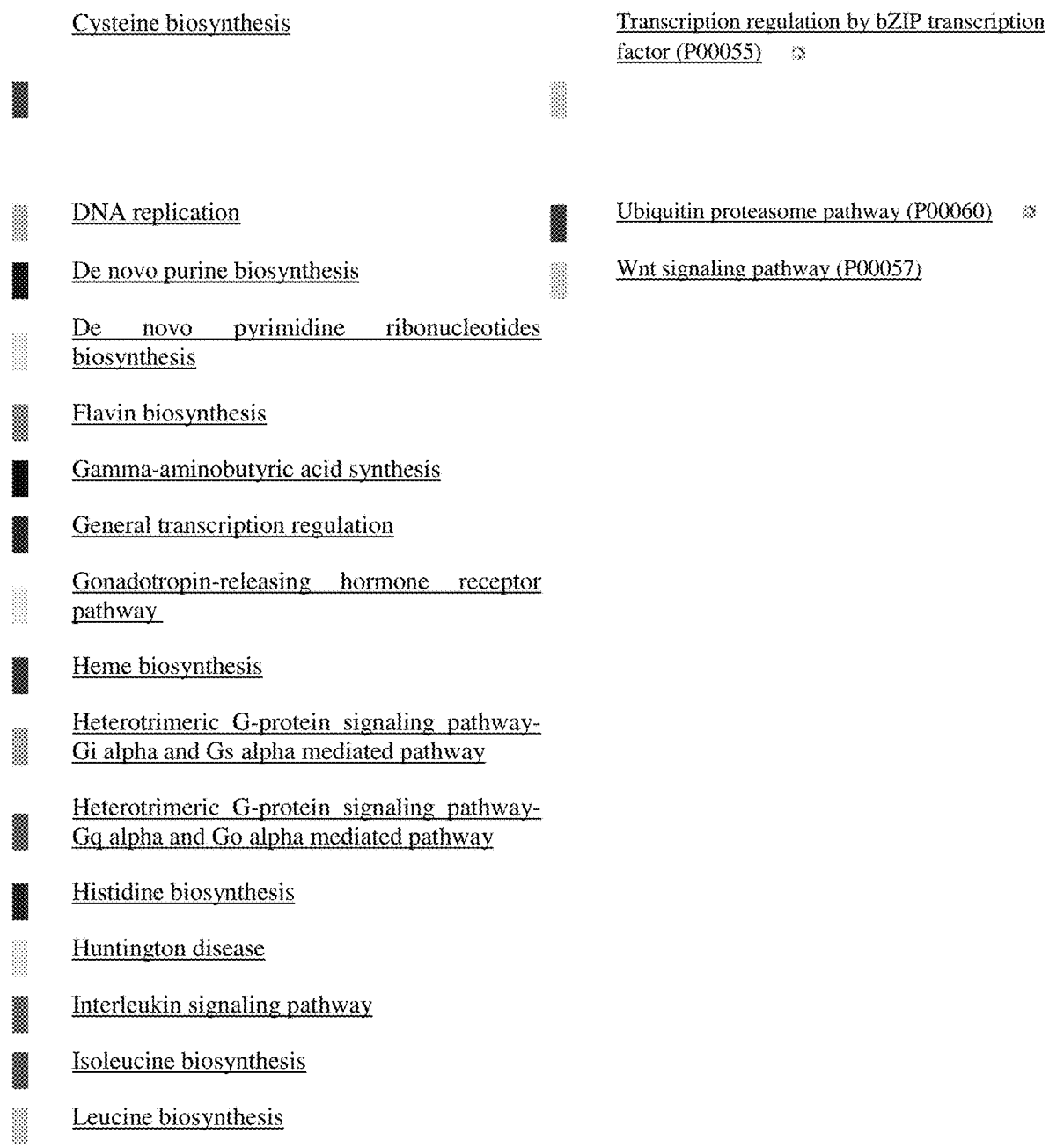

Reference is now made to FIGS. 3A-3B describing the most significant protein pathways uniquely revealed in the treated supernatant cells. The total number of expressed genes in this group was 82, and the total number of protein pathways classified was 15.

b. Treated and Control Supernatant-Based Pathways and Related Genes/Proteins:

Reference is now made to FIGS. 4A-4B describing the protein pathways in supernatant-based control (FIG. 4A) and treated (FIG. 4B) cells. The total number of expressed genes in the control group is 223 and in the treated group 82. The total number of protein pathway hits identified in the control group is 52, while in the treated group 12 pathways have been identified.

The results of FIG. 4 show that the number of pathways identified in the treated cells (panel A of FIG. 4), was substantially lower than the number of pathways identified in the non-treated control cells (panel B of FIG. 4). It should be noted two protein pathways have been uniquely identified in the supernatant treated cells and not in the supernatant control cells, namely the salvage pyrimidine ribonucleotides pathway with its putative associated gene/protein (UniProt number P18562: Uracil phosphoribosyltransferase, gene symbol FUR1) and the Methionine biosynthesis pathway (P02753). Pyrimidine nucleotides are essential as components of nucleic acids, as substrates for amino acid synthesis, and as energy sources. This pathway may be of biomedical interest for cancer cell therapy.

Interestingly, the results also show that there was a difference between the treated and control cells in terms of the number and types of proteins and genes within the common pathways. The results show that more genes are expressed in the pathways of the non-treated group of cells than in the treated group of cells. More detailed observation suggests, without wishing to be bound by theory that the genes/proteins of the treated group target particular functions while the genes/proteins of the control group are more generally associated with the pathways.

Several pathways showed the above mentioned pattern of results, namely fewer recognized compounds and genes/proteins expressed in the supernatant pathways of the treated cells compared with the non-treated cells' pathways. Examples of pathways with this pattern include: ubiquitin proteasome pathway, the Heme biosynthesis pathway, the Pyruvate metabolism pathways, the Wnt signaling pathway, the Transcription regulation by bzip transcription factor, and the General transcription regulation pathway. There was only one exception to this generalization regarding the supernatant-based proteins, and it showed the opposite pattern. The exception appears in the Parkinson disease pathway. In the Parkinson disease pathway, 3 genes/proteins were identified in the treated cells denoted by the UniProt classification system as P21242 (Probable proteasome subunit alpha type-7(PSA7) with a gene symbol PRE10); Q12018 (Cell division control protein 53 with gene symbol CDC53); and P11484 (heat shock protein SSB1 with gene symbol SSB1). In contrast, only one gene/protein was expressed in the non treated group P32379 (Proteasome subunit alpha type-5 with gene symbol PUP2).

The results demonstrate that exposure to the pulsed modified plasma output effected the structure and hence the functions of the identified pathways. This was indicated by differences between the treated and non-treated groups in terms of: a) the type of components activated within the pathways and their encoded genes and proteins; b) the number of proteins expressed within the pathway/s and their putative function; and c) the evolvement of a new pathway uniquely expressed in the treatment supernatant group and not expressed in the non-treated group.

c. Treated and Control Pellet-Based Pathways and Related Genes/Proteins:

Reference is now made to FIG. 5 describing the protein pathways in pellet-based control (A) and treated (B) cells. The total number of expressed genes in the control group is 194 and in the treated group 143. The total number of protein pathway hits identified in the control group is 35, while in the treated group 13 pathways have been identified.

The results of FIG. 5 demonstrate that significantly more pathways were identified in the non-treated pellet-based cells than in the treated cells. Interestingly, 7 new pathways have been identified in the treated cells compared with the non-treated cells; for example, three were alpha amino acid biosynthesis pathways for arginine, lysine and tryptophan, one (PGDF signaling pathway) concerned functions related to growth regulation and the survival of certain cell types during embryonal development and tissue repair in adults, and one (mRNA splicing) involved an important process in creating the mRNA.

Moreover, when similar identified pathways in the treated and non-treated cells were compared, entirely different genes/proteins were found in the pathways of the two cell groups. For example, with regard to Huntington disease, the pathway of the treated cells was recognizable by the dynein complex and denoted in the UniProt classification system as dynein light chain 1, cytoplasmic (Q02647), with the gene symbol DYN2. However, without treatment, one gene/protein was expressed, namely the proline oxidase gene/protein, denoted by the gene/protein P09368 encoded on gene Proline dehydrogonase, mitochondrial with the gene symbol PUT1. Similarly, regarding DNA replication: in the treated cells, the pathway component Primase was expressed by the gene/protein P10363 the DNA primase small subunit with the symbol PRI1, whereas in the non-treated group, the pathway component Pol Alpha was expressed by the P13382 gene/protein DNA polymerase alpha catalytic subunit A with the gene symbol POL1.

Interestingly, in the case of the cholesterol biosynthesis pathway, two pathway components were expressed in the treated cells, where each was encoded by one gene/protein (P38604 and P18900). On the other hand, in the non-treated cells, only one component was expressed with only one encoded gene/protein (P12684). In other words, as can be generally seen, the treatment mainly produced changes in the type rather than the number of the genes/proteins involved. Moreover, totally new pathways have been evolved post-treatment.

III. Description of Select Unique Proteins Produced Following Treatment a. Supernatant-Based Genes/Proteins in Treated Cells Reference is now made to Table 3 presenting a sample of 16 proteins uniquely expressed in the treated cells' supernatant. Examination of two different databases showed that these proteins are not available in the databases. Note that a "partial" protein is a protein which is in an incomplete state which requires further elaboration and production development. A "non-available protein" (denoted N.A.) means that these proteins are not included in the two searched databases. This means that these proteins are novel, not identified and remain a challenge for protein and drug development.

As shown in this study, at least 92 unique supernatant-based proteins have been identified in the treated cells. When the existing databases have been screened to determine the availability of the unique supernatant-based proteins, it was found that about 47% of the expressed proteins were available in the databases, 28% were denoted as partial, namely reproduced in a non-complete structure— henceforth these will be referred to as partially produced; and 25% were non-available, namely had not been reported or available despite their potential importance or value. Furthermore, the list of exemplary supernatant proteins of Table 3 shows that all the examples in the list are of great potential value to health and disease management.

TABLE 3

List of selected supernatant-based proteins uniquely produced in treated cells

| UniProt Number | Protein Title | Gene Symbol | Availability |
| --- | --- | --- | --- |
| Q03834 | DNA mismatch repair protein | ULS1 | N.A and Partial |
| Q99337 | Transposon Ty1-NL2 Gag-Pol Polyprotein | Ty1B-NL2 | Partial and Available |

TABLE 3-continued

List of selected supernatant-based proteins uniquely produced in treated cells

| UniProt Number | Protein Title | Gene Symbol | Availability |
|---|---|---|---|
| Q07793 | Transposon Ty1-DR4 Gag-Pol Polyprotein | TY!B-DR4 | N.A |
| Q03855 | Transposon Ty1-DR1 Gag-Pol Polyprotein | TY1B-DR1 | N,A |
| Q08562 | ATP-dependent helicase | ULS1 | N.A + Partial |
| P15424 | ATP dependent RNA helicase, mitochondrial | MSS116 | Partial |
| Q12018 | Cell division control protein 53 | CDC53 | Partial |
| P32477 | Glutamate cysteine Ligase | GSH1 | Partial |
| Q02784 | Monothiol glutaredoxin-5, mitochondrial | GRX5 | N.A |
| P21657 | Transcriptional activator protein | DAL81 | Partial |
| P39001 | Transcriptional regulatory protein | UME6 | partial |
| Q08492 | Bud site selection protein 21 | BUD21 | N,A |
| Q08693 | Putative zinc metalloprotease | TRE2 | N.A |
| Q01329 | Pre-tRNA-processing protein PTA1 | PTA1 | N.A |
| P39077 | T-complex protein 1 subunit gamma | CCT3 | Partial |
| P32477 | Glutamate-cysteine ligase | GSH1 | Partial |
| Q12505 | Serine/threonine-protein kinase SKS1 | SKS1 | Partial |

For example, a deficient expression of a DNA mismatch repair protein often occurs in cancers and contributes to numerous mutations usually found in cancers. Moreover, DNA mismatch repair proteins have several additional functions which are highly relevant to carcinogenesis. These include: DNA damage surveillance, prevention of recombination between non-identical sequences, involvement in meiotic processes. Another example relates to RNA helicases, which are known to sense viral infections and trigger an innate antiviral immune response. They are also linked to neurological and rheumatic disorders, neurodegenerative diseases (ALS amyotrophic lateral sclerosis and ataxia-oculomotor apraxia type-2 (AOA2), spinal muscular atrophy (SMA)), cancer, and chronic diseases. The transposons TY1 gag-pol polyproteins, namely, the mobile genetic elements that can multiply in the genome using a variety of mechanisms, including a mechanism of replication which is shared with retroviruses, is linked to the AIDs virus and has great potential as a basis for vaccine. Finally, the glutamate cysteine ligase whose deficiency is linked to hemolytic anemia and in some cases to impaired neurological functions.

b. Selected Pellet-Based Genes/Proteins in Treated Cells:

Reference is now made to Table 4 presenting a sample of 16 proteins expressed in the pellet of the treated cells. A survey of protein databases shows that these proteins of Table 4 are not readily available within the searched existing protein databases. Some of these proteins are completely unavailable and some have only been partially reported. When the availability of the pellet-based proteins (N=162) in the treated cells was checked against protein databases, it was found that about 52% of the expressed proteins were found in existing databases, 27% were only partially available, and 21% were non-available despite their potential importance and value. This shows that, a large percentage of the proteins identified in the cell pellet as a result of the treatment with the pulsed modified plasma output are linked to health and disease states and are firstly identified by the present invention.

Table 4 also presents examples of proteins found in the pellet. It can be seen that most if not all are significant for both health and disease states and disease management. For example, the probable proline tRNA ligase gene mitochondrial encodes a putative member of the class II family of aminoacyl-tRNA synthetases. These enzymes play a critical role in protein biosynthesis by charging tRNAs with their cognate amino acids. Mutations have been found in this gene in some patients with Alpers-Huttenlocher syndrome—a progressive degenerative disease of the central nervous system occurring mostly in infants and children. There is no cure at present for Alpers' disease and no way of slowing its progression. Another example is the Nucleoporin NUP82 gene. Nucleoporin genes form part of the nuclear pore complexes (NPCs) and alterations in NUP genes are associated with several human neoplastic and non-neoplastic diseases. Heart failure is also associated with changes in the levels and distribution of specific NUPs. And finally, lanosterol synthase is an amphipathic molecule which is enriched in the lens and reverses protein aggregation in cataracts. It is synthesized by lanosterol synthase (LSS) in a key cyclization reaction of a cholesterol synthesis pathway.

TABLE 4

Selected pellet-based proteins uniquely produced in treated cells

| UniProt Number | Protein Title | Gene Symbol | Availability |
|---|---|---|---|
| Q02973 | Antiviral Protein SKI8 | SKI8 | N.A |
| P35207 | Antiviral helicase | SKI2 | Partial |
| P32504 | Centromere DNA-binding protein complex CBF3 subunit A | CBF2 | Partial |
| P38604 | Lanosterol Synthase | ERG7 | Partial |
| P32908 | Structural maintenance of chromosomes protein 1 | SMC1 | Partial |
| P53341 | Alpha-glucosidase MAL12 | MAL12 | Partial |
| Q03280 | E3 ubiquitin protein ligase TOM1 | TOM1 | N.A |
| Q04401 | Succinate Dehydrogonase assembly factor 3, mitochondrial | SDH7 | N.A |
| Q02884 | Elongator complex protein 4 | ELP4 | N.A |
| P40368 | Nucleoporin NUP82 | NUP82 | Partial |
| Q99207 | Nucleolar complex protein 14 | NOP14 | Partial |
| Q08237 | RNA exonuclease 4 | REX4 | N.A |
| Q06668 | Methyltransferase OMS1, mitochondrial | OMS1 | N.A |
| Q12321 | Mediator of RNA polymerase II transcription subunit 1 | MED1 | Partial |
| P39524 | Probable phospholipid-transporting ATPase DRS2 | DRS2 | N.A and Partial |
| Q12505 | Serine/threonine-protein kinase SKS1 | SKS1 | Partial and Available |

IV. Metabolic Processes in Treated and Non-Treated Cells

In both the supernatant and pellet the metabolic processes in the treated and non-treated yeasts cells were examined using the Panther software. Comparison of the treated and non-treated cells found a similarity in the identified biochemical processes, for example: biosynthetic processes, catabolic processes, coenzyme metabolite; generation of precursor, metabolites and energy; nitrogen compound metabolic processes, phosphate compound metabolic processes; primary metabolic processes and sulfur compound metabolic processes. Another process, linked to vitamin metabolic processes was observed in the supernatant control group and both pellet groups (treated and non-treated) but not in the treated supernatant group. There were also differences in the number and types of proteins involved in these metabolic processes between the treated versus the control groups and in the supernatant versus the pellet groups.

Different types of cellular processes were also involved in the treated and non-treated supernatant and pellet samples. Table 5 shows that the gene/proteins expressed in the supernatant samples were involved in less cellular processes than the gene/proteins in the control group and pellet cells. This demonstrates that the number of genes/proteins in the treated supernatant group and the number of functions observed were lower compared with the control group.

TABLE 5

Cellular processes identified in supernatant and pellet samples in the treated and non-treated groups based on Panther analysis

|  | Supernatant | Pellet |
| --- | --- | --- |
| Treated | Cell communication (3)* | Cell communication (5) |
|  | Cell cycle (1) | Cell cycle (9) |
|  |  | Cellular component movement (2) |
|  |  | Chromosome segregation (5) |
|  |  | Cytokinesis (1) |
| Non-Treated | Cell communication (3) | Cell communication (5) |
|  | Cell cycle (5) | Cell cycle (17) |
|  | Cytokinesis (2) | Chromosome segregation (3) |
|  | Cellular component movement (2) |  |

*Number of genes/proteins involved

Table 6 presents another example of the biochemical metabolic processes involved in the post-translational protein modification processes in both the treated and non-treated groups of the supernatant and pellet cells. The table shows that in the treated groups (supernatant and pellet) the expressed genes/proteins are related to two types of protein modification processes.

Table 6 also demonstrates the different types of expressed proteins engaged in the post-translational protein modification processes.

TABLE 6

Cellular protein modification processes in supernatant and pellet samples in treated and non-treated samples based on Panther analysis

|  | Supernatant | Pellet |
| --- | --- | --- |
| Treated | Protein Phosphorylation P26570/PPZ1 | Protein Phosphorylation P26570/PPZ1; P35182/PTC1; P38149/DUG2 |
|  | Protein Glycosylation P33767/WPB1 | Protein Lipidation Q02887/ATG21; P33154/GOP1 |
| Non-Treated | Protein Phosphorylation P23287/CNA1 | Protein Phosphorylation P27614/CPS1; P38930/CKB2 |
|  | Protein Lipidation Q02887/ATG21 | Protein Lipidation P38875/GPI16 |
|  | Protein Methylation P38074/HMT1 | Protein Methylation Q12504/RKM4; P53738/TRM112 |
|  |  | Protein Acetylation Q06504/NAT3; Q02197/MAK10 |

V. Summary

The study shows that a large number of valuable proteins (254) can be produced after exposure of the yeasts cells to the pulsed modified plasma output for less than 3 minutes. The produced or upregulated proteins are linked to protein complexes and pathways and associated with different health and disease conditions. The study also shows that exposing yeasts cell to the pulsed modified plasma output altered the number of the protein/genes pathways, their internal make-up (components) and structure, and thus potentially achieved less complex and more efficient pathways in terms of information flow. Furthermore, the exposure of the yeast cells to the pulsed modified plasma output generated new pathways not found in the metabolic processes of the comparable non-treated yeast cells. The study thus demonstrates the possibility of restructuring or modulating protein expression, protein networks and cellular processes in microbial cells, production generation or induction of proteins 'de-novo', and producing different types of proteins without using genetic engineering methodologies.

It is crucial to underscore that most of the pathways generated/modified by exposure to the pulsed modified plasma output, are medical health-linked pathways. The analysis of the pathways produced in this study indeed shows these pathways to be strongly associated with diseases and potential treatment of medical conditions. For example: the wnt signaling pathway: an evolutionarily-conserved pathway that regulates crucial aspects of cell fate determination, cell migration, cell polarity, neural patterning, and organogenesis during embryonic development, plays a key role in skeletal development and homeostasis. Studies have shown a strong and even causative link between deregulated Wnt signaling pathways and human disease. Wnt signaling is recognized for its role in carcinogenesis mostly associated with benign and malignant breast tumors, though it has also been linked with other cancers. More recently, the Wnt pathway has been linked to embryonic development and the pathogenesis of lung diseases, particularly lung cancer, pulmonary fibrosis, and pulmonary arterial hypertension. It has been suggested that Wnt pathway components might be appropriate therapeutic targets for manipulating clinical skeletal responses and/or used as a potential bio-drug. These therapeutic targets could treat osteoporosis, enhance skeletal repair, and even regenerate skeleton components damaged by disease or trauma.

Other pathways identified in this study have regulatory functions with considerable bio-drug potential. For example: the pyruvate metabolic pathway can offer an effective strategy or approach for controlling radiation-induced skin damage. The platelet-derived growth factor (PDGF) signaling pathway regulates critical events for fibrous tissue deposition and angiogenesis. It regulates post-infraction repair and events critical to fibroblast migration, proliferation, and activation, and plays a key process in vascular maturation. The gonadotropin-releasing hormone (GnRH) pathway plays a key role in both central and peripheral reproductive regulation and in modulating the biochemical, pathological, and cognitive changes associated with aging and age-related neurodegenerative disorders. The DNA replication pathway is mainly relevant to different pathological states associated with dysfunctional and/or unregulated activity leading to uncontrollable DNA replication. The significance of uncontrolled DNA replication for pathological states including cancer, autoimmune diseases, and viral/bacterial infections are well-established.

The ubiquitin proteasome pathway is recognized for its broad cellular regulatory function and as a quality control system (controlling protein degradation and denaturation). It is also recognized as a "secondary antioxidant" involved and affected in several diseases, including neurodegenerative diseases (Alzheimer or polyglutamine repeat diseases), cellular atrophies and malignancies. The salvage pyrimidine ribonucleotides include pyrimidine nucleotides which are essential components of nucleic acids and serve as substrates for amino acid synthesis and as energy sources. This pathway is of biomedical interest for cancer cell therapy. Finally, it is important to highlight the very special biosynthesis pathways of the three amino acids: arginine, lysine, and tryptophan, pathways which also have health and therapeutic values. For example tryptophan is an amino acid linked to the regulation of immune tolerance and anti-tumor immune responses and is required both for protein synthesis and producing other compounds, including the neuro-hormone serotonin and the vitamin nicotinic acid. Lysine is thought to be involved in the response to oxidative stress because of its role in cell wall formation and protein degradation. And although arginine is considered a nonessential amino acid in healthy humans, it is thought to be essential under certain physiological circumstances and in some disease states, especially in rare forms of cancer.

Similarly, the individual proteins produced in this study which are directly or indirectly associated with the pathways identified also have strong association with health and medical conditions, and hence offer very promising potential as bio-drugs or treatments. Examples of these proteins are: the 3 TransposonTy1 Gag-pol polyproteins, which resemble retroviruses structurally and functionally and have the potential to be involved in the production of vaccine for AIDS; the DNA mismatch repair protein which has several additional functions that are highly relevant to carcinogenesis; the ATP-dependent mitochondrial RNA helicase, associated with mitochondrial DNA, which may protect cells from apoptosis, and in the form of RNA helicases sense viral infections and trigger the innate antiviral immune response. The RNA helicases are also linked to neurological, degenerative neurological diseases, and rheumatic disorders, and regulate aging and age-related diseases; and finally, the intrastrand cross-link recognition protein which represents a major challenge for DNA replication and transcription by preventing DNA strand separation.

The present invention teaches to produce unique proteins that either do not exist in available databases or partially reported. A representative example of the proteins that this study produced which are described as "non-available" or "partially produced" may be found in Tables 3 and 4.

One of the most surprising and important findings in this study is the similarities and differences between the supernatant and pellet cell samples in the proteins produced and pathways described. The study found important differences—in the number and type of genes/proteins generated when targeting the supernatant and pellet cells for protein production. The supernatant and pellet cells had only seven proteins in common. The study also shows that the treated pellet samples and the supernatant samples generated completely different novel pathways.

It is further noted that there were major differences in the number of cellular processes involved in the protein production processes of the supernatant and the cell pellet. Five cellular processes have been identified in the pellet yeast cells: cell communication, cell cycle, cellular component movement, chromosome segregation, and cytokinesis. On the other hand, two main cellular processes have been identified in the supernatant (cell communication and cell cycle). The experiment showed that by application of the pulsed modified plasma output a significant effect on the treated supernatant samples (compared to the untreated control samples) is achieved.

The present invention provides a system and method for inducing a range of proteins and pathways with direct and indirect therapeutic functions potentially affecting a variety of diseases and medical conditions. The stimulated pathways include: anti-stress defense mechanisms, regulatory control and signaling pathways which are associated with protein degradation and misfolded proteins, transcriptional process regulation, cell cycle processes, biological and metabolic processes, and more.

The study disclosed herein describes the unique proteomic outcome of applying the pulsed modified plasma output, generated by the system of the present invention, to yeast. The present invention provides a non GM method for producing a variety/milieu of medical-linked proteins for use in therapeutic applications. The method can be adjusted to different organisms (i.e. using different pulse profile, pulse duration) and the produced proteins are not considered as recombinant proteins, but are naturally produced in vivo following exposure to the pulsed modified plasma output.

Study 2

Study 2 was performed using the same methodology of study 1, with several modifications: Number of pulse cycles in Study 2 is seven pulses, compared to four pulse cycles in Study 1. Time points for testing are immediately following treatment (t0) and at 3 hours following treatment (t3.0 h).

I. Description of Select Unique Proteins Produced Following Treatment

Reference is now made to Table 7 presenting a list of pellet proteins unique to the treated samples (not identified in the pellet control samples). The list includes treated-cells unique pellet proteins identified immediately after treatment (t0) and 3 hours following treatment (t3.0 h).

TABLE 7

| Pellet proteins identified in the treated samples and not in the control samples | |
|---|---|
| Accession Number | Pellet Proteins identified only in treated samples N = 102 |
| | 45 pellet proteins below expressed immediately after the treatment |
| CYC1_YEAST | Cytochrome c iso-1 |
| GYS2_YEAST | Glycogen [starch] synthase isoform 2 |
| ILV6_YEAST | Acetolactate synthase small subunit, mitochondrial |
| MDM38_YEAST | Mitochondrial distribution and morphology protein 38 |
| FSH1_YEAST | Family of serine hydrolases 1 |
| RSP5_YEAST | E3 ubiquitin-protein ligase RSP5 |
| SEC63_YEAST | Protein translocation protein SEC63 |
| 6PGD2_YEAST | 6-phosphogluconate dehydrogenase, decarboxylating 2 |
| RPN6_YEAST | 26S proteasome regulatory subunit RPN6 |
| CBF5_YEAST | H/ACA ribonucleoprotein complex subunit 4 |
| IF2B_YEAST | Eukaryotic translation initiation factor 2 subunit beta |
| RS25A_YEAST | 40S ribosomal protein S25-A |
| SFM1_YEAST | Protein arginine N-methyltransferase SFM1 |
| RL6B_YEAST | 60S ribosomal protein L6-B |
| RL34A_YEAST | 60S ribosomal protein L34-A |
| CORO_YEAST | Coronin-like protein |
| FRA1_YEAST | Putative Xaa-Pro aminopeptidase FRA1 |
| SIP2_YEAST | SNF1 protein kinase subunit beta-2 |
| DLHH_YEAST | Putative carboxymethylenebutenolidase |
| PP2C2_YEAST | Protein phosphatase 2C homolog 2 |
| PIC2_YEAST | Mitochondrial phosphate carrier protein 2 |
| RL16A_YEAST | 60S ribosomal protein L16-A |
| SIP18_YEAST | Protein SIP18 |
| ATP14_YEAST | ATP synthase subunit H, mitochondrial |
| PMT1_YEAST | Dolichyl-phosphate-mannose--protein mannosyltransferase 1 |
| YFI6_YEAST | Uncharacterized protein YFR016C |
| SGPL_YEAST | Sphingosine-1-phosphate lyase |
| IML2_YEAS7 | Mitochondrial outer membrane protein IML2 |
| DSD1_YEAST | D-serine dehydratase |
| GET4_YEAST | Golgi to ER traffic protein 4 |
| FAT1_YEAST | Very long-chain fatty acid transport protein |
| GLO3_YEAST | ADP-ribosylation factor GTPase-activating protein GLO3 |
| HOG1_YEAST | Mitogen-activated protein kinase HOG1 |
| SDHF4_YEAST | Succinate dehydrogenase assembly factor 4, mitochondrial |
| YN8B_YEAST | UPF0674 endoplasmic reticulum membrane protein YNR021W |

TABLE 7-continued

Pellet proteins identified in the treated samples and not in the control samples

| Accession Number | Pellet Proteins identified only in treated samples N = 102 |
|---|---|
| MG101_YEAST | Mitochondrial genome maintenance protein MGM101 |
| AIM46_YEAS7 | Altered inheritance of mitochondria protein 46, mitochondrial |
| COX20_YEAST | Cytochrome c oxidase protein 20, mitochondrial |
| BZRD_YEAST | Benzil reductase ((S)-benzoin forming) IRC24 |
| RT102_YEAST | Regulator of Ty1 transposition protein 102 |
| VPS60_YEAST | Vacuolar protein-sorting-associated protein 60 |
| HIBCH_YEAST | 3-hydroxyisobutyryl-CoA hydrolase, mitochondrial |
| YAP1_YEAST | AP-1-like transcription factor YAP1 |
| CSL4_YEAST | Exosome complex component CSL4 |
| YEY2_YEAST | Uncharacterized protein YER152C |
| | 57 Pellet proteins below expressed 3 hours after the treatment |
| SNU13_YEAST | 13 kDa ribonucleoprotein-associated protein |
| IPB1_YEASX | Protease B inhibitor 1 |
| H2B1_ASHGO | Histone H2B.1 |
| NCL1_YEAST | Multisite-specific tRNA: (cytosine-C(5))-methyltransferase |
| DEF1_YEAS2 | RNA polymerase II degradation factor 1 |
| COX13_YEAST | Cytochrome c oxidase subunit 6A, mitochondrial |
| THIK_YEAST | 3-ketoacyl-CoA thiolase, peroxisomal |
| SIM1_YEAST | Probable secreted beta-glucosidase SIM1 |
| TIM9_YEAST | Mitochondrial import inner membrane translocase subunit TIM9 |
| NNRD_YEAST | ATP-dependent (S)-NAD(P)H-hydrate dehydratase |
| MMS2_YEAST | Ubiquitin-conjugating enzyme variant MMS2 |
| CCW14_YEAST | Covalently-linked cell wall protein 14 |
| SDS22_YEAST | Protein phosphatase 1 regulatory subunit SDS22 |
| DDI1_YEAST | DNA damage-inducible protein 1 |
| PSB4_YEAST | Proteasome subunit beta type-4 |
| RTN2_YEAST | Reticulon-like protein 2 |
| ABF2_YEAST | ARS-binding factor 2, mitochondrial |
| ASF1_YEAST | Histone chaperone ASF1 |
| TSR1_YEAST | Ribosome biogenesis protein TSR1 |
| TRX3_YEAST | Thioredoxin-3, mitochondrial |
| ERG2_YEAST | C-8 sterol isomerase |
| YG3A_YEAST | Uncharacterized protein YGR130C |
| YNB0_YEAST | Uncharacterized phosphatase YNL010W |
| PWP1_YEAST | Periodic tryptophan protein 1 |
| AIM2_YEAST | Protein AIM2 |
| YRA1_YEAST | RNA annealing protein YRA1 |
| KYNU_YEAST | Kynureninase |
| MDG1_YEAS1 | Signal transduction protein MDG1 |
| CSR1_YEAST | Phosphatidylinositol transfer protein CSR1 |
| ERV29_YEAST | ER-derived vesicles protein ERV29 |
| BPL1_YEAST | Biotin--protein ligase |
| YJF5_YEAST | LOG family protein YJL055W |
| SOL2_YEAST | 6-phosphogluconolactonase-like protein 2 |
| HRB1_YEAST | Protein HRB1 |
| YMH9_YEAST | Uncharacterized protein YML079W |
| YO389_YEAST | Uncharacterized protein YOR389W |
| HRR25_YEAST | Casein kinase I homolog HRR25 |
| YPT32_YEAST | GTP-binding protein YPT32/YPT11 |
| CCR4_YEAST | Glucose-repressible alcohol dehydrogenase transcriptional effector |
| TSR4_YEAST | 20S rRNA accumulation protein 4 |
| CIS3_YEAST | Cell wall mannoprotein CIS3 |
| PPCS_YEAST | Phosphopantothenate--cysteine ligase CAB2 |
| YD476_YEAST | Uncharacterized protein YDR476C |
| CRP1_YEASB | Cruciform DNA-recognizing protein 1 |
| VHS2_YEAST | Protein VHS2 |
| SVL3_YEAST | Styryl dye vacuolar localization protein 3 |
| FET3_YEAST | Iron transport multicopper oxidase FET3 |
| NOG1_YEAST | Nucleolar GTP-binding protein 1 |
| EAP1_YEAST | Protein EAP1 |
| UTP25_YEAS1 | U3 small nucleolar RNA-associated protein 25 |
| GPN1_YEAST | GPN-loop GTPase 1 |
| OPLA_YEAST | 5-oxoprolinase |
| FCY1_YEAST | Cytosine deaminase |
| AP1M1_YEAST | AP-1 complex subunit mu-1-I |
| RM35_YEAST | 54S ribosomal protein L35, mitochondrial |
| OXA1_YEAST | Mitochondrial inner membrane protein OXA1 |
| YBU6_YEAST | Uncharacterized protein YBR096W |

It can be seen from Table 7 that 45 proteins which were uniquely expressed in the treated versus control samples for the pellet samples immediately after treatment (t0); and that 57 proteins were uniquely expressed in the treated versus control samples for the pellet samples at 3 hours following treatment (t3.0 h).

It can be further seen from Table 7 that the proteins uniquely identified in the pellet samples of yeast cells exposed to pulsed modified plasma output for about 4.9 min are distinct from the proteins identified in the pellet samples of yeast following treatment by pulsed modified plasma output for about 2.8 min. This shows that the pulse number and duration of the modified plasma output discharge have an effect on protein expression profile in yeast.

According to some embodiments, the pulse duration and pattern of the modified plasma output affects the set of proteins which can be induced or enhanced or upregulated in yeast cells.

In other words, by amending the modified plasma output pulse duration and profile, modulation of the yeast proteome expressed pattern can be achieved.

It can be further seen in Table 7 that the proteins expressed immediately after treatment are different from the expressed proteins identified 3 h following treatment.

Panther software was used to identify and describe protein class and protein pathways in the treated and control yeasts cells.

Reference is now made to FIGS. 6 and 7 showing protein class and protein pathway analysis identified by the Panther software, respectively FIG. 6 (panel A) shows that the proteins identified by the Panther software in treatment samples belong to 19 families. The most abundant protein groups, regarding the protein abundancy are:

Nucleic acid binding (23.6%), Oxidoreductase (13.9%), Hydrolase (11%), Transferase (8.3%) and Transcription factor (6.9%).

Additionally, FIG. 6 shows that the proteins identified by the Panther software in control samples belong to 16 families. The most abundant protein groups, regarding the protein abundancy are:

Transferase (16.2%), Nucleic acid binding (13.5%), Hydrolase (12.2%), Oxidoreductase (12.2%) and Transporter (9.5%)

The results of FIG. 6 show that the percentage of proteins which belong to nucleic acid binding family identified in the treated samples, was substantially larger (more than 1.7 fold) than the same family identified in the control samples; while the percentage of proteins which belong to transferase family identified in the treated samples, was lower than the same family identified in the control samples. However, the percentage of proteins which belong to oxidoreductase family identified in the treated samples (13.9%), was similar to the same family identified in the control samples (16.2%)

In addition to the different abundancy of proteins identified in treated versus control samples, and to the type of protein groups, FIG. 5 shows also differences which are related to the type of protein in each protein group. For example, the proteins which comprise the nucleic acid binding groups identified in the treatment samples are either RNA binding proteins (61.5%), DNA binding proteins (23.1%) or nuclease (15.4%); while the proteins which comprise the nucleic acid binding groups identified in the control samples are only RNA binding proteins (100%). Additional example: the proteins which comprise the transferase group identified in the treatment samples are either acetyltransferase, acyltransferase, kinase, methyltransferase and transaminase; while the proteins which comprise the transferase group identified in the control are either kinases, methyltransferase and nudeotidyltransferase.

II. Type of Proteins Pathways in Treated and Non-Treated Cells

Reference is now made to FIG. 7 presenting protein pathways in the treated (panel A) and control (panel B) yeasts cells.

FIG. 7 shows a large difference in protein pathways analyzed in the treated compared to control yeasts cells. Comparing protein pathways in the treated compared to control yeasts cells showed that out of 18 identified protein pathways there were only four similar pathways. The main pathways in the treated yeast cells are Ubiquitin proteasome pathway (15.6%) and Parkinson disease (10.5%); while in control yeast cells the main pathways are: transcription regulation by b/zip transcription factor (9.5%) General transcription regulation (9.5%) and proline biosynthesis (9.5%). The treatment cells analysis revealed 6 pathways related to signaling (apoptosis signaling; CCKR signaling map; EFG receptor signaling; Hegehog signaling; Toll receptor signaling; wnt signaling); while the control cells revealed only 2 signaling pathways (PDGF signaling and Inflammation mediated by chemokinase and cytokine signaling pathway). Furthermore, the treatment cells analysis revealed only 2 pathways related to biosynthesis.
(ATP biosynthesis and Coenzyme A biosynthesis); while the control cells revealed 6 biosynthesis pathways (proline. Cholesterol, Heme, Histidine, Coenzyme A and Pantothenate).

In general, the comparion of the pathways identified in study 1 to pathways identified in study 2 indicates that alteration in number of pulse cycles and in testing time points reveled a large difference of the characterization of protein pathways of treated cells; only four out of all identified pathways are similar, while number and type of proteins in these pathways are not identical.

III. Type of Protein Profiles in Treated and Non-Treated Cell

The protein profiles in control and treated cells were compared by several methodologies. Specifically, all protein spots detected on Two dimensional-differential in gel electrophoresis (2D-DIGE) gel images and cut for MS-Analysis have been analyzed by Principle Component Analysis (PCA) All replicates have been analyzed independently.

To examine to comprehensively characterize the effect of the treatment on yeast cells MALDI-TOF (matrix-assisted laser desorption/ionization (MALDI) and LC-ESI-mass spectrometry was used to perform protein-identifications in 235 spots. In addition, 102 protein spots out of those 235 spots have been analysed also by LC-ESI-MS/MS and resulted in 550 protein identifications.

2D DIGE—Two-Dimensional (2D) Gel Electrophoresis

2D DIGE provides a proteome mapping of the sample via orthogonal mass/charge analysis. The method is based on the combination of two single-dimension electrophoretic runs: the first run, via a pH gradient, separates the proteins according to their isoelectric point (pI), whereas the second run separates them according to their molecular mass. The result is a two-dimensional map where the proteins appear as spots spread all over the gel surface. Once the maps, obtained from protein migration, have been acquired as images, the biological information embedded in the 2D maps is processed and quantified to perform a differential analysis between the single protein spots of different samples—in this case treated versus control samples at the different times points and also between two time points within both treated and control samples.

2D-DIGE Image Analysis

All gel-images were loaded und analysed with Delta2D software package (Decodon, Germany). Gels of the same condition (for example treated versus control samples in a defined time point) have been matched and fused into one fusion-gel which was used to calculate dual channel overlay images. Spots of interest (up- or down-regulated) identified by red or green colour, respectively. Spots without any changes appeared in yellow colour on the dual channel overlay and have been not selected for protein identification experiments.

Qualitative image analyses of dual channel comparison already showed multiple treatment-related changes of intensities of protein spots. However, although 2-DE-based proteomic approaches can precisely identify treatment-related alterations in the intensity of protein spots, they need complementary mass spectrometry approaches to reveal protein identities.

Principle Component Analysis PCA Methodology:

PCA uncovers significant treatment effects. It reduces dimensionality of data and may visualize the correlations and separations of data subsets (sets of sample replicates or sets of proteins with similar expression). Each sample is described by a multi-dimensional vector, defined by the all expression values for every detected protein spot. After dimensionality reduction in a 2D chart, principal components describe the highest variances of the data cloud from n-dimensional space. Similar samples, such as technical replicates appear in close sets of data points with equal colour. Different samples appear spatially more distant. The appropriate three-dimensional PCA plot and an optimal 2D projection of two of the first three principal components are displayed.

Compared to peptide-based LC-MS proteomic approaches, 2-D gel electrophoresis offers the ability to monitor protein modifications that alter protein mobility (processing, degradation, post translation modifications at individual positions), because separation occurs at the protein level. Protein modifications due to the treatment in our study appear as changes in intensity in multiple spots with the same protein identification by MALDI-TOF-MS.

Figure 8A:
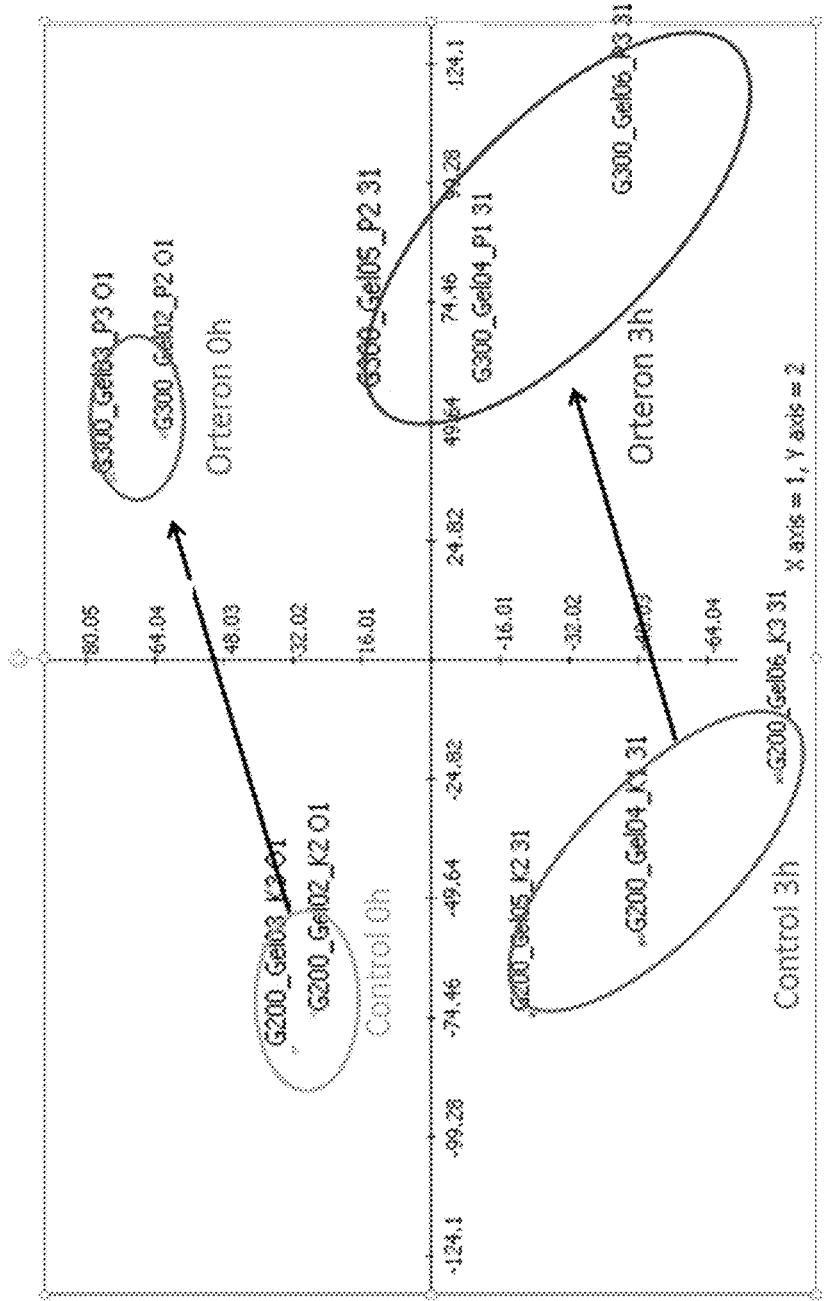
FIGS. 8A-8C are diagrams presenting comparison of protein profiles in control and treated cells performed by PCA.
Figure 8B:
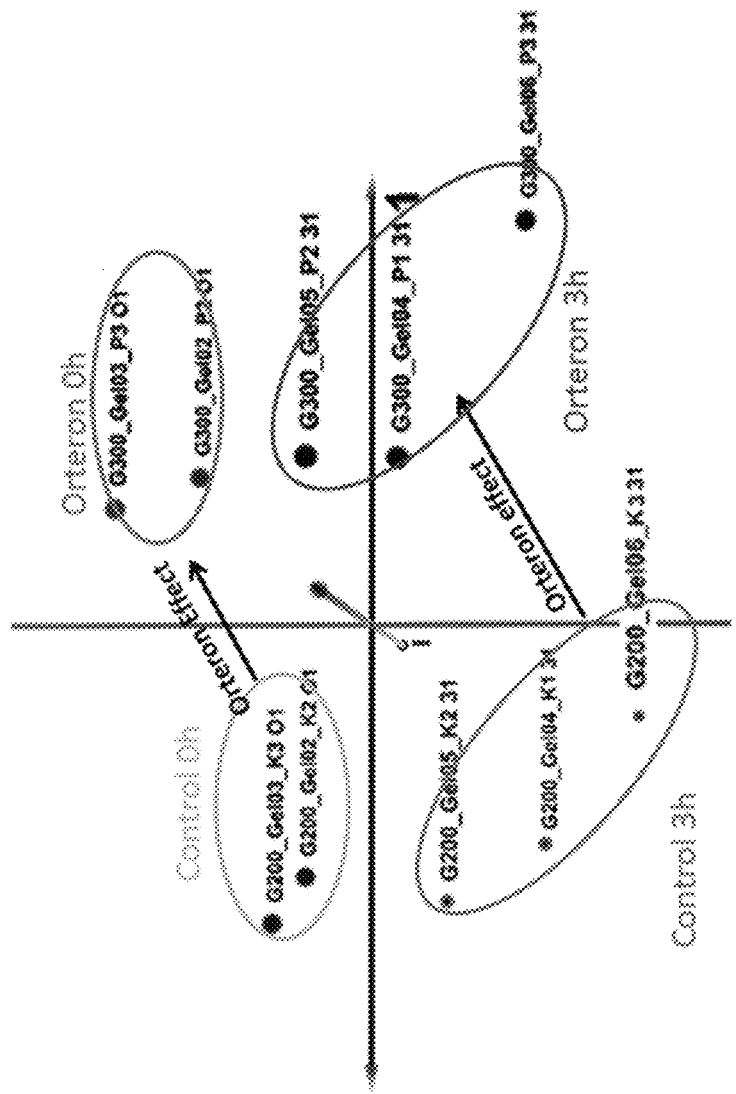
Figure 8C:
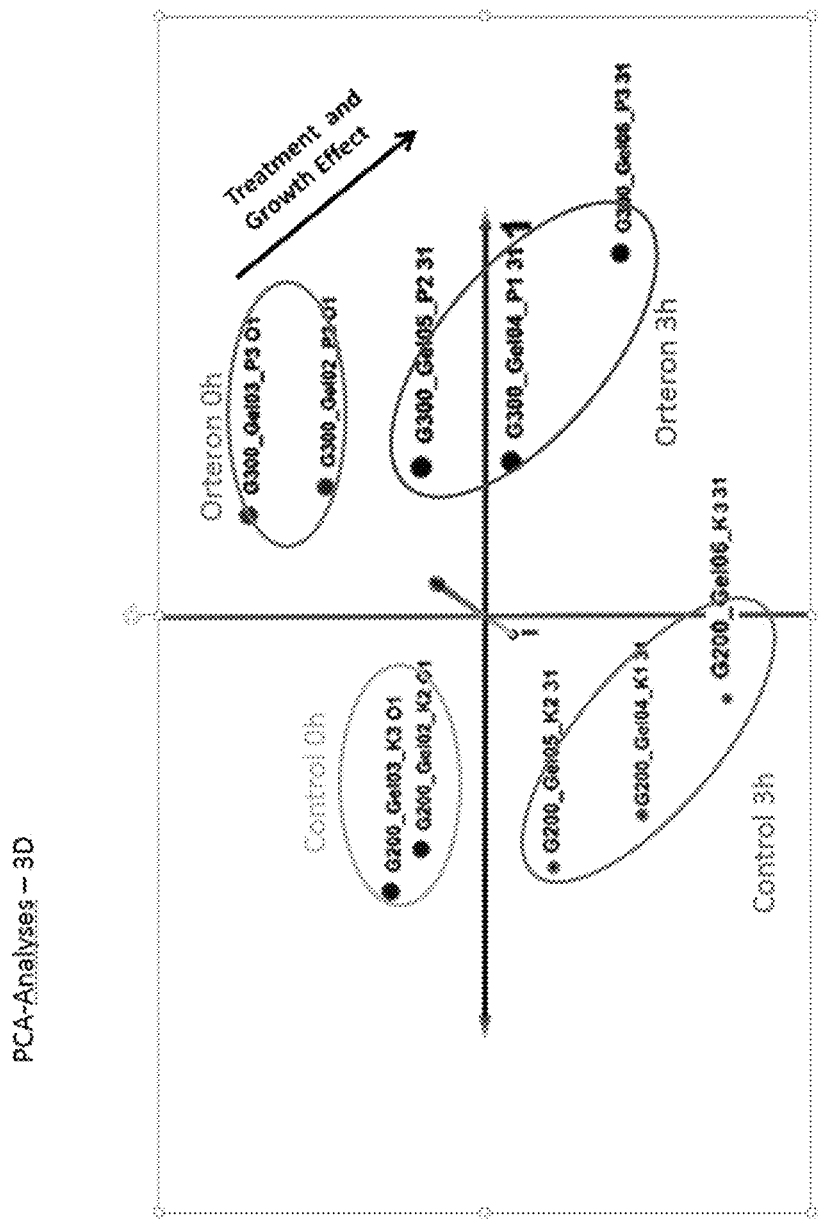

Reference is now made to FIG. 8A, 8B, 8C showing comparison of protein profiles in control and treated cells performed by PCA. PCA demonstrated both: appearance of the treatment-related and cell culture effects.

FIG. 8A present PCA analysis performed in 2D, while FIG. 8B, 8C present PCA performed in 3D.

The three shown principal components presented in FIG. 8 explain 37.8% (PC1), 23.6% (PC2) and 16.8% (PC3), sum for first two components=61.3% sum for all three components=78.2%, of data variance.

Reference is now made to Table 8, presenting several examples for the final MALDI analysis and changes along the two dimensions.

Using a MALDI-TOF/TOF-MS approach, 60 proteins spots have been successfully identified with 87 protein identifications. Many proteins were represented by more than one protein spot and therefore the proteome analysis covered proteins coded by more than 250 different genes.

TABLE 8

Protein analysis results by MALDI

| Accession Number | Protein Name | Protein MW | Peptide Count | Protein Score | Protein Score C.I. % | Total Ion Score | Ion score % |
|---|---|---|---|---|---|---|---|
| EF2_YEAST | Elongation factor 2 | 93230.227 | 16 | 135.0 | 100.0 | 58.2 | 99.8 |
| | Elongation factor 2 | 93230.227 | 18 | 445.0 | 100.0 | 346.0 | 100.0 |
| | Elongation factor 2 | 93230.227 | 14 | 260.0 | 100.0 | 195.3 | 100.0 |
| | Elongation factor 2 | 93230.227 | 16 | 186.0 | 100.0 | 106.1 | 100.0 |
| HSC82_YEAST | ATP-dependent molecular chaperone HSC82 | 0849.656 | 23 | 216.0 | 100.0 | 65.1 | 100.0 |
| HSP82_YEAST | ATP-dependent molecular chaperone HSP82 | 81356 | 18 | 161.0 | 100.0 | 65.1 | 100.0 |
| PDC1_YEAST | Pyruvate decarboxylase isozyme 1 | 61456.641 | 10 | 80.6 | 99.5 | 33.6 | 59.2 |
| PDC1_YEAST | Pyruvate decarboxylase isozyme 1 | 61456.641 | 16 | 307.0 | 100.0 | 204.7 | 100.0 |

Figure 9:
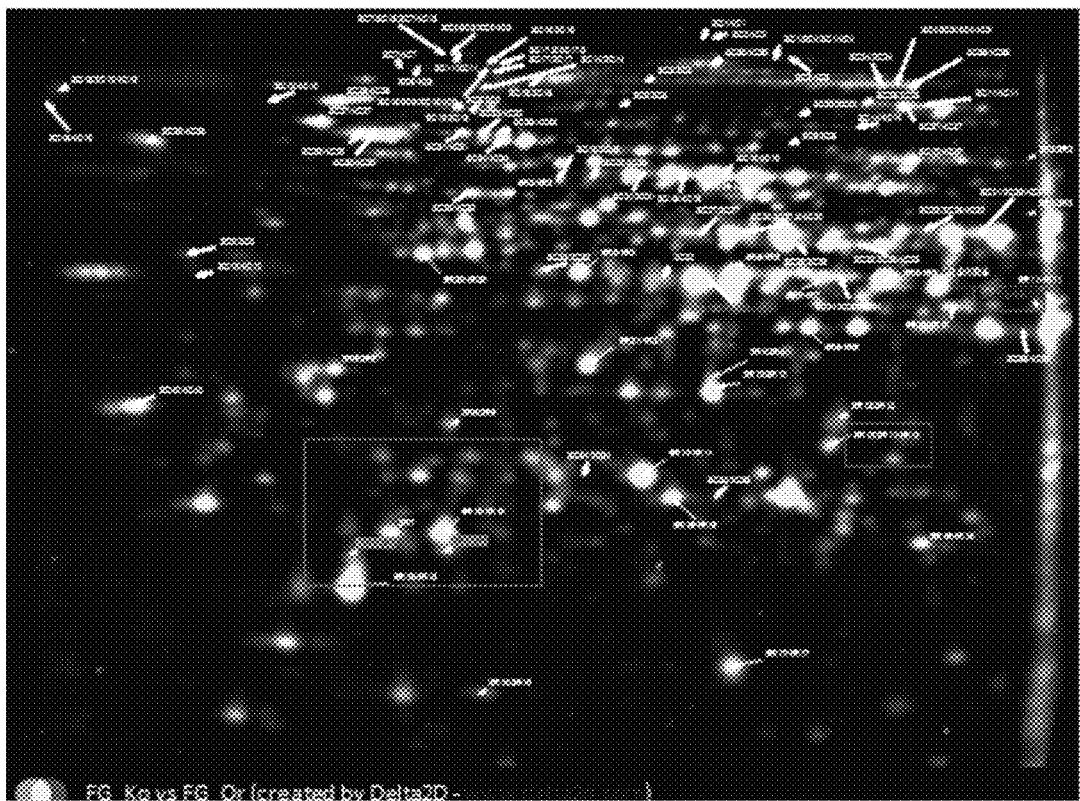
FIG. 9 photographically presents two-dimensional gel electrophoresis of proteins of treatment and control groups.

Reference in now made to FIG. 9, presenting two-dimensional gel electrophoresis of proteins of treatment and control groups, beyond time of measurement. The analysis is based on both: MALDI results and CS identification and 2D DIGE and ratios.

Reference is now made to Table 9.

FIG. 9 and Table 9 show the modifications triggered by the treatment resulting in changes of spot patterns of the same identified protein.

TABLE 9

Protein analysis results by MALDI, CS indentification and 2D DIGE and ratios.

| 3R8 | TSA1_YEAST, EF3A_YEAST, ENO2_YEAST, APT1_YEAST, YKT6_YEAST, ENO1_YEAST, PSB1_YEAST, CY1_YEAST, GRPE_YEAST | 2R8 | 1 | TSA1_YEAST | Peroxiredoxin TSA1 OS = *Saccharomyces cerevisiae* (strain ATCC 204508/S288c) GN = TSA1 PE = 1 SV = 3 | 21576.25 | 5 | 106.0 | 100.0 | 57.7 | 99.9 |
|---|---|---|---|---|---|---|---|---|---|---|---|
| 5R7 | ADH1_YEAST, OYE2_YEAST, MVD1_YEAST, IDHC_YEAST, KPYK1_YEAST, ENO1_YEAST, FHP_YEAST, ALF_YEAST, PDC1_YEAST, GLNA_YEAST, ACT_YEAST | 4R7 | 1 | ADH1_YEAST | Alcohol dehydrogenase 1 OS = *Saccharomyces cerevisiae* (strain ATCC 204508/S288c) GN = ADH1 PE = 1 SV = 5 | 36825.671 | 9 | 302.0 | 100.0 | 244.4 | 100.0 |
| 5R12 | ILV5_YEAST, PDC1_YEAST | 4R12 | 1 | ADH1_YEAST | Alcohol dehydrogenase 1 OS = *Saccharomyces cerevisiae* (strain ATCC 204508/S288c) GN = ADH1 PE = 1 SV = 5 | 36825.67188 | 13 | 295.0 | 100.0 | 196.1 | 100.0 |
| 5R13 | PRTB_YEAST, ILV5_YEAST, GPP2_YEAST, QCR2_YEAST, RS6A_YEAST, G3P3_YEAST | | | | PRTB_YEAST, ILV5_YEAST, GPP2_YEAST, QCR2_YEAST, RS6A_YEAST, G3P3_YEAST to | | | | | | |
| | PRTB_YEAST, ILV5_YEAST, GPP2_YEAST, QCR2_YEAST, RS6A_YEAST, G3P3_YEAST | 4R13 | 1 | IF4A_YEAST | ATP-dependent RNA helicase eIF4A OS = *Saccharomyces cerevisiae* (strain ATCC 204508/S288c) GN = TIF1 PE = 1 SV = 3 | 44668.98 | 12 | 261.0 | 100.0 | 182.5 | 100.0 |

Regarding the supernatant samples—The analysis was performed only on the over-representation or under-representation of the proteins, and not the overall number of unique proteins expressed by the treatment only.

Reference is now made to Table 10A, presenting identification of over-regulated intracellular proteins, based on standardized ratio—CS identification 2D—DIGE ratio.

TABLE 10A

List of over-regulated intracellular proteins

Over regulated proteins immediately after treatment and 3 hours after treatment compared to control.
P38011 GBLP Guanine nucleotide-binding protein subunit beta-like protein
P00817 IPYR Inorganic pyrophosphatase
P00549 KPYK1 Pyruvate kinase 1

TABLE 10A-continued

List of over-regulated intracellular proteins

P00560 PGK Phosphoglycerate kinase
P00359 G3P3 Glyceraldehyde-3-phosphate dehydrogenase 3
P53549 PRS10 26S protease subunit RPT4
P53327 SLH1 Antiviral helicase SLH1
P38013 AHP1 Peroxiredoxin type-2
P00925 ENO2 Enolase 2
P34760 TSA1 Peroxiredoxin TSA1
P00924 ENO1 Enolase 1
P10591 HSP71 Heat shock protein SSA1
P11484 HSP75 (SSB1) Ribosome-associated molecular chaperone SSB1
P23301 IF5A1 Eukaryotic translation initiation factor 5A-1
P40069 IMB4 Importin subunit beta-4
P38999 LYS9 Saccharopine dehydrogenase [NADP(+), L-glutamate-forming]
P40096 NCB1 Negative cofactor 2 complex subunit alpha
P07560 SEC4 Ras-related protein SEC4
Over regulated proteins after 3 hours treatment plus self-growing (t(3.0 h) compared to t0)
P26637 SYLC Leucine--tRNA ligase, cytoplasmic
P16521 EF3A Elongation factor 3A
P00925 ENO2 Enolase 2
P14540 ALF Fructose-bisphosphate aldolase
P00924 ENO1 Enolase 1
P34215 YBZ4 Putative uncharacterized protein YBR144C
P05694 METE 5-methyltetrahydropteroyltriglutamate--homocysteine methyltransferase
Over regulated proteins after 3 hours after treatment compared to control 3 hours after treatment
P34760TSA1 Peroxiredoxin TSA1
P16521 EF3A Elongation factor 3A
P00925 ENO2 Enolase 2
P49435 APT1 (3R8) Adenine phosphoribosyltransferase 1
P36047 YKT6 Synaptobrevin homolog YKT6
P00924 ENO1 Enolase 1
P38624 PSB1 Proteasome subunit beta type-1
P07143 CY1 Cytochrome c1, heme protein, mitochondrial
P38523 GRPE GrpE protein homolog, mitochondrial Reference is now made to Table 10B, presenting identification of over-regulated extracellular proteins, based on standardized rations—CS identification 2D—DIGE ratio.

TABLE 10B

List of over-regulated extracellular proteins

Over regulated proteins immediately after treatment and 3 hours after treatment compared to control.
P11484 HSP75 Ribosome-associated molecular chaperone SSB1
P22768 ASSY Argininosuccinate synthase
P38886 RPN10 26S proteasome regulatory subunit RPN10
P14832 CYPH Peptidyl-prolyl cis-trans isomerase
Over regulated proteins after 3 hours treatment (t(3.0 h) compared to control
P05743 RL26A 60S ribosomal protein L26-A
P19414 ACON Aconitase hydratase, mitochondrial
Q3E841 YNO34 Uncharacterized protein YNR034W-A
P38061 RL32 60S ribosomal protein L32
Over regulated proteins immediately after treatment compared to control
P00358 G3P2 Glyceraldehyde-3-phosphate dehydrogenase 2
P09457 ATPO ATP synthase subunit 5, mitochondrial
P16474 GRP78 78 kDa glucose-regulated protein homolog IV. Protein Concentration Measurement Immediately after finishing the experiment the samples (pellet/supernatant) were split into two identical subsamples. The two pellet samples were then worked up differently:

1. immediate addition of lysis buffer (Ripa) and mechanical disruption of the cells (FastPrep), followed by freezing (red labels); or 2. immediate freezing of the cells after adding lysis buffer (Ripa), thawing them again mechanical disruption (FastPrep) and refreezing the samples (blue labels)

The supernatant, after being split, did not receive any additional workup and was just labeled and frozen immediately.

Reference is made to Table 11, presenting the labelling of the samples

| a | | b |
|---|---|---|
| Extracellular 0 h | | |
| P1 0 E | 1 | P1 0 E |
| P2 0 E | 2 | P2 0 E |
| P3 0 E | 3 | P3 0 E |
| K1 0 E | 4 | K1 0 E |
| K2 0 E | 5 | K2 0 E |
| K3 0 E | 6 | K3 0 E |
| Extracellular 3 h | | |
| P1 3 E | 7 | P1 3 E |
| P2 3 E | 8 | P2 3 E |
| P3 3 E | 9 | P3 3 E |
| K1 3 E | 10 | K1 3 E |
| K2 3 E | 11 | K2 3 E |
| K3 3 E | 12 | K3 3 E |

| c | | d |
|---|---|---|
| Intracellular 0 h | | |
| P1 0 I | 13 | P1 0 I |
| P2 0 I | 14 | P2 0 I |
| P3 0 I | 15 | P3 0 I |
| K1 0 I | 16 | K1 0 I |
| K2 0 I | 17 | K2 0 I |
| K3 0 I | 18 | K3 0 I |
| Intracellular 3 h | | |
| P1 3 I | 19 | P1 3 I |
| P2 3 I | 20 | P2 3 I |
| P3 3 I | 21 | P3 3 I |
| K1 3 I | 22 | K1 3 I |
| K2 3 I | 23 | K2 3 I |
| K3 3 I | 24 | K3 3 I |

Protein concentration were measured by Bradford Assay, but no absorption was observed because of sample dilution in RIPA buffer.

New protein assay was used (RCDC Assay on TECAN microtiter plate reader). Protein concentration were determined and calculated for all samples: for intracellular proteins protein concentration was high enough, for extracellular proteins protein concentration was too low for 2D-DIGE labeling procedure.

All protein samples were combined for the following experiments. Final concentrations documented in the following table.

TABLE 12

Summary of protein concentrations and total protein amounts of the treated yeast samples (intra cellular)

| Sample number | Sample | Protein-c [µg/µl] | Total protein amount [µl], ca. 100 µl 1xUT (2D-Lysis buffer) |
|---|---|---|---|
| 13c | P1 0 I | 0.47 | 47.3 |
| 14c | P2 0 I | 1.61 | 161.4 |
| 15c | P3 0 I | 1.93 | 193.4 |
| 16c | K1 0 I | 0.72 | 71.9 |
| 17c | K2 0 I | 2.11 | 210.9 |
| 18c | K3 0 I | 1.80 | 180.2 |
| 19c | P1 3 I | 2.15 | 214.7 |
| 20c | P2 3 I | 1.89 | 189.1 |
| 21c | P3 3 I | 1.88 | 188.4 |

TABLE 12-continued

Summary of protein concentrations and total protein amounts of the treated yeast samples (intra cellular)

| Sample number | Sample | Protein-c [µg/µl] | Total protein amount [µl], ca. 100 µl 1xUT (2D-Lysis buffer) |
|---|---|---|---|
| 22c | K1 3 I | 2.59 | 258.6 |
| 23c | K2 3 I | 2.32 | 232 |
| 24c | K3 3 I | 1.84 | 184.2 |
| 13d | P1 0 I | 0.32 | 32 |
| 14d | P2 0 I | 1.97 | 197.3 |
| 15d | P3 0 I | 1.71 | 171.4 |
| 16d | K1 0 I | 0.46 | 45.6 |
| 17d | K2 0 I | 1.76 | 176.3 |
| 18d | K3 0 I | 1.62 | 162.2 |
| 19d | P1 3 I | 1.92 | 192 |
| 20d | P2 3 I | 2.16 | 216.2 |
| 21d | P3 3 I | 1.99 | 198.6 |
| 22d | K1 3 I | 1.96 | 196.4 |
| 23d | K2 3 I | 2.06 | 205.9 |
| 24d | K3 3 I | 2.43 | 243.2 | c—Lysis in RIPA/FastPrep buffer immediately after sampling d—shock frozen in RIPA buffer, thawed, lysis with FastPrep, immediately frozen Samples 13c and 13d contained a very low protein concentration because of the original samples were very high diluted in a large sample volume. Both samples combined in one sample prior following experiments.

Sample concentrations of all extracellular samples were to low for 2-DIGE experiments—only nanoLC-ESI-MS/MS experiments were planned

2D-DIGE

All sample concentrations of intracellular proteins were high enough for 2D-DIGE experiments and nanoLC-ESI-MS/MS experiments. 45 µg of each paired samples (c and d) were combined into one sample (90 µg) for all following experiments

TABLE 13

2D-DIGE-Setup for intracellular proteins:

| Setup-DIGE | G200 | G300 |
|---|---|---|
| Gel01 | K1 0 I | P1 0 I |
| Gel02 | K2 0 I | P2 0 I |
| Gel03 | K3 0 I | P3 0 I |
| Gel04 | K1 3 I | P1 3 I |
| Gel05 | K2 3 I | P2 3 I |
| Gel06 | K3 3 I | P3 3 I |

NanoLC-ESI-MS/MS

3 µg of each combined intracellular sample was used for nanoLC-ESI-MS/MS approach.

For extracellular samples, 1.5 µg of each paired samples (a and b) were combined into one sample (3 µg) for nanoLC-ESI-MS/MS approach Example 2

Effect of the System and Method of the Present Invention on Protein Expression in *E. coli*

This study was performed to assess the effect of treatment in a system comprising a deep solution (BEAKER) compared to a shallow solution (Petri Dish).

*E. coli* BL21A cells were cultivated in 500 ml shaking flasks with a volume of 100 ml for 24 h. The cultures reached the stationary growth phase. Cultures were centrifuged, and sedimented cells were re-suspended in fresh LB medium. The titres of these starting suspensions were calculated by cfu counts from corresponding dilutions (=vor Beh.).

Petridishes and beakers were sealed with PARAFILM during the incubation at 370 C to exclude evaporation during incubation.

The conditions for the treatement were as follows:

Petridishes (PD)—

6 ml, height of layer 0.305 cm; 6 pulses which were 4.2 minutes of treatment session application; while the distance between the modifying plasma mechanism and the treated sample was 3 cm.

Beaker (BEAKER)—

12 ml, height of layer 0.61 cm; 14 pulses, which were 9.8 minutes of treatment session application; while the distance between the modifying plasma mechanism and the treated sample was 7 cm.

Tie points for testing are immediately following treatment (t0), at 3 hours following treatment (t3.0 h) and at 6 hours following treatment (t6.0 h).

Type of Proteins in Treated and Non-Treated Cells

Reference is now made to Table 14 presenting a list of proteins unique to the treated samples (not identified in the BEAKER samples. The list includes treated-cells unique BEAKER proteins identified immediately after treatment (t0), 1 hour (t1.0 h) and 6 hours following treatment (t6.0 h).

TABLE 14A

BEAKER proteins identified in the treated samples and not in the control samples at (t0), N = 84

| | |
|---|---|
| HPF_ECOLI | Ribosome hibernation promoting factor |
| UBIE_ECOLI | Ubiquinone/menaquinone biosynthesis C-methyltransferase UbiE |
| PYRI_ECOLI | Aspartate carbamoyltransferase regulatory chain |
| NDK_ECOLI | Nucleoside diphosphate kinase |
| GUAC_ECOLI | GMP reductase |
| RLMN_ECOLI | Dual-specificity RNA methyltransferase RlmN |
| YIHI_ECOLI | Der GTPase-activating protein YihI |
| PROB_ECOLI | Glutamate 5-kinase |
| YIAD_ECOLI | Probable lipoprotein YiaD |
| AK2H_ECOLI | Bifunctional aspartokinase/homoserine dehydrogenase 2 |
| TATA_ECOLI | Sec-independent protein translocase protein TatA |
| RMLB1_ECOLI | dTDP-glucose 4,6-dehydratase 1 |
| TRPB_ECOLI | Tryptophan synthase beta chain |
| GLTD_ECOLI | Glutamate synthase [NADPH] small chain |
| ALAC_ECOLI | Glutamate-pyruvate aminotransferase AlaC |
| GALF_ECOLI | UTP--glucose-1-phosphate uridylyltransferase |
| YBBN_ECOLI | Uncharacterized protein YbbN |
| MIAA_ECOLI | tRNA dimethylallyltransferase |
| BAER_ECOLI | Transcriptional regulatory protein BaeR |
| MASZ_ECOLI | Malate synthase G |
| FTSN_ECOLI | Cell division protein FtsN |
| ALAA_ECOLI | Glutamate-pyruvate aminotransferase AlaA |
| THIL_ECOLI | Thiamine-monophosphate kinase |
| DXR_ECOLI | 1-deoxy-D-xylulose 5-phosphate reductoisomerase |
| YFBT_ECOLI | Hexitol phosphatase A |
| MDTE_ECOLI | Multidrug resistance protein MdtE |
| SUFC_ECOLI | Probable ATP-dependent transporter SufC |
| CYSD_ECOLI | Sulfate adenylyltransferase subunit 2 |
| OXYR_ECOLI | Hydrogen peroxide-inducible genes activator |
| YCCU_ECOLI | Uncharacterized protein YccU |
| GLRX1_ECOLI | Glutaredoxin 1 |
| YGGS_ECOLI | Pyridoxal phosphate homeostasis protein |
| CSDA_ECOLI | Cysteine desulfurase CsdA |
| YCEI_ECOLI | Protein YceI |
| RODZ_ECOLI | Cytoskeleton protein RodZ |
| GCH1L_ECOLI | GTP cyclohydrolase 1 type 2 homolog |
| MURI_ECOLI | Glutamate racemase |
| RSGA_ECOLI | Small ribosomal subunit biogenesis GTPase RsgA |
| SERB_ECOLI | Phosphoserine phosphatase |

TABLE 14A-continued

BEAKER proteins identified in the treated samples and not in the control samples at (t0), N = 84

| | |
|---|---|
| RLMB_ECOLI | 23S rRNA (guanosine-2'-O-)-methyltransferase RlmB |
| YFCL_ECOLI | Uncharacterized protein YfcL |
| RCSF_ECOLI | Outer membrane lipoprotein RcsF |
| DLHH_ECOLI | Putative carboxymethylenebutenolidase |
| YGJR_ECOLI | Uncharacterized oxidoreductase YgjR |
| RNPH_ECOLI | Inactive ribonuclease PH |
| RNG_ECOLI | Ribonuclease G |
| TATB_ECOLI | Sec-independent protein translocase protein TatB |
| YEBE_ECOLI | Inner membrane protein YebE |
| LEP_ECOLI | Signal peptidase I |
| GLPA_ECOLI | Anaerobic glycerol-3-phosphate dehydrogenase subunit A |
| YEBV_ECOLI | Uncharacterized protein YebV |
| AROC_ECOLI | Chorismate synthase |
| RLMM_ECOLI | Ribosomal RNA large subunit methyltransferase M |
| RATB_ECOLI | UPF0125 protein RatB |
| UBII_ECOLI | 2-octaprenylphenol hydroxylase |
| SPOT_ECOLI | Bifunctional (p)ppGpp synthase/hydrolase SpoT |
| MUKE_ECOLI | Chromosome partition protein MukE |
| OSME_ECOLI | Osmotically-inducible putative lipoprotein OsmE |
| LDCI_ECOLI | Inducible lysine decarboxylase |
| PFLA_ECOLI | Pyruvate formate-lyase 1-activating enzyme |
| MTOX_ECOLI | N-methyl-L-tryptophan oxidase |
| AROG_ECOLI | Phospho-2-dehydro-3-deoxyheptonate aldolase, Phe-sensitive |
| YHHA_ECOLI | Uncharacterized protein YhhA |
| LPTB_ECOLI | Lipopolysaccharide export system ATP-binding protein LptB |
| FRDB_ECOLI | Fumarate reductase iron-sulfur subunit |
| DSBA_ECOLI | Thiol: disulfide interchange protein DsbA |
| MDAB_ECOLI | Modulator of drug activity B |
| TSX_ECOLI | Nucleoside-specific channel-forming protein tsx |
| CSDE_ECOLI | Sulfur acceptor protein CsdE |
| RSUA_ECOLI | Ribosomal small subunit pseudouridine synthase A |
| INGK_ECOLI | Inosine-guanosine kinase |
| DNLJ_ECOLI | DNA ligase |
| NADC_ECOLI | Nicotinate-nucleotide pyrophosphorylase [carboxylating] |
| FKBX_ECOLI | FKBP-type 16 kDa peptidyl-prolyl cis-trans isomerase |
| MAK_ECOLI | .Fructokinase |
| DYR_ECOLI | Dihydrofolate reductase |
| MLAF_ECOLI | Probable phospholipid import ATP-binding protein MlaF |
| MUKB_ECOLI | Chromosome partition protein MukB |
| POTD_ECOLI | Spermidine/putrescine-binding periplasmic protein |
| MLAC_ECOLI | Probable phospholipid-binding protein MlaC |
| MGLA_ECOLI | Galactose/methyl galactoside import ATP-binding protein MglA |
| OPGD_ECOLI | Glucans biosynthesis protein D |
| QOR1_ECOLI | Quinone oxidoreductase 1 |
| MAO1_ECOLI | NAD-dependent malic enzyme |

TABLE 14B

BEAKER proteins identified in the treated samples and not in the control samples at (t1.0h), N = 42

| | |
|---|---|
| YCCU_ECOLI | Uncharacterized protein YccU |
| GRCA_ECOLI | Autonomous glycyl radical cofactor |
| AROG_ECOLI | Phospho-2-dehydro-3-deoxyheptonate aldolase, Phe-sensitive |
| EFEO_ECOLI | Iron uptake system component EfeO |
| LPXD_ECOLI | UDP-3-O-(3-hydroxymyristoyl)glucosamine N-acyltransferase |
| SOHB_ECOLI | Probable protease SohB |
| NRDD_ECOLI | Anaerobic ribonucleoside-triphosphate reductase |
| HELD_ECOLI | DNA helicase IV |
| OTSA_ECOLI | Trehalose-6-phosphate synthase |
| LEXA_ECOLI | LexA repressor |
| GPPA_ECOLI | Guanosine-5'-triphosphate,3'-diphosphate pyrophosphatase |

TABLE 14B-continued

BEAKER proteins identified in the treated samples and not in the control samples at (t1.0h), N = 42

| | |
|---|---|
| 3PASE_ECOLI | Inorganic triphosphatase |
| RL28_ECOLI | 50S ribosomal protein L28 |
| YBBN_ECOLI | Uncharacterized protein YbbN |
| PREA_ECOLI | NAD-dependent dihydropyrimidine dehydrogenase subunit PreA |
| DXR_ECOLI | 1-deoxy-D-xylulose 5-phosphate reductoisomerase |
| GUDD_ECOLI | Glucarate dehydratase |
| YMDB_ECOLI | O-acetyl-ADP-ribose deacetylase |
| NAGA_ECOLI | N-acetylglucosamine-6-phosphate deacetylase |
| PTH_ECOLI | Peptidyl-tRNA hydrolase |
| YFGD_ECOLI | Uncharacterized protein YfgD |
| CUEO_ECOLI | Blue copper oxidase CueO |
| YNIC_ECOLI | Hexitol phosphatase B |
| RSMA_ECOLI | Ribosomal RNA small subunit methyltransferase A |
| RSGA_ECOLI | Small ribosomal subunit biogenesis GTPase RsgA |
| YEEN_ECOLI | Probable transcriptional regulatory protein YeeN |
| RHLE_ECOLI | ATP-dependent RNA helicase RhlE |
| ANMK_ECOLI | Anhydro-N-acetylmuramic acid kinase |
| YKGF_ECOLI | Uncharacterized electron transport protein YkgF |
| RCSF_ECOLI | Outer membrane lipoprotein RcsF |
| KDSC_ECOLI | 3-deoxy-D-manno-octulosonate 8-phosphate phosphatase KdsC |
| ARTP_ECOLI | Arginine transport ATP-binding protein ArtP |
| ATDA_ECOLI | Spermidine N(1)-acetyltransferase |
| YGHA_ECOLI | Uncharacterized oxidoreductase YghA |
| YFEY_ECOLI | Uncharacterized protein YfeY |
| OSME_ECOLI | Osmotically-inducible putative lipoprotein OsmE |
| PTM3C_ECOLI | PTS system mannitol-specific EIICBA component |
| RF3_ECOLI | Peptide chain release factor RF3 |
| YGGS_ECOLI | Pyridoxal phosphate homeostasis protein |
| BETB_ECOLI | NAD/NADP-dependent betaine aldehyde dehydrogenase |
| RS16_ECOLI | 30S ribosomal protein S16 |
| NRDR_ECOLI | Transcriptional repressor NrdR |

TABLE 14C

BEAKER proteins identified in the treated samples and not in the control samples at (t6.0h), N = 60

| | |
|---|---|
| PHEA_ECOLI | P protein |
| FTSA_ECOLI | Cell division protein FtsA |
| STPA_ECOLI | DNA-binding protein StpA |
| UDG_ECOLI | UDP-glucose 6-dehydrogenase |
| YJBR_ECOLI | Uncharacterized protein YjbR |
| YCIO_ECOLI | Uncharacterized protein YciO |
| GPR_ECOLI | L-glyceraldehyde 3-phosphate reductase |
| RS8_ECOLI | 30S ribosomal protein S8 |
| GLTD_ECOLI | Glutamate synthase [NADPH] small chain |
| ISCU_ECOLI | Iron-sulfur cluster assembly scaffold protein IscU |
| CSDA_ECOLI | Cysteine desulfurase CsdA |
| HIS5_ECOLI | Imidazole glycerol phosphate synthase subunit HisH |
| YBIC_ECOLI | Hydroxycarboxylate dehydrogenase B |
| YCFP_ECOLI | UPF0227 protein YcfP |
| SDHD_ECOLI | D-serine dehydratase |
| OTSA_ECOLI | Trehalose-6-phosphate synthase |
| GPPA_ECOLI | Guanosine-5'-triphosphate,3'-diphosphate pyrophosphatase |
| TSAE_ECOLI | tRNA threonylcarbamoyladenosine biosynthesis protein TsaE |
| YEGQ_ECOLI | Uncharacterized protease YegQ |
| YHGF_ECOLI | Protein YhgF |
| DXR_ECOLI | 1-deoxy-D-xylulose 5-phosphate reductoisomerase |
| FDOH_ECOLI | Formate dehydrogenase-O iron-sulfur subunit |
| GUDD_ECOLI | Glucarate dehydratase |
| YMDB_ECOLI | O-acetyl-ADP-ribose deacetylase |
| MGSA_ECOLI | Methylglyoxal synthase |
| RS16_ECOLI | 30S ribosomal protein S16 |
| SUFC_ECOLI | Probable ATP-dependent transporter SufC |
| OTC1_ECOLI | Ornithine carbamoyltransferase subunit I |
| UBID_ECOLI | 3-octaprenyl-4-hydroxybenzoate carboxy-lyase |
| YNIC_ECOLI | Hexitol phosphatase B |

TABLE 14C-continued

BEAKER proteins identified in the treated
samples and not in the control samples
at (t6.0h), N = 60

| | |
|---|---|
| IAAA_ECOLI | Isoaspartyl peptidase |
| RSGA_ECOLI | Small ribosomal subunit biogenesis GTPase RsgA |
| SUPH_ECOLI | Sugar phosphatase YbiV |
| HEM3_ECOLI | Porphobilinogen deaminase |
| FHUA_ECOLI | Ferrichrome-iron receptor |
| RSMC_ECOLI | Ribosomal RNA small subunit methyltransferase C |
| QUEC_ECOLI | 7-cyano-7-deazaguanine synthase |
| PKA_ECOLI | Protein lysine acetyltransferase Pka |
| YJGR_ECOLI | Uncharacterized protein YjgR |
| TATB_ECOLI | Sec-independent protein translocase protein TatB |
| YEBE_ECOLI | Inner membrane protein YebE |
| RMLB2_ECOLI | dTDP-glucose 4,6-dehydratase 2 |
| MNMC_ECOLI | tRNA 5-methylaminomethyl-2-thiouridine biosynthesis bifunctional protein MnmC |
| TOLQ_ECOLI | Protein TolQ |
| YCED_ECOLI | Large ribosomal RNA subunit accumulation protein YceD |
| KDSC_ECOLI | 3-deoxy-D-manno-octulosonate 8-phosphate phosphatase KdsC |
| ATDA_ECOLI | Spermidine N(1)-acetyltransferase |
| E4PD_ECOLI | D-erythrose-4-phosphate dehydrogenase |
| PRMA_ECOLI | Ribosomal protein L11 methyltransferase |
| PTRA_ECOLI | Protease 3 |
| NUDJ_ECOLI | Phosphatase NudJ |
| CYSD_ECOLI | Sulfate adenylyltransferase subunit 2 |
| UGPB_ECOLI | sn-glycerol-3-phosphate-binding periplasmic protein UgpB |
| GHRA_ECOLI | Glyoxylate/hydroxypyruvate reductase A |
| GNSA_ECOLI | Protein GnsA |
| FTSN_ECOLI | Cell division protein FtsN |
| RLMB_ECOLI | 23S rRNA (guanosine-2'-O-)-methyltransferase RlmB |
| PYRF_ECOLI | Orotidine 5'-phosphate decarboxylase |
| YKGE_ECOLI | Uncharacterized protein YkgE |
| YBBN_ECOLI | Uncharacterized protein YbbN |

Figure 10:
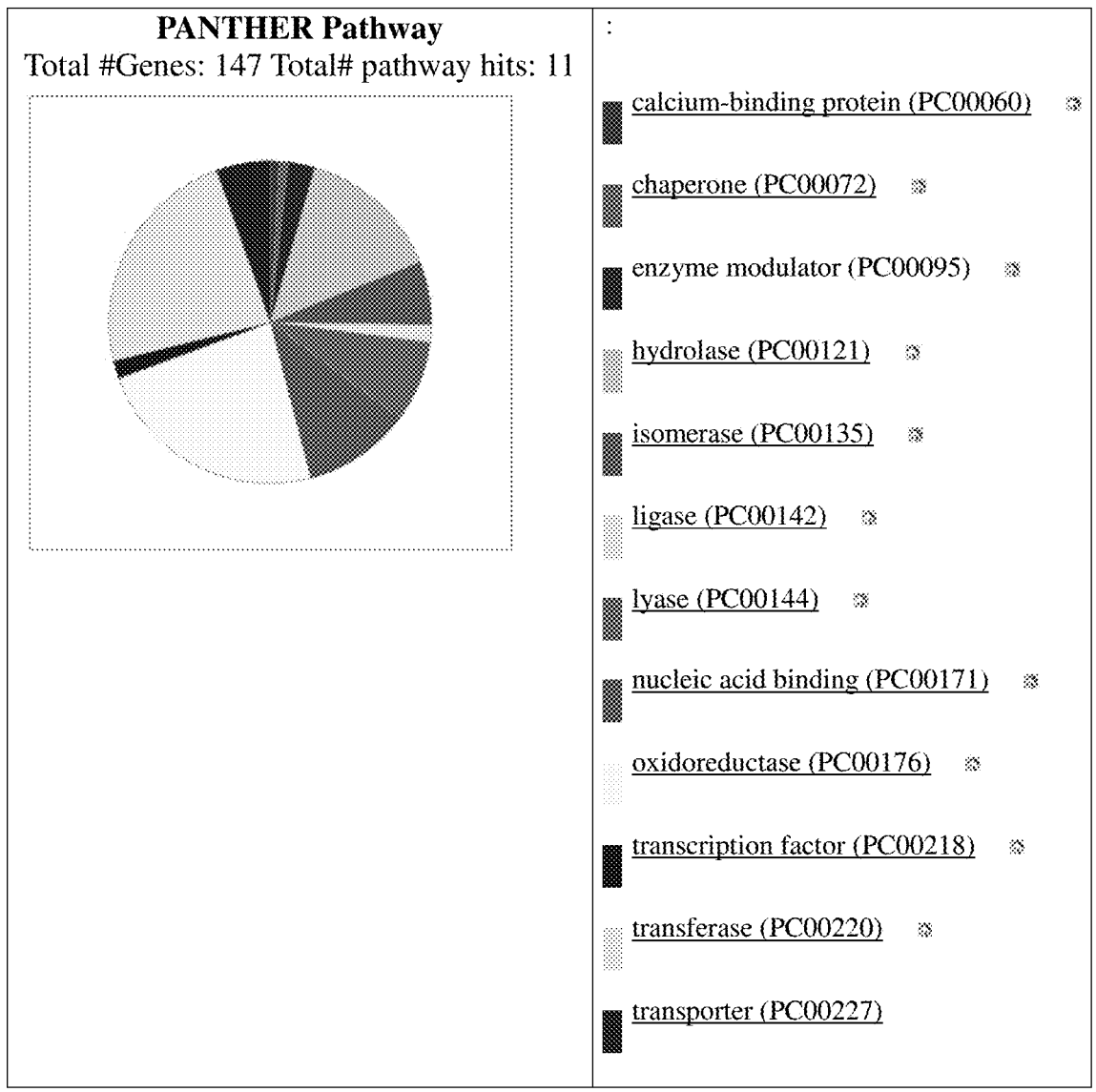
FIG. 10 is a diagram presenting protein class analysis, in *E. coli* treatment samples of deep solution (BEAKER), identified by the Panther software.
Figure 11A:
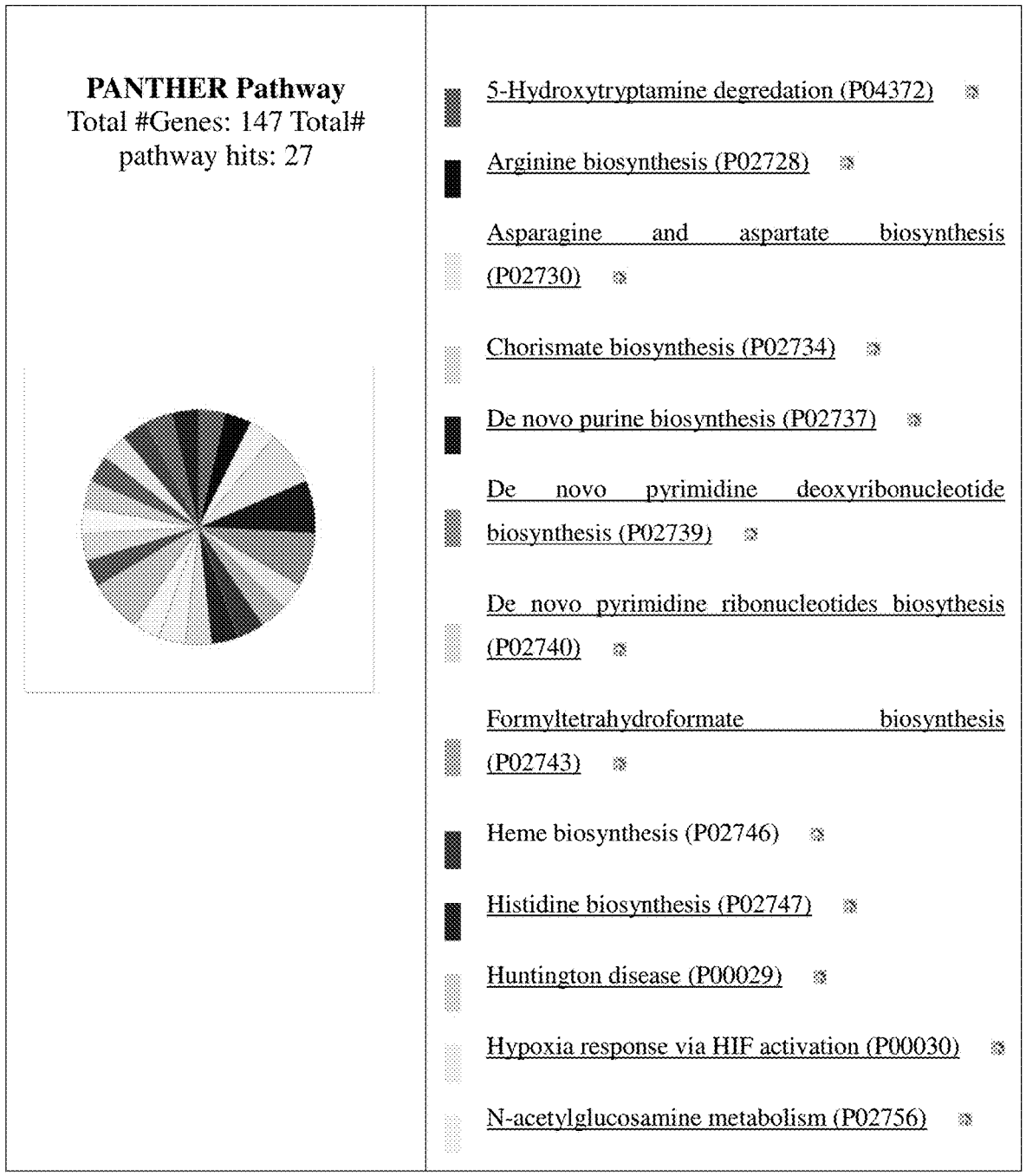

I. Description of Selected Unique Proteins and Pathways Produced Following Treatment Reference is now made to FIG. 10, 11 showing protein class analysis and protein pathways, respectively, in treatment samples of BEAKER, identified by the Panther software.

Figure 12:
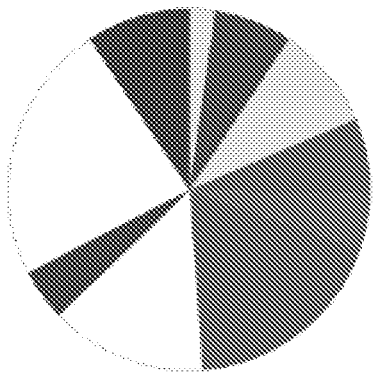
FIG. 12 is a diagram presenting protein class analysis, in *E. coli* control samples of deep solution (BEAKER), identified by the Panther software.

Reference is now made to FIG. 12 and FIG. 13 showing protein class analysis and protein pathways, respectively, in control samples in BEAKER, identified by the Panther software.

The results of FIG. 10-13 show that the proteins identified in the treatment samples, were different than proteins identified in the control samples. For example, the proteins identified by the Panther software in treatment samples belong to 12 families. The most abundant protein groups, regarding the protein abundancy are: oxidoreductase (23.4%), transferase (23.4%), hydrolase (14.4%), and nucleic acid binding (10.8%); while the most abundant protein groups, among the 10 families identified in the control samples are: transferase (23.3%), nucleic acid binding (18.6%), oxidoreductase (14.0%), transporter (9.3%), and cytoskeletal (9.3%).

Additionally, FIGS. 10-13 show difference in protein pathways analyzed in the treated compared to control *E. coli* cells. Comparing protein pathways in the treated to control yeasts cells showed that out of 23 identified protein pathways for the treated sample, 15 were identified as biosynthesis pathways; while in control *E coli* cells the main pathways are also biosynthesis (11 out of 15 pathways); however only 7 pathways are mutual; furthermore the proteins comprising these comment groups are different.

Therefore, in general, the above findings indicate that the treatment affects the profile of protein pathways.

Figure 14:
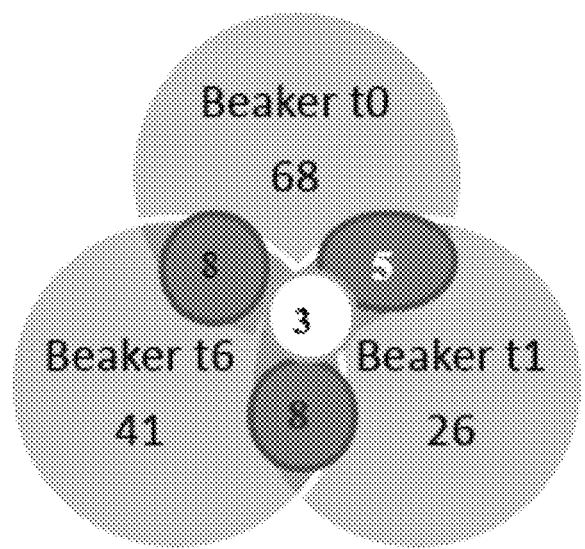
FIG. 14 is a diagram presenting unique *E. coli* proteins identified after treatment in shallow solution (Petri Dish)

Reference is now made to FIG. 14, the number of unique proteins identified after treatment in BEAKER is 135, 68 unique proteins at (t0 h), 26 proteins at (t1.0 h) and 41 proteins I at (t6.0 h). Total number of proteins, including mutual proteins, is 159.

Reference is now made to Table 15 presenting a list of proteins unique to the BEAKER treated samples (not identified in the BEAKER control samples) and which were identified at more than one time point following treatment.

TABLE 15

BEAKER proteins identified in the treated
samples and in more than one time point 3 time points Uncharacterized protein YbbN YBBN_ECOLI
  1-deoxy-D-xylulose 5-phosphate reductoisomerase DXR
  Small ribosomal subunit biogenesis GTPase RsgA RSGA
2 time points
  t0 + t1 Uncharacterized protein YccU
  Phospho-2-dehydro-3-deoxyheptonate aldolase, Phe-sensitive Arog
  Outer membrane lipoprotein RcsF
  Osmotically-inducible putative lipoprotein OsmE
  Pyridoxal phosphate homeostasis protein Yggs
  t0 + t6 Glutamate synthase [NADPH] small chain Gltd
  Cysteine desulfurase CsdA
  Probable ATP-dependent transporter SufC
  Sec-independent protein translocase protein TatB
  Inner membrane protein YebE
  Sulfate adenylyltransferase subunit 2 Cysd
  Cell division protein FtsN
  23S rRNA (guanosine-2'-O-)-methyltransferase RlmB
  t1 + t6 Trehalose-6-phosphate synthase Otsa
  Guanosine-5'-triphosphate,3'-diphosphate pyrophosphatase Gppa
  Glucarate dehydratase Gudd
  O-acetyl-ADP-ribose deacetylase Ymdb
  30S ribosomal protein S16 RS16
  Spermidine N(1)-acetyltransferase Atda
  Hexitol phosphatase B Hxpb
  3-deoxy-D-manno-octulosonate 8-phosphate phosphatase KdsC Reference is now made to Table 16 presenting a list of proteins unique to the treated Petri Dish samples (not identified in the Petri Dish control samples)

TABLE 16A

Petri Dish (PD) proteins identified in the treated
samples and not in the control samples
at (t0), N = 57

| | |
|---|---|
| PYRI_ECOLI | Aspartate carbamoyltransferase regulatory chain |
| YHHA_ECOLI | Uncharacterized protein YhhA |
| ZAPD_ECOLI | Cell division protein ZapD |
| RIBA_ECOLI | GTP cyclohydrolase-2 |
| YIAD_ECOLI | Probable lipoprotein YiaD |
| UDG_ECOLI | UDP-glucose 6-dehydrogenase |
| GLTD_ECOLI | Glutamate synthase [NADPH] small chain |
| GABD_ECOLI | Succinate-semialdehyde dehydrogenase [NADP(+)] GabD |
| PYRF_ECOLI | Orotidine 5'-phosphate decarboxylase |
| ARGE_ECOLI | Acetylornithine deacetylase |
| FTSN_ECOLI | Cell division protein FtsN |
| PAL_ECOLI | Peptidoglycan-associated lipoprotein |
| DXR_ECOLI | 1-deoxy-D-xylulose 5-phosphate reductoisomerase |
| SOHB_ECOLI | Probable protease SohB |
| ADD_ECOLI | Adenosine deaminase |
| YDHR_ECOLI | Putative monooxygenase YdhR |
| YCII_ECOLI | Protein YciI |
| ARAD_ECOLI | L-ribulose-5-phosphate 4-epimerase AraD |
| GLND_ECOLI | Bifunctional uridylyltransferase/uridylyl-removing enzyme |
| PDXJ_ECOLI | Pyridoxine 5'-phosphate synthase |
| RODZ_ECOLI | Cytoskeleton protein RodZ |
| YAAA_ECOLI | UPF0246 protein YaaA |
| YFCH_ECOLI | Epimerase family protein YfcH |
| FUCI_ECOLI | L-fucose isomerase |
| HEM3_ECOLI | Porphobilinogen deaminase |

TABLE 16A-continued

Petri Dish (PD) proteins identified in the treated samples and not in the control samples at (t0), N = 57

| | |
|---|---|
| YECJ_ECOLI | Uncharacterized protein YecJ |
| RUVA_ECOLI | Holliday junction ATP-dependent DNA helicase RuvA |
| RL32_ECOLI | 50S ribosomal protein L32 |
| YDJN_ECOLI | L-cystine transporter YdjN |
| QUEC_ECOLI | 7-cyano-7-deazaguanine synthase |
| SPPA_ECOLI | Protease 4 |
| RNPH_ECOLI | Inactive ribonuclease PH |
| SUFS_ECOLI | Cysteine desulfurase |
| EPTA_ECOLI | Phosphoethanolamine transferase EptA |
| NARP_ECOLI | Nitrate/nitrite response regulator protein NarP |
| RUVB_ECOLI | Holliday junction ATP-dependent DNA helicase RuvB |
| KDSC_ECOLI | 3-deoxy-D-manno-octulosonate 8-phosphate phosphatase KdsC |
| YKGE_ECOLI | Uncharacterized protein YkgE |
| DDPA_ECOLI | Probable D,D-dipeptide-binding periplasmic protein DdpA |
| YFCZ_ECOLI | UPF0381 protein YfcZ |
| PPA_ECOLI | Periplasmic AppA protein |
| YFCF_ECOLI | Glutathione S-transferase YfcF |
| MLAA_ECOLI | Probable phospholipid-binding lipoprotein MlaA |
| ABGA_ECOLI | p-aminobenzoyl-glutamate hydrolase subunit A |
| SFSA_ECOLI | Sugar fermentation stimulation protein A |
| FEPA_ECOLI | Ferrienterobactin receptor |
| LPTB_ECOLI | Lipopolysaccharide export system ATP-binding protein LptB |
| RS8_ECOLI | 30S ribosomal protein S8 |
| YBBN_ECOLI | Uncharacterized protein YbbN |
| YHGF_ECOLI | Protein YhgF |
| UVRD_ECOLI | DNA helicase II |
| GLPD_ECOLI | Aerobic glycerol-3-phosphate dehydrogenase |
| SPEE_ECOLI | Polyamine aminopropyltransferase |
| GUDD_ECOLI | Glucarate dehydratase |
| YGFB_ECOLI | UPF0149 protein YgfB |
| YCAR_ECOLI | UPF0434 protein YcaR |
| CUSA_ECOLI | Cation efflux system protein CusA |

TABLE 16B

Petri Dish Petri Dish (PD) proteins identified in the treated samples and not in the control samples at (t1.0h), N = 42

| | |
|---|---|
| YEAK_ECOLI | Uncharacterized protein YeaK |
| RNC_ECOLI | Ribonuclease 3 |
| RSMG_ECOLI | Ribosomal RNA small subunit methyltransferase G |
| HIS8_ECOLI | Histidinol-phosphate aminotransferase |
| THIL_ECOLI | Thiamine-monophosphate kinase |
| MNME_ECOLI | tRNA modification GTPase MnmE |
| ZAPA_ECOLI | Cell division protein ZapA |
| NUDK_ECOLI | GDP-mannose pyrophosphatase NudK |
| OPPF_ECOLI | Oligopeptide transport ATP-binding protein OppF |
| GLSA1_ECOLI | Glutaminase 1 |
| ARNC_ECOLI | Undecaprenyl-phosphate 4-deoxy-4-formamido-L-arabinose transferase |
| HIS5_ECOLI | Imidazole glycerol phosphate synthase subunit HisH |
| DUT_ECOLI | Deoxyuridine 5'-triphosphate nucleotidohydrolase |
| NLPE_ECOLI | Lipoprotein NlpE |
| BEPA_ECOLI | Beta-barrel assembly-enhancing protease |
| YGJR_ECOLI | Uncharacterized oxidoreductase YgjR |
| GLTD_ECOLI | Glutamate synthase [NADPH] small chain |
| COPA_ECOLI | Copper-exporting P-type ATPase A |
| ARGE_ECOLI | Acetylornithine deacetylase |
| LEXA_ECOLI | LexA repressor |
| SPEE_ECOLI | Polyamine aminopropyltransferase |
| GUDD_ECOLI | Glucarate dehydratase |
| YMDB_ECOLI | O-acetyl-ADP-ribose deacetylase |
| MALK_ECOLI | Maltose/maltodextrin import ATP-binding protein MalK |
| RSTA_ECOLI | Transcriptional regulatory protein RstA |
| YFCH_ECOLI | Epimerase family protein YfcH |
| RSGA_ECOLI | Small ribosomal subunit biogenesis GTPase RsgA |
| WECB_ECOLI | UDP-N-acetylglucosamine 2-epimerase |
| RHLE_ECOLI | ATP-dependent RNA helicase RhlE |

TABLE 16B-continued

Petri Dish Petri Dish (PD) proteins identified in the treated samples and not in the control samples at (t1.0h), N = 42

| | |
|---|---|
| RUVA_ECOLI | Holliday junction ATP-dependent DNA helicase RuvA |
| RNPH_ECOLI | Inactive ribonuclease PH |
| RDGC_ECOLI | Recombination-associated protein RdgC |
| SECY_ECOLI | Protein translocase subunit SecY |
| RIBB_ECOLI | 3,4-dihydroxy-2-butanone 4-phosphate synthase |
| OPGH_ECOLI | Glucans biosynthesis glucosyltransferase H |
| YIHW_ECOLI | Uncharacterized HTH-type transcriptional regulator YihW |
| POTD_ECOLI | Spermidine/putrescine-binding periplasmic protein |
| TRPA_ECOLI | Tryptophan synthase alpha chain |
| GPR_ECOLI | L-glyceraldehyde 3-phosphate reductase |
| GLPD_ECOLI | Aerobic glycerol-3-phosphate dehydrogenase |
| SOHB_ECOLI | Probable protease SohB |
| MOAB_ECOLI | Molybdenum cofactor biosynthesis protein B |

TABLE 16C

Petri Dish (PD) proteins identified in the treated samples and not in the control samples at (t6.0h), N = 35

| | |
|---|---|
| HIS7_ECOLI | Histidine biosynthesis bifunctional protein HisB |
| STPA_ECOLI | DNA-binding protein StpA |
| F16PA_ECOLI | Fructose-1,6-bisphosphatase class 1 |
| YQFB_ECOLI | UPF0267 protein YqfB |
| RLMJ_ECOLI | Ribosomal RNA large subunit methyltransferase J |
| YAJD_ECOLI | Putative HNH nuclease YajD |
| YIAF_ECOLI | Uncharacterized protein YiaF |
| SECF_ECOLI | Protein translocase subunit SecF |
| YECJ_ECOLI | Uncharacterized protein YecJ |
| RL32_ECOLI | 50S ribosomal protein L32 |
| TOLQ_ECOLI | Protein TolQ |
| YEAK_ECOLI | Uncharacterized protein YeaK |
| RNC_ECOLI | Ribonuclease 3 |
| ARNC_ECOLI | Undecaprenyl-phosphate 4-deoxy-4-formamido-L-arabinose transferase |
| XYLA_ECOLI | Xylose isomerase |
| UDG_ECOLI | UDP-glucose 6-dehydrogenase |
| NARL_ECOLI | Nitrate/nitrite response regulator protein NarL |
| LEXA_ECOLI | LexA repressor |
| YMDB_ECOLI | O-acetyl-ADP-ribose deacetylase |
| ARAD_ECOLI | L-ribulose-5-phosphate 4-epimerase AraD |
| YMBA_ECOLI | Uncharacterized lipoprotein YmbA |
| FOLC_ECOLI | Dihydrofolate synthase/folylpolyglutamate synthase |
| PIMT_ECOLI | Protein-L-isoaspartate O-methyltransferase |
| YFCH_ECOLI | Epimerase family protein YfcH |
| TOLA_ECOLI | Protein TolA |
| YKGF_ECOLI | Uncharacterized electron transport protein YkgF |
| RNPH_ECOLI | Inactive ribonuclease PH |
| DAPE_ECOLI | Succinyl-diaminopimelate desuccinylase |
| GLNQ_ECOLI | Glutamine transport ATP-binding protein GlnQ |
| YDCF_ECOLI | Protein YdcF |
| ASTC_ECOLI | Succinylornithine transaminase |
| SAD_ECOLI | Succinate semialdehyde dehydrogenase [NAD(P)+] Sad |
| RF3_ECOLI | Peptide chain release factor RF3 |
| YEJL_ECOLI | UPF0352 protein YejL |
| UVRD_ECOLI | DNA helicase II |

Figure 15:
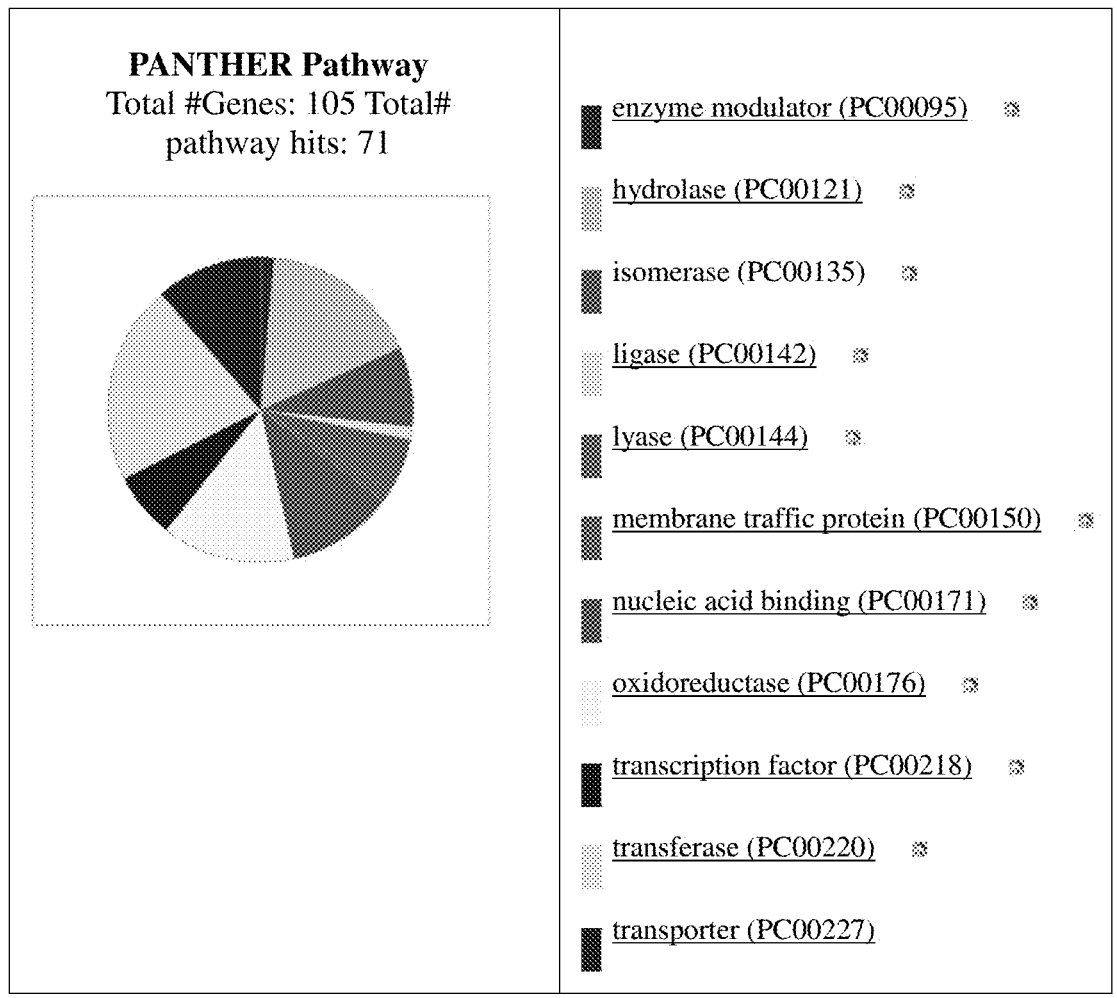
FIG. 15 is a diagram presenting protein class analysis, in *E. coli* treatment samples of shallow solution (Petri Dish), identified by the Panther software.
Figure 16:
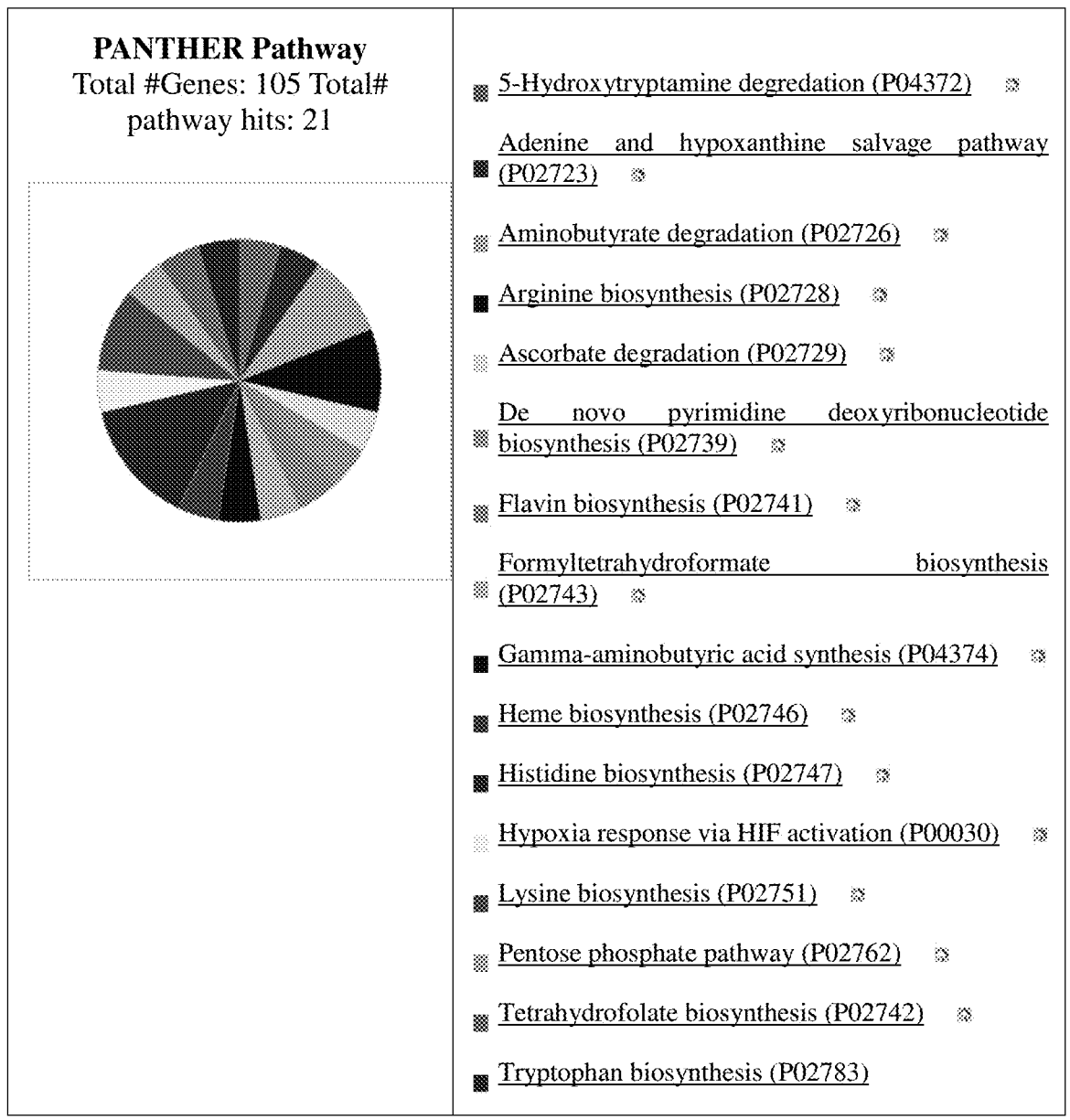
FIG. 16 is a diagram presenting protein pathways analysis, in *E. coli* treatment samples of shallow solution (Petri Dish), identified by the Panther software.

Reference is now made to FIGS. 15, 16 showing protein class analysis and protein pathways, respectively, in treatment samples of Petri Dish, identified by the Panther software.

Figure 17:
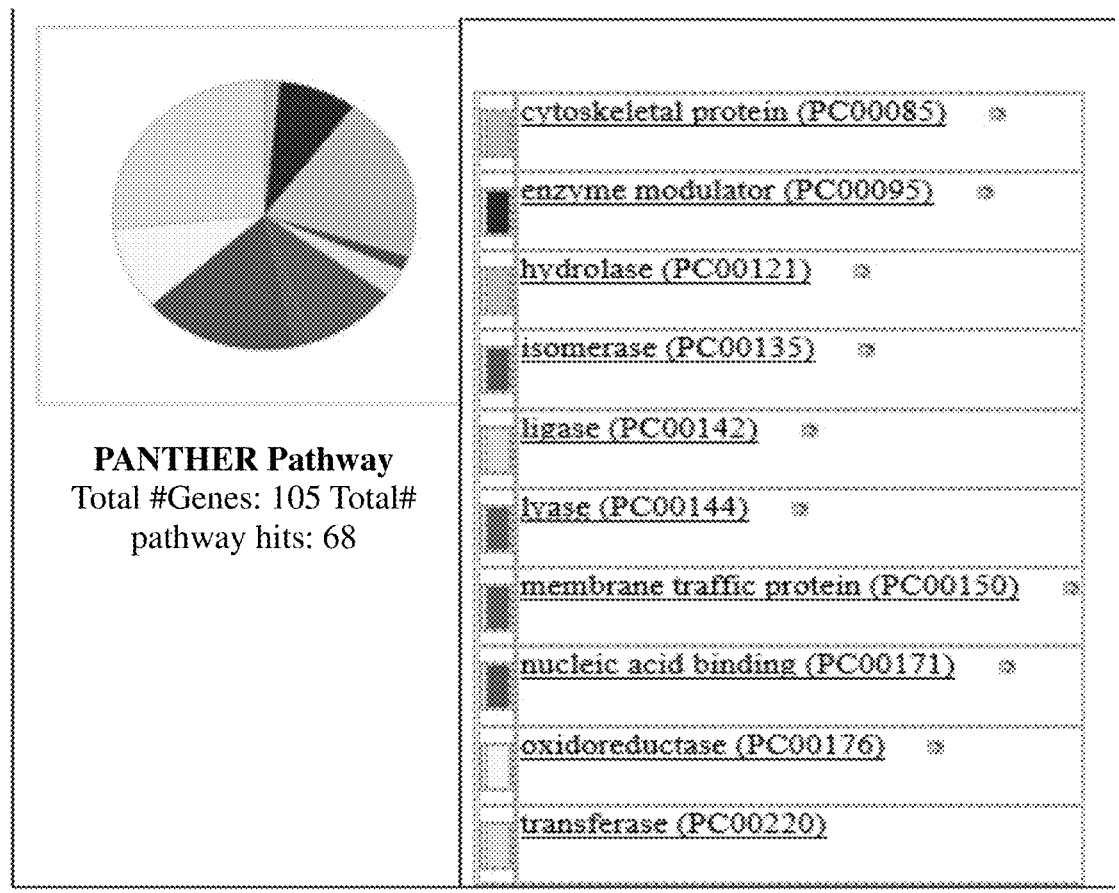
FIG. 17 is a diagram presenting protein class analysis, in *E. coli* control samples of shallow solution (Petri Dish), identified by the Panther software.

Reference is now made to FIG. 17 and FIG. 18 showing protein class analysis and protein pathways, respectively, in control samples in Petri Dish, identified by the Panther software.

The results presented in FIG. 15-18 show that the proteins identified in the treatment samples, were different than proteins identified in the control samples, especially regrading to abundancy of protein classes. The most abundant protein groups, regarding the protein abundancy are similar; however, their abundancy differs: oxidoreductase transferase, hydrolase, and nucleic acid binding.

Additionally, FIGS. 15-18 show difference in protein pathways analyzed in the treated compared to control yeasts cells. Comparing protein pathways in the treated to control *E. Coli* cells showed that the most abundant identified protein pathways for the treated samples, are: Histidine biosynthesis (14.5%), lysine biosynthesis (9.5%), Arginine biosynthesis (9.5%) and aminobutyrate (9.5%); compared to abundant protein pathways identified in control samples: De novo pyrimidine deoxyribonucleotide biosynthesis (13.6%), De novo purine biosynthesis (9.1%), Formyltetrahydroformate biosynthesis (9.1%) and N-acetylglucosamine metabolism (9.1%).

In general, the above findings indicate that the treatment of the present invention affects the profile and the pathways of the induced/formed proteins.

Figure 19:
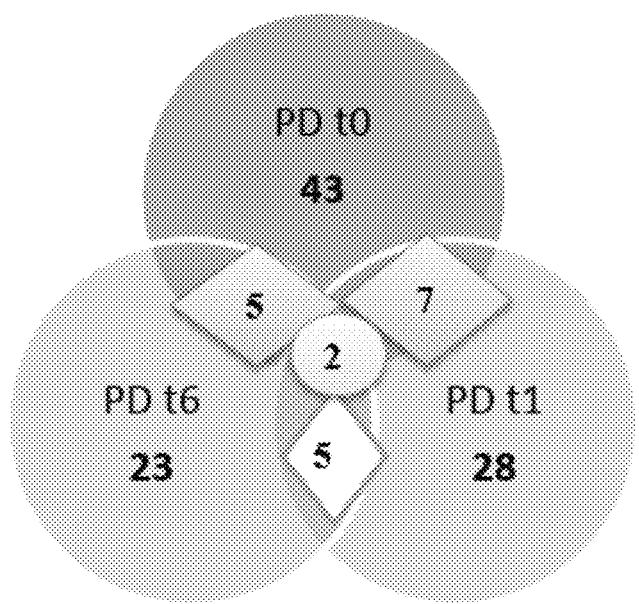
FIG. 19 presents the number of unique proteins identified after treatment in shallow solution (Petri Dish)

Reference is now made to FIG. 19, the number of unique proteins identified after treatment in Petri Dish (PD) is 94, 43 unique proteins at (t0), 28 proteins at (t1.0 h) and 23 proteins at (t6.0 h). Total number of unique proteins formed in treated PD samples (and not in control samples), including mutual proteins, is 113.

Reference is now made to Table 17 presenting a list of proteins unique to the PD treated samples (not identified in the PD control samples) and which were identified at more than one time point following treatment.

TABLE 17

PD proteins identified in the treated
samples and in more than one time point

Petri Dish
3 time points Epimerase family protein YfcH
    Inactive ribonuclease PH Rnph
2 time points
t0 + t0.0h Glutamate synthase [NADPH] small chain Gltd
    Probable protease SohB
    Holliday junction ATP-dependent DNA helicase RuvA
    Aerobic glycerol-3-phosphate dehydrogenase Glpd
    Polyamine aminopropyltransferase SPEE
    Glucarate dehydratase Gudd
    Acetylornithine deacetylase Arge
t0 + t6.0h Uncharacterized protein YecJ
    50S ribosomal protein L32 RL32
    UDP-glucose 6-dehydrogenase Udg
    L-ribulose-5-phosphate 4-epimerase AraD
    DNA helicase II Uvrd
t1.0h + t6.0h Uncharacterized protein YeaK
    Ribonuclease 3 Rnc
    Undecaprenyl-phosphate 4-deoxy-4-formamido-L-arabinose
    transferase
    Arnc
    LexA repressor Lexa
    O-acetyl-ADP-ribose deacetylase Ymdb Reference is now made to Table 18 presenting the number of proteins unique to either treatment or control samples, in BEAKER and in PD. The difference between the groups is significant as indicated by chi-square test, ($\chi^2$=9.674 (p<0.01)).

TABLE 18

Number of proteins unique to treatment
or control samples, in BEAKER and in PD

| | Treated | Control |
|---|---|---|
| Beaker | 159 | 99 |
| Petri Dish | 113 | 124 |

For assessing the affinity between the proteins uniquely formed in treatment cells of BEAKER compared to those formed in PD, the overlap was tested in various time points following treatment:
toB∩t0Pd=8; t1B∩t1PD=4; t6B𝛺t6PD=4

Thus, 16 proteins are common, therefore total proteins in treatment cells of BEAKER which are specific for BEAKER are 159−16=143. This results indicate that 90% of proteins formed in BEAKER treatment cells are unique for the BEAKER and only 10% are common for both the BEAKER and the PD treatment cells.

In control cells of BEAKER, 57% are specific for BEAKER and 33% are common for both the BEAKER and the PD control cells.

Total proteins in treatment cells of PD which are specific for PD are 113−16=97. This results indicate that 86% of proteins formed in PD treatment cells are unique for the PD and only 14% are common for both the BEAKER and the PD treatment cells.

In the control cells of PD, 73% are specific for PD and 27% are common for both the BEAKER and the PD control cells.

In general, these results indicate that the depth of the solution also affect the number of formed unique proteins. Furthermore, the effect of this current technologic exerts its effects into the depth of the solution and not only to the surface. This finding also correlates with an additional finding revealed in 2D DIGE test.

Figure 20:
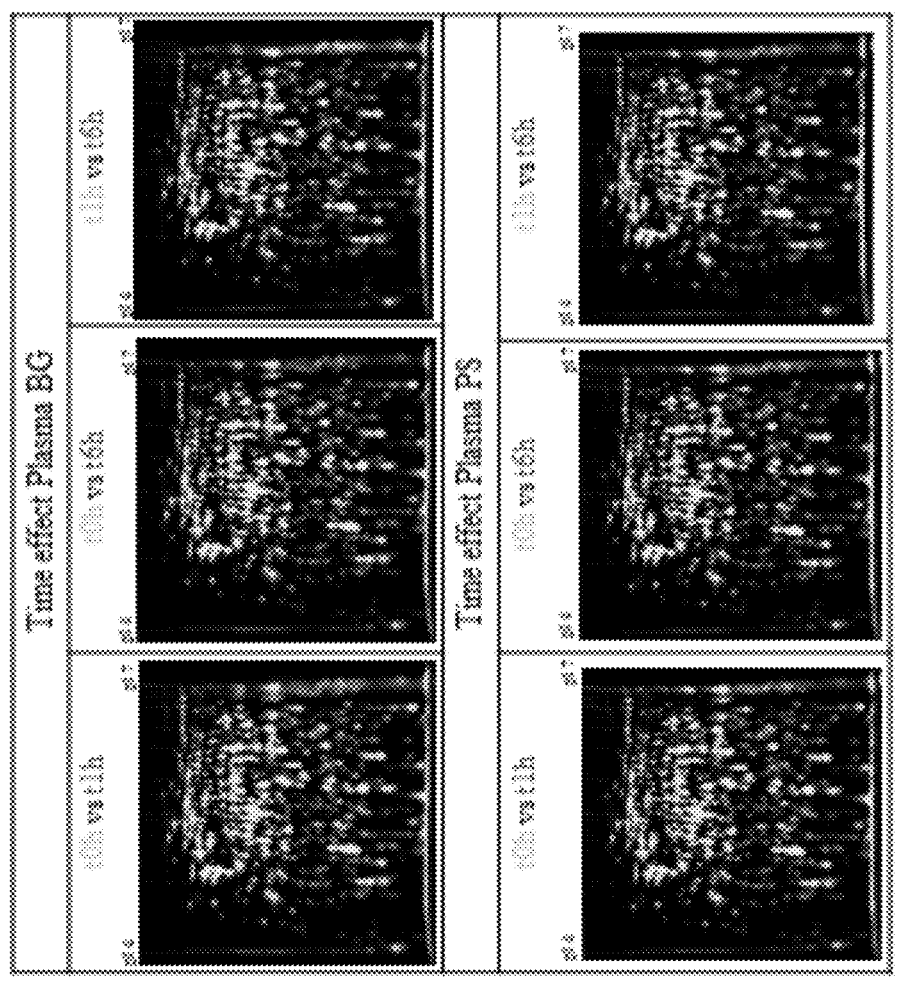
FIG. 20 photographically presents gels of proteins as a function of time as an effect of the solution depth (Beaker versus Petri Dish) in treated cells.

This finding also correlates with an additional finding revealed in 2D DIGE test. Reference is now made to FIG. 20 presenting gels of proteins as a function of time effect by depth (Beaker versus Petri Dish) in treated cells.

This figure indicates a sustained difference of the treatment effects regarding the mobility/alteration/positioning of the proteins in the two-dimensional plan, as a function of time. These findings show that in BEAKER, the location of the proteins at 1 hour after treatment, is very pronounced (see red line on the upper left gel, FIG. 16) an dis mainly based on the proteins' molecular weights. Assessing the location of the protein at other time points reveled that these proteins are distributed along the length and the width pf the gel. Assessing the location of proteins of treated cells in Petri Dish (PS) over time revealed distribution of these proteins along the length and the width pf the gel at all time points.

Figure 21:
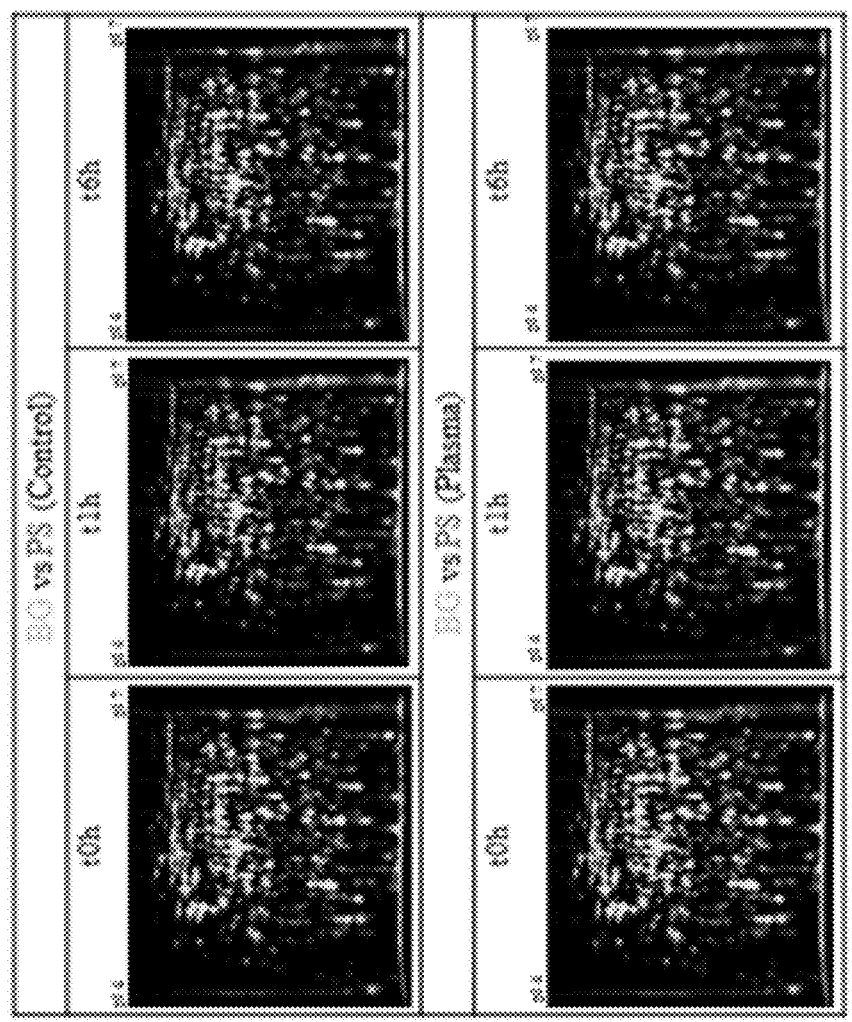
FIG. 21 photographically presents comparison of proteins' gels as a function of time as an effect of the solution depth (Beaker versus Petri Dish) in control cells versus treated cells.

Reference is now made to FIG. 21 comparing gels of proteins of as a function of effect by depth (Beaker versus Petri Dish) in control cells versus treated cells. The results presented additionally indicated that the location of the proteins in the gel has a specific pattern at the first time point following treatment (t0) and this pattern changes over time as indicated by protein detection at 1 h and 6 h following treatment.

II. Identification of Selected Unique Proteins Downregulated or Upregulated by Treatment LC-MS analysis revealed the number and identity pf proteins which were downregulated or upregulated in treatment cells, as compared to control cell at all time points and in any group (BEAKER or PD).

Reference is now made to Tables 19-20. Tables 19 and 20 present the identity of the proteins which were upregulated (Table 19) or downregulated (Table 20) in the BEAKER treated samples only in at least one time point. Table 19 further presents proteins which were upregulated in two time points (marked in bold); while Table 20 further presents proteins which were downregulated in two time points (marked in bold). There are several proteins, for example ALC-ECOLI which are upregulated at one time point (at t1.0 h) and downregulated at another time point (t6.0 h).

TABLE 19

BEAKER upregulated proteins of treated samples (N = 30)
Protein Name dTDP-glucose 4,6-dehydratase 1 - RMLB1_ECOLI
Hexitol phosphatase A - YFBT_ECOLI
Ribosome hibernation promoting factor - HPF_ECOLI
Lipopolysaccharide export system ATP-binding protein LptB LPTB_ECOLI
Fumarate reductase iron-sulfur subunit - FRDB_ECOLI
Modulator of drug activity B - MDAB_ECOLI
Sulfur acceptor protein CsdE - CSDE_ECOLI
Transcriptional regulatory protein BaeR - BAER_ECOLI
Glutamate-pyruvate aminotransferase AlaA - ALAA_ECOLI
GMP reductase - GUAC_ECOLI
Glutamate 5-kinase (upregulated in two time points) - PROB_ECOLI
UTP--glucose-1-phosphate uridylyltransferase - GALF_ECOLI
Pyridoxal phosphate homeostasis protein - upregulated in two time points) YGGS_ECOLI
Dual-specificity RNA methyltransferase RlmN - RLMN_ECOLI
N-methyl-L-tryptophan oxidase (upregulated in 2 time points - MTOX_ECOLI)
Ubiquinone/menaquinone biosynthesis C-methyltransferase UbiE - UBIE_ECOLI
Glutamate-pyruvate aminotransferase AlaC - ALAC_ECOLI
DNA ligase - DNLJ_ECOLI
Fructokinase - MAK_ECOLI
Dihydrofolate reductase - DYR_ECOLI
Putative carboxymethylenebutenolidase - DLHH_ECOLI
Malate synthase G - MASZ_ECOLI
Chromosome partition protein MukB - MUKB_ECOLI
PTS system mannitol-specific EIICBA component - PTM3C_ECOLI
Transcriptional repressor NrdR - NRDR_ECOLI
L-glyceraldehyde 3-phosphate reductase - GPR_ECOLI
UPF0227 protein YcfP - YCFP_ECOLI
D-serine dehydratase - SDHD_ECOLI
Orotidine 5'-phosphate decarboxylase - PYRF_ECOLI
Uncharacterized electron transport protein YkgF - 30YKGE_ECOL

TABLE 20

BEAKER downregulated proteins of treated samples (N = 12)
Protein name

FKBP-type 16 kDa peptidyl-prolyl cis-trans isomerase - FKBX_ECOLI
Probable lipoprotein YiaD - YIAD_ECOLI
Tryptophan synthase beta chain - TRPB_ECOLI
Glutamate-pyruvate aminotransferase AlaC - ALAC_ECOLI &&
Uncharacterized protein YccU- YCCU_ECOLI
Ubiquinone/menaquinone biosynthesis C-methyltransferase UbiE - UBIE_ECOLI &&
Dual-specificity RNA methyltransferase RlmN - RLMN_ECOLI
Sulfate adenylyltransferase subunit 2 (down regulated in 2 time points)-
CYSD_ECOLI
Nucleoside diphosphate kinase - NDK_ECOLI
Thiol: disulfide interchange protein DsbA - DSBA_ECOLI
**Uncharacterized protein YccU * 2 - YCCU_ECOLI (down regulated in**
2 time points)
P-protein - PHEA_ECOLI Reference is now made to Tables 21-22. Tables 21 and 22 present the names of the proteins which were upregulated (Table 21) or downregulated (Table 22) in the Petri Dish treated samples only in at least one time point. Table 21 further presents proteins which were downregulated in two time points (marked in bold). There are several proteins, for example FTSN-ECOLI which are downregulated at one time point (at t0) and upregulated at another time point (t1.0 h)(marked in bold and italics).

TABLE 21

Petri Dish upregulated proteins of treated samples (N = 11)
PD up regulation in all time points Lipopolysaccharide export system ATP-binding protein LptB - LPTB_ECOLI
Probable lipoprotein YiaD- YIAD_ECOLI
Cell division protein FtsN -FTSN_ECOLI
Adenosine deaminase - ADD_ECOLI
L-cystine transporter YdjN - YDJN_ECOLI
Cation efflux system protein CusA - CUSA_ECOLI
Orotidine 5'-phosphate decarboxylase - PYRF_ECOLI
Beta-barrel assembly-enhancing protease - BEPA_ECOLI
Uncharacterized oxidoreductase YgjR - YGJR_ECOLI
L-glyceraldehyde 3-phosphate reductase - GPR_ECOLI
Ribosomal RNA small subunit methyltransferase G - RSMG_ECOLI

TABLE 22

Petri Dish downregulated proteins of treated samples (N = 11)
PD Down regulation in all time points

Uncharacterized protein YeaK - YEAK_ECOLI (at 2 time points)
Uncharacterized HTH-type transcriptional regulator YihW-YIHW_ECOLI
Molybdenum cofactor biosynthesis protein B - MOAB_ECOLI
GDP-mannose pyrophosphatase NudK - NUDK_ECOLI
Probable protease SohB - SOHB_ECOL (at 2 time points)
*Orotidine 5' -phosphate decarboxylase -PYRF _ECOLI*
UPF0149 protein YgfB - YGFB_ECOLI
*Adenosine deaminase - ADD_ECOLI*
Aspartate carbamoyltransferase regulatory chain - PYRI_ECOLI
Cytoskeleton protein RodZ - RODZ_ECOLI
Cell division protein FtsN - FTSN_ECOLI Reference is now made to Table 23.

TABLE 23

Number of unique proteins of treated samples,
as a function of location and time

| | BEAKER | Petri Dish | Common |
|---|---|---|---|
| t0 | 30 | 52 | 3 |
| t2.0h | 44 | 51 | 8 |
| t6.0h | 30 | 50 | 6 |
| Total | 104 | 153 | 17 |

Table 23 presents the number of the unique proteins which were detected following treatment only, are common to both PD and BEAKER, and were downregulated as a result pf the treatment at the various time points.

Findings presented in Tables 21-23 indicate that 86% of downregulated proteins are unique for the BEAKER while 90% of the proteins of downregulated proteins are unique for the Petri Dish. This finding further supports the indication that the treatment affects differently the cells/organisms which are located in various depths of the solution, and is not limited only to the surface of the cells/solutions.

Example 3

Reference is now made to Table 24, presenting the technical characteristics of the plasma system used for the current invention.

TABLE 24

Technical characterization of the plasma
system of the present invention

| General | |
|---|---|
| Dimension L × W × H | 900 mm 400 mm 1470 mm |
| Supply voltage frequency | 115-230 V ac 50/60 Hz |
| Max power consumption | 50 VA |
| Protection class | IP30 |
| Gas supply | |
| Type of gas | Mixture as specified |
| Purity | Min 4.6 |
| Gas flow rate | 40 +/− 1 slm (standard liter per min) |
| Inlet pressure | 2-3 bar (2-3 × 10E5 Pa) |
| Supply Unit (Operating device) | |
| Dimension L × W × H | 350 mm 270 mm 200 mm |
| Safety class | IP40 |
| Plasma generator | |
| Dimension Φ × H | 230 mm × 240 mm |
| Supply Line length | 1.5 m |
| Safety Class | IP30 |
| Total weight | 4.0 kg |
| Mains Fuse | T630mAL250V |

Reference is now made to Table 25, presenting the ambient conditions for the operation of said plasma system used for the current invention.

TABLE 25

Ambient conditions for the plasma Generator

| Transport | |
|---|---|
| Teperature: | −40-70 |
| Relative air Humidity | 10-80% |
| Operation | |
| Temperature | 15-40 c. |
| Relative air Humidity | 15-75% |
| Air Pressure | 800-1060 hPa |

Figure 22:
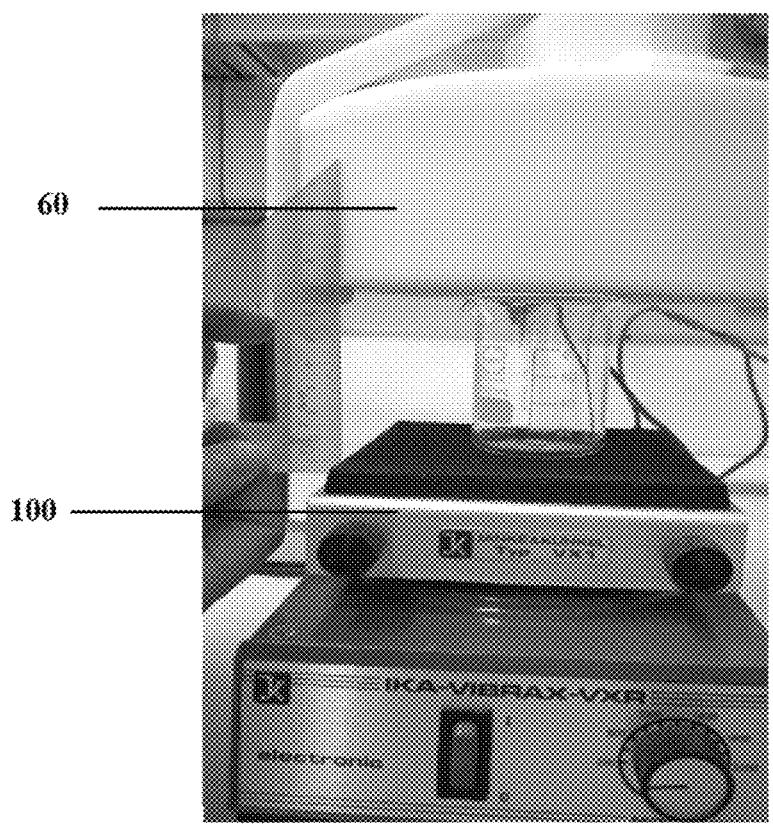
FIG. 22 photographically presents embodiments of the system of the present invention.

Reference is now made to FIG. 22 photographically presenting embodiments of the system of the present invention. The figure illustrates the position of the plasma system of the present invention (60), including the plasma discharge source and the plasma modifying mechanism, with respect to the treated sample (e.g. contained in a beaker) placed on a support or base (100). The distance between the plasma modifying system and the treated sample is defined as the distance between the base, where the sample container (e.g. BEAKER or Petri Dish) is located, and the lower part of the plasma modifying system. This distance may be varies between about 3 cm and about 10 cm, particularly between about 3 cm and about 7 cm.

Pulse characterization: The pulse profile comprises a rate unit (pulse cycle) having a defined pattern; while the number of pulses in one treatment session is characterized by the number of rate units (or pulse cycles). For example, four pulse cycles are four pre-defined rate units, while seven pulse cycles are seven pre-defined rate units.

Pulses can be of various types, which mean having different rate units or pulse cycles pattern, as defined above.

Some of the parameters defining the pulse profile include:
 i. Number of pulse cycles in use; the number value may range between 3 to 20.
 ii. Time period for a rate unit or pulse cycle; the time period value ranges between 9 to 101 seconds (or between 0.15 to 1.68 minutes).
 iii. Number of ON and OFF actions for each rate unit or pulse cycle. Accordingly, the rate units can be characterize by the number of ON and OFF actions; ranging from 6-57 "on pulses" and 3-44 pauses.

The intensity of the electric filed is 200-500V/m, at maximal flow.

The modifying plasma mechanism of the current invention comprises a combination of crystal mirrors (optical crystal material), serving as reflectors or focusing elements and small magnets (magnetic material).

The frequencies for the plasma, magnets and reflectors are very low frequencies, preferably between 3 KHz to 30 KHz.

Examples of plasma devices included within the scope of the present invention are described in U.S. Pat. No. 8,896,211.

Figure 23:
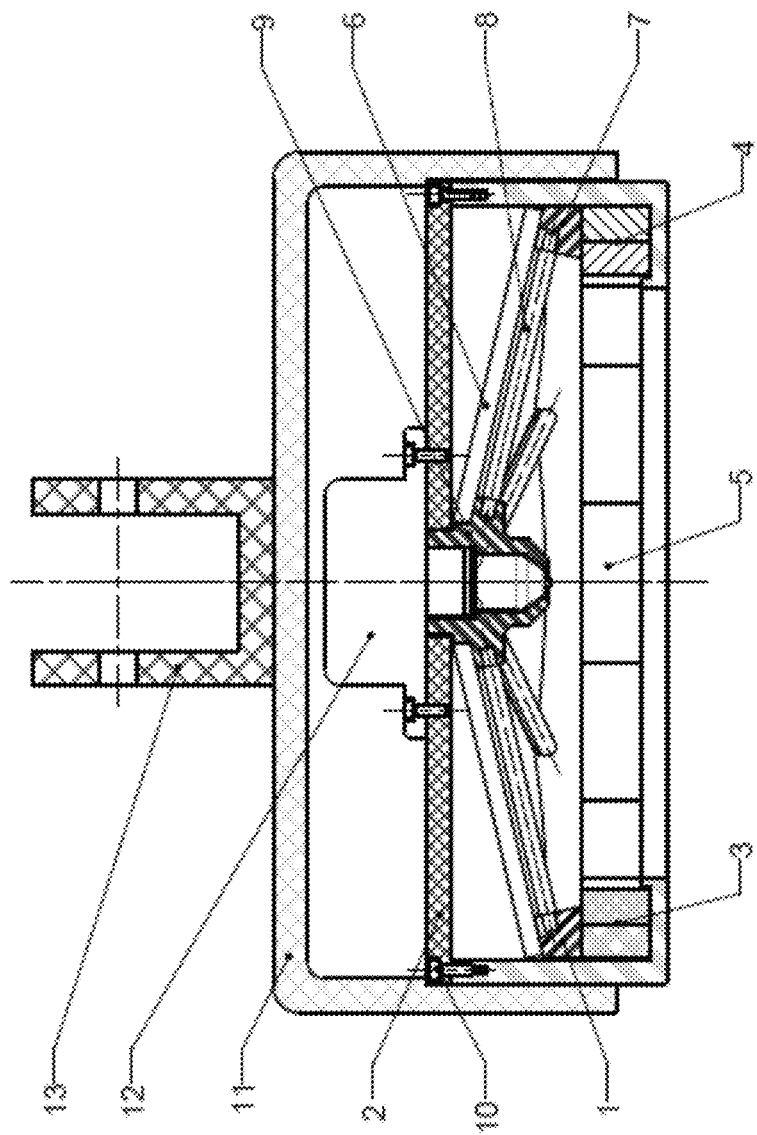
FIG. 23 schematically presents embodiments of the plasma modifying mechanism device head; as alternative embodiments of the present invention.

Reference is now made to FIG. 23, presenting a scheme of embodiments of the plasma modifying mechanism device head.

Table 26 below describes embodiments presented in FIG. 23:

| | | |
|---|---|---|
| 13 | Clevis | POM |
| 12 | Modified plasma jet | POM-cover |
| 11 | Holder | POM |
| 10 | Screw | POM |
| 9 | Mount | POM |
| 8 | Strut | POM |
| 7 | Spacer | POM |
| 6 | Mirror | Optical Crystal material |
| 5 | Magnet | Magnetic material |
| 4 | Magnet | Magnetic material |
| 3 | PTZ | Piezoelectric material |
| 2 | Disc | POM |
| 1 | Cover | POM |

POM = Polyoxymethylene

Figure 24A:
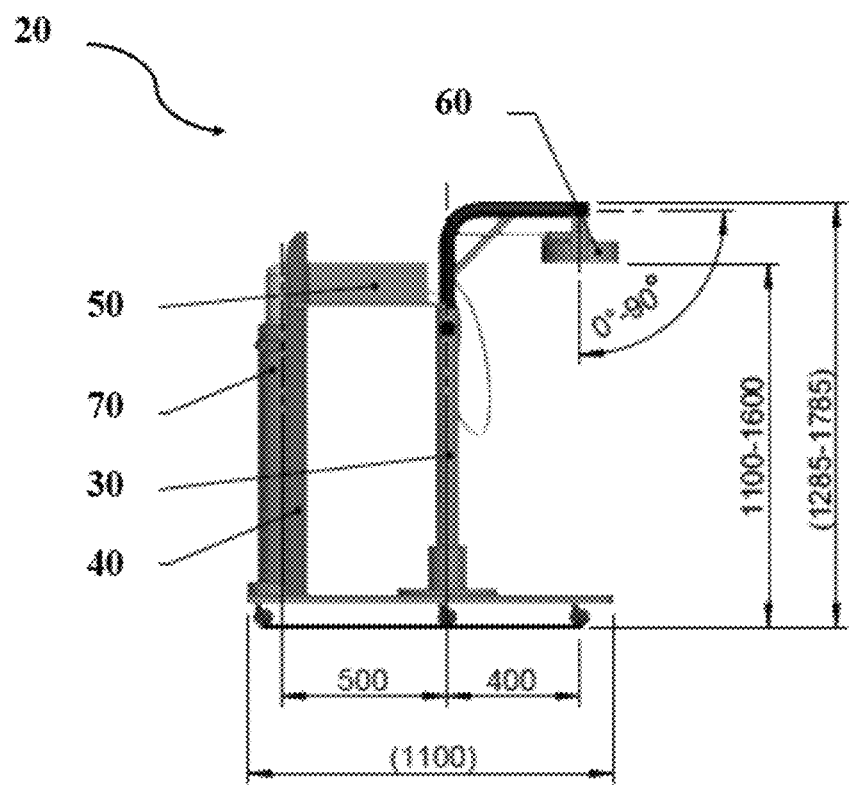
FIGS. 24A-24B schematically presents embodiments of the pedestral in side view (FIG. 24A) and upper or top view (FIG. 24B).
Figure 24B:
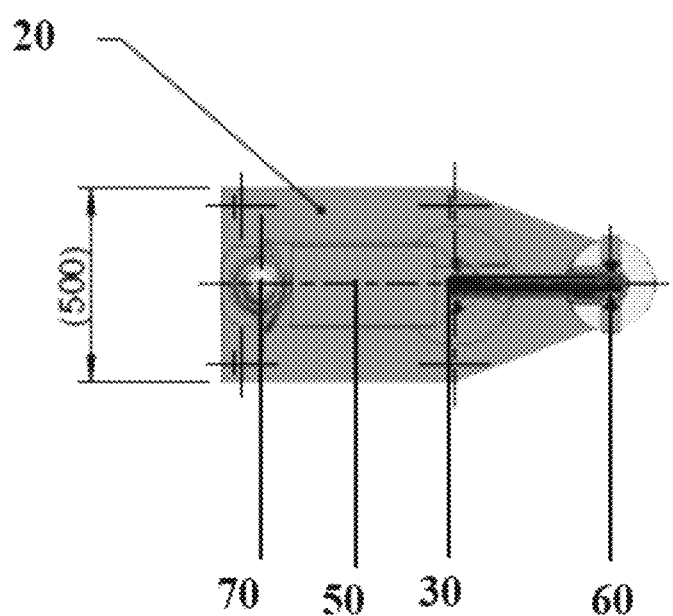

Reference is now made to FIG. 24, presenting a scheme of embodiments of the pedestral in side view (FIG. 24A) and upper or top view (FIG. 24B).

Table 27 below describes embodiments presented in FIG. 24.

| Number | Name | Material |
|---|---|---|
| 70 | Gas bottle | POM -cover |
| 60 | Turnable device with modeified plasmajet | POM |
| 50 | Table and cover for power supply unit | POM |
| 40 | Pretection wall with holder | POM |
| 30 | Holder adjustable in steps 30-50 mm | POM |
| 20 | Base frame with e.g. rolls | Non-metallic |

POM = Polyoxymethylene

The invention claimed is:
1. A system operable in a non-GM method for de-novo generating of proteins in microorganisms from within the proteome of said microorganisms,
  said system comprises
  a. a plasma discharge source for discharging pulses of plasma to said microorganisms, said plasma comprising about 70 to about 98% (wt.) argon, about 6 to about 9% (wt.) nitrogen and about 1.5 to about 2.5% (wt.) oxygen; said plasma discharge electric field is in the range of about 200 to about 500 v/m;
  b. a plasma modifying mechanism comprising (1) at least one magnetic material, and at least one piezoelectric material, and (2) at least one optical crystal material, said plasma modifying mechanism providing modified plasma output having frequencies in the range of about 3 KHz to about 30 KHz; and c. a non-transitory medium providing instructions for said plasma discharge source to discharge said plasma in a predetermined pulsed profile characterized by pulse cycle duration in the range of about 0.1 to about 2.1 min each pulse cycle comprises a series of about 6 to about 57 “on pulses” and about 3 to about 44 pauses and the number of pulse cycles is in the range of about 3 to about 20, and activating proteins from said microorganisms, wherein at least one of said proteins is absent from control microorganisms not exposed to said modified plasma output.

2. A system operable in a non-GM method for modulating proteins in microorganisms, said system comprises a. a plasma discharge source for discharging pulses of plasma to said microorganisms, said plasma comprising about 70 to about 98% (wt.) argon, about 6 to about 9% (wt.) nitrogen and about 1.5 to about 2.5% (wt.) oxygen; the electric field of the discharge of said plasma is in the range of about 200 to about 500 v/m;

b. a plasma modifying mechanism comprising at least one magnetic material, and at least one piezoelectric material, and at least one optical crystal material, said plasma modifying mechanism providing modified plasma output having frequencies in the range of about 3 KHz to about 30 KHz; and c. a non-transitory medium providing instructions for said plasma discharge source to discharge said plasma in a predetermined pulsed profile characterized by pulse cycle duration in the range of about 0.1 to about 2.1 min each pulse cycle comprises a series of about 6 to about 57 “on pulses” and about 3 to about 44 pauses and the number of pulse cycles is in the range of about 3 to about 20, and activating proteins from said microorganisms, wherein at least one of said proteins is absent from control microorganisms not exposed to the modified output of said plasma.

3. A non-GM method for producing a drug or pro-drug, food additive or food supplement, industrial enzyme and any combination thereof by modulating proteins in microorganisms, comprising steps of:

a. providing a system comprising:

i. a plasma discharge source for discharging pulses of plasma to said microorganisms, said plasma comprising about 70 to about 98% (wt.) argon, about 6 to 9% (wt.) nitrogen, and about 1.5 to about 2.5% oxygen by % (wt.); the electric field of the discharge of said plasma is in the range of about 200 to about 500 v/m; and ii. a plasma modifying mechanism comprising at least one magnetic material, and at least one piezoelectric material, and at least one optical crystal material, said plasma modifying mechanism providing modified plasma output having frequencies in the range of about 3 KHz to about 30 KHz;

b. discharging said plasma towards said microorganisms in a pulsed profile, said profile characterized by pulse cycle duration ranging from about 0.1 to about 2.1 min, each pulse cycle comprises a series of 6 to 57 “on pulses” and about 3 to about 44 pauses, number of pulse cycles ranging from about 3 to about 20, thereby modulating proteins from said microorganisms.

* * * * *